United States Patent
Kim et al.

(10) Patent No.: US 9,061,030 B2
(45) Date of Patent: Jun. 23, 2015

(54) SGC STIMULATORS

(75) Inventors: Charles Kim, Cambridge, MA (US); Takashi Nakai, Newton, MA (US); Thomas Wai-Ho Lee, Lexington, MA (US); Joel Moore, Lexington, MA (US); Nicholas Robert Perl, Brookline, MA (US); Jason Rohde, Poolesville, MD (US)

(73) Assignee: IRONWOOD PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 13/883,910

(22) PCT Filed: Nov. 2, 2011

(86) PCT No.: PCT/US2011/058902
§ 371 (c)(1),
(2), (4) Date: Dec. 12, 2013

(87) PCT Pub. No.: WO2012/064559
PCT Pub. Date: May 18, 2012

(65) Prior Publication Data
US 2014/0088071 A1    Mar. 27, 2014

Related U.S. Application Data

(60) Provisional application No. 61/546,707, filed on Oct. 13, 2011, provisional application No. 61/411,730, filed on Nov. 9, 2010.

(51) Int. Cl.
| | | |
|---|---|---|
| *A61K 31/506* | (2006.01) | |
| *C07D 401/04* | (2006.01) | |
| *C07D 401/14* | (2006.01) | |
| *C07D 403/04* | (2006.01) | |
| *C07D 413/14* | (2006.01) | |
| *C07D 417/04* | (2006.01) | |
| *C07D 417/14* | (2006.01) | |
| *C07D 405/14* | (2006.01) | |
| *A61K 31/427* | (2006.01) | |
| *A61K 31/4439* | (2006.01) | |
| *A61K 31/444* | (2006.01) | |

(52) U.S. Cl.
CPC ............ *A61K 31/506* (2013.01); *C07D 401/04* (2013.01); *C07D 401/14* (2013.01); *C07D 403/04* (2013.01); *C07D 413/14* (2013.01); *C07D 417/04* (2013.01); *C07D 417/14* (2013.01); *C07D 405/14* (2013.01); *A61K 31/427* (2013.01); *A61K 31/4439* (2013.01); *A61K 31/444* (2013.01)

(58) Field of Classification Search
CPC ............................ A61K 31/506; C07D 401/04
USPC ...................... 514/210.2; 544/333
See application file for complete search history.

(56) References Cited

U.S. PATENT DOCUMENTS

| | | |
|---|---|---|
| 3,169,966 A | 2/1965 | Schmidt et al. |
| 3,228,946 A | 1/1966 | Schmidt et al. |
| 3,228,997 A | 1/1966 | Schmidt et al. |
| 3,250,761 A | 5/1966 | Schmidt et al. |

(Continued)

FOREIGN PATENT DOCUMENTS

| | | |
|---|---|---|
| DE | 19744026 | 10/1997 |
| DE | 19744027 | 10/1997 |

(Continued)

OTHER PUBLICATIONS

King, Med. Chem. Principle and Practice (1994), pp. 206-208.*
Structures of some compounds found in STN substructure searches in File Registry with dates of STN entries shown with each of the compound records. (Date Unknown).
Skinner, Philip J. et al., "Fluorinated pyrazole acids are agonists of the high affinity niacin receptor GPR109a", Bioorganic & Medicinal Chemistry Letters (2007), 17(20), 5620-5623, Elsevier Ltd., ISSN: 0960-894X.
Yonetoku, Yasuhiro et al., "Novel potent and selective calcium-release-activated calcium (CRAC) channel inhibitors. Synthesis and inhibitory activity of aryl-3-triflouoromethylpyrazoles", Bioorganic & Medicinal Chemistry (2006), 14(15), 5370-5383, Elsevier B.V.

(Continued)

*Primary Examiner* — Taofiq A Solola
(74) *Attorney, Agent, or Firm* — Heslin Rothenberg Farley & Mesiti, P.C.

(57) ABSTRACT

Compounds of Formula IA and Formula IB are described. They are useful as stimulators of sGC, particularly NO-independent, heme-dependent stimulators. These compounds may be useful for treating, preventing or managing various disorders that are herein disclosed.

Formula IA

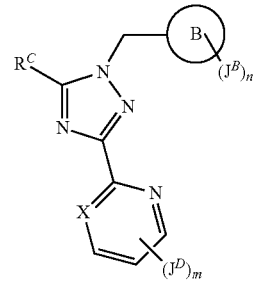

Formula IB

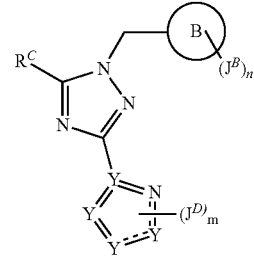

44 Claims, No Drawings

(56) References Cited

U.S. PATENT DOCUMENTS

| 5,470,862 | A | 11/1995 | Lin et al. |
| 6,028,072 | A | 2/2000 | Lee et al. |
| 8,748,442 | B2 | 6/2014 | Kim et al. |
| 2003/0105336 | A1 | 6/2003 | Schindler et al. |
| 2010/0075964 | A1 | 3/2010 | Busch et al. |

FOREIGN PATENT DOCUMENTS

| DE | 19649460 | | 5/1998 |
| EP | 0908456 | A1 | 4/1999 |
| EP | 1433788 | | 12/2002 |
| EP | 1479678 | | 11/2004 |
| EP | 2006288 | A1 | 12/2008 |
| WO | 9307138 | | 4/1993 |
| WO | 93/11433 | A1 | 6/1993 |
| WO | 9715570 | | 5/1997 |
| WO | 9827091 | | 6/1998 |
| WO | 9856785 | | 12/1998 |
| WO | 00/06568 | A1 | 2/2000 |
| WO | 0009500 | | 2/2000 |
| WO | 0027394 | A1 | 5/2000 |
| WO | 0039083 | | 7/2000 |
| WO | 0187287 | | 11/2001 |
| WO | 0218350 | | 3/2002 |
| WO | 03000659 | | 1/2003 |
| WO | 03026649 | | 4/2003 |
| WO | 03039539 | | 5/2003 |
| WO | 2004013135 | | 2/2004 |
| WO | 2004016606 | | 2/2004 |
| WO | 2004069158 | | 8/2004 |
| WO | 2006104141 | | 10/2006 |
| WO | 2006114313 | | 11/2006 |
| WO | 2007002559 | | 1/2007 |
| WO | 2007014054 | | 2/2007 |
| WO | 2008004096 | | 1/2008 |
| WO | 2008024390 | | 2/2008 |
| WO | 2008141731 | | 11/2008 |
| WO | 2009067600 | | 5/2009 |
| WO | 2009076454 | | 6/2009 |
| WO | 2009143039 | | 11/2009 |
| WO | 2010015656 | | 2/2010 |
| WO | 2010015657 | | 2/2010 |
| WO | 2010020366 | A1 | 2/2010 |
| WO | 2010054762 | | 5/2010 |
| WO | 2010054763 | | 5/2010 |
| WO | 2011119518 | A1 | 9/2011 |
| WO | 2011147810 | A1 | 12/2011 |
| WO | 2012003405 | A1 | 1/2012 |
| WO | 2012064559 | A1 | 5/2012 |
| WO | 2012075678 | A1 | 6/2012 |

OTHER PUBLICATIONS

Zhang, Jidong et al., "Potent nonpeptide endothelin antagonists: synthesis and structure-activity relationships of pyrazole-5-carboxylic acids", Medicinal Chemistry, Hoechst Marion Roussel, Bioorganic & Medicinal Chemistry Letters (2000), 10(22), 2575-2578, Elsevier Science Ltd., ISSN: 0960-894X.

Takahashi, Masahiko et al., "Ring transformation of 1, 2, 4, 5-tetrazines to 4-aminopyrazoles by cyanotrimethysilane", Faculty English, Ibaraki University, Hitachi, 316, Japan Tetrahedron Letters (1987), 28(19), 2139-42, TELEAY; ISSN: 0040-4039.

Zabel, Dirk et al., "Iron and cobalt complexes of tridentate N-donor ligands in ethylene polymerization: efficient shielding of the active sites by simple phenyl groups", Fachbereich Chemie, Technische Universitaet Kaiserlautern, European Journal of Inorganic Chemistry (2008), (23), 3648-3654, ISSN: 1434-1948, Wiley-VCH Verlag GmbH Co.

Bouabdallah, Ibrahim et al., "Catecholase activities of two C—C linked Bipyrazole N-donor ligands with copper (II) salts", Laboratory of Organic Chemistry, Macromolecular and Natural Products, Dept. of Chemistry, Faculty of Sciences, University Mohammed the First, Oujda, 60000, Morocco, Journal Marocain de Chimie Heterocyclique (2007), 6(1), 21-25.

Bouabdallah, Ibrahim et al., 1, 1'-Dibenzyl-5, 5'-dipehenyl-3, 3'-bipyrazole, Laboratoric de Chimie Organique Physique, Dept. de Chimi, Faculte des Sciences, Universite Mohammed First, Oujda, 6000, Morocco (2006), ISSN: 1422-8599.

Kalluraya, Balakrishna et al., Reactions of aryl/arylozyacet hydrazides with acetylenic ketones, Dept of Studies in Chemistry, Mangalore University, Mangalagangothri, 574 199, India, Indian Journal of Heterocyclic Chemistry (1999), 8(4), 309-314.

Kost, A.N. et al., "Condensation of 1-acylpyrazolines", Mosk. Gos. University im. Lomonosova, Moscow, USSR Khimiya Geterotsiklicheskikh Soedinenii (1974), (9), 1268-1270. ISSN: 0132-6244.

Khalil, A. et al., "Phase-Transfer Catalyzed Alkylation and 3-Substituted-1H-pyrazol-2-in-5-oncs in the Absence or Presence of Carbon Disulphide", Phosphorus, Sulfur Silicon Relat. Elem. (2005), 180(2), 479-496.

Tarrago, Georges et al., "Orientation de la reaction d'alkylation des pyrazoles dans des conditions neuters et an catalyse par transfer de phase", J. Heterocycl. Chemical (1980), 17(1), 137-142.

Bouabdallah, Ibrahim et al., "Regioselective synthesis and crystal structure of 1, 1'-dibenzyl-5, 5'-diisopropyl-3, 3'-bipyrazole", Journal Marocain de Chimie Heterocylclique (2004), 3(1), pp. 39-44.

Goodell, John R. et al., "Identification of Compounds with Anti-West Nile Virus Activity", Journal of Medicinal Chemistry (2006), 49(6), pp. 2127-2137.

Rostom, Sherif A. F.; Polysubstituted pyrazoles, part 6. Synthesis of some 1-(4-chlorophenyl)-4-hydroxy-1H-pyrazol-3-carbonl derivatives linked to nitrogenous heterocyclic ring systems as potential antitumor agents, Bioorganic & Medicinal Chemistry (2010), 18(7), pp. 2767-2776.

Ye, Long et al., "Pyrazolylthiazole as ΔF508-Cystic Fibrosis Transmembrane Conductance Regulator Correctors with Improved Hydrophilicity Compared to Bithiazoles", Journal of Medicinal Chemistry (2010), 53(9), 3772-3781.

Bonacorso, Helio G. et al., "Synthesis of new trihalomethylated and non-symmetrical substituted 2-(1-H-pyrazolyl)-5-(1H-pyrazolycarbonyl)pyridines", Journal of the Brazilian Chemical Society (2009), 20(3), 509-517.

Sakya, Subas M. et al., "Facile microwave assisted decarbonylation of 4-formyl group in 5-alkyl amino substituted pyrazoles", Tetrahedron Letters (2008), 49(14), 2280-2282, CODEN: TELEAY; ISSN: 0040-4039.

Suen, Yat Fan et al., "A Novel Route to Fully Substituted 1H-Pyrazoles", Journal of Organic Chemistry (2005), 70(21), 8468-8471, CODEN: JOCEAH; ISSN: 0022-3263.

Amer, Fathy A. et al., "Synthesis of 4,4'-aryldihydrazono-3-(3'-pyridyl)-2-pyrazolin-4,5-diones and 1-aryl-3-(3'-pyridyl)-4,4'-arylbizazo-5-aryliminopyrazoles and their application as disazo disperse dyes", Journal of Chemical Technology and Biotechnology (1979-1982) (1980), 30(2), 78-84, CODEN, JCTBDC; ISSN: 0142-0356.

Sawyer et al., Synthesis and Activity of New Aryl- and Heteroaryl-Substituted Pyrazole Inhibitors of the Transforming Growth Factor-β Type 1 Receptor Kinase Domain, Journal of Medicinal Chemistry, 2003, American Chemical Society, vol. 46, No. 19, pp. 3953-3956.

Selwood, David L. et al., "Synthesis and biological evaluation of novel pyrazoles and indazoles as activators of the nitric oxide receptor, soluble guanylate cyclase", Journal of Medicinal Chemistry (2001), (44), 78-93. XP000002658947.

Sergievskii, AV et al., "Reactivity of 3,5-bis-(4-amino-1,2,5-oxadiazol-3-yl)-1,2,4-triazole," Russian Journal of Organic Chemistry, Feb. 1, 2005, 41(2), pp. 261-267.

Takalo, H et al. "Development of luminescent terbium(III) chelates for protein labelling: Effect of triplet-state energy level," Helvetica Chimica Acta, Jan. 1, 1997, 80(2), pp. 372-387.

Johnsen, M et al. "New antithrombotic 1-phthalazinamines with serotonin antagonistic properties," Archiv Der Pharmazie, Dec. 1, 2003, 336(12), pp. 591-597.

International Preliminary Report on Patentability for PCT/US2011/058902, issued May 14, 2013.

Chemical Abstracts Service, Columbus, Ohio, US;1978, Ivashchenko, A.V. et al:"Synthesis and study of 2-(1-pyrazolyl)purine derivatives", XP002718743, retrieved from STN;

(56) References Cited

OTHER PUBLICATIONS

Database accession No. 1978:50805 abstract & Ivashchenko, A.V. et al: "Synthesis and study of 2-(1-pyrazolyl)purine derivatives" Khimiya Geterotsiklicheskikh Soedinenii, (10), 1404-6 CODEN: KGSSAQ; ISSN:0132-6244, 1977, Database CA [Online].
Chemical Abstracts Service, Columbus, Ohio, US ;1978, Ivashchenko, A.V. et al:"Synthesis and study of derivatives of 2-(1-pyrazolyl)pyrimidine", XP002718744, retrieved from STN; Database accession No. 1978:22825 abstract & Ivashchenko, A.V. et al: "Synthesis and studyof derivatives of 2-(1-pyrazolyl)pyrimidine" Khimiya Geterotsiklicheskikh Soedinenii, (9), 1255-7 CODEN: KGSSAQ; ISSN: 0132-6244, 1977.
King, Frank D., "Bioisosteres, Conformational Restriction, and Prodrugs Case History: An Example of a Conformational Restriction Approach", Med. Chem: Principle & Practice (1994), pp. 206-208.

* cited by examiner

SGC STIMULATORS

CROSS REFERENCE TO RELATED APPLICATIONS

This patent application is the U.S. national phase of international application, No. PCT/2011/058902, filed on Nov. 2, 2011, which claims the benefit of U.S. Provisional Application Nos. 61/411,730 filed Nov. 9, 2010 and 61/546,707 filed Oct. 11, 2011, the disclosure of which is hereby incorporated by reference.

FIELD OF THE INVENTION

The present disclosure relates to stimulators of soluble guanylate cyclase (sGC), pharmaceutical formulations thereof and methods of using the stimulators, alone or in combination with one or more additional agents, for treating and/or preventing various diseases, wherein an increase in the concentration of nitric oxide (NO) might be desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts GTP into the secondary messenger cyclic GMP (cGMP). The increased level of cGMP, in turn, modulates the activity of downstream effectors including protein kinases, phosphodiesterases (PDEs), and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure.

Experimental and clinical evidence indicates that reduced bioavailability and/or responsiveness to endogenously produced NO contributes to the development of cardiovascular, endothelial, renal and hepatic disease, as well as erectile dysfunction. In particular, the NO signaling pathway is altered in cardiovascular diseases, including, for instance, systemic and pulmonary hypertension, heart failure, stroke, thrombosis and atherosclerosis.

Pulmonary hypertension (PH) is a disease characterized by sustained elevation of blood pressure in the pulmonary vasculature (pulmonary artery, pulmonary vein and pulmonary capillaries), which results in right heart hypertrophy, eventually leading to right heart failure and death. In PH, the bioactivity of NO and other vasodilators such as prostacyclin is reduced, whereas the production of endogenous vasoconstrictors such as endothelin is increased, resulting in excessive pulmonary vasoconstriction. sGC stimulators have been used to treat PH because they promote smooth muscle relaxation, which leads to vasodilation.

Treatment with NO-independent sGC stimulators also promoted smooth muscle relaxation in the corpus cavernosum of healthy rabbits, rats and humans, causing penile erection, indicating that sGC stimulators are useful for treating erectile dysfunction.

NO-independent, heme-dependent, sGC stimulators, such as those disclosed herein, have several important differentiating characteristics, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed. These compounds have been shown to produce anti-aggregatory, anti-proliferative and vasodilatory effects.

Since compounds that stimulate sGC in an NO-independent manner offer considerable advantages over other current alternative therapies, there is a need to develop novel stimulators of sGC. They would be useful in the prevention, management and treatment of disorders such as pulmonary hypertension, arterial hypertension, heart failure, atherosclerosis, inflammation, thrombosis, renal fibrosis and failure, liver cirrhosis, erectile dysfunction and other cardiovascular disorders.

SUMMARY OF THE INVENTION

The present invention is directed to compounds according to Formula IA or IB, or a pharmaceutically acceptable salt thereof,

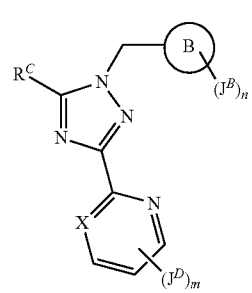

Formula IA

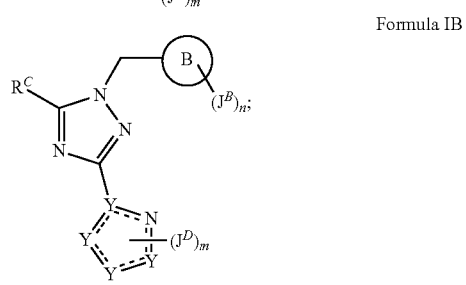

Formula IB wherein:
the symbol of the encircled letter B represents ring B, and ring B is a phenyl or a 6-membered heteroaryl ring, containing 1 or 2 nitrogen ring atoms;
n is an integer selected from 0 to 3;
each $J^B$ is independently selected from halogen, —CN, —$NO_2$, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^3$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);

X is selected from N or C;
each Y is independently selected from C, N, O or S;
m is an integer selected from 0 to 3;
each $J^D$ is a substituent on a carbon or nitrogen ring atom and is independently selected from halogen, $-NO_2$, $-OR^D$, $-SR^D$, $-C(O)R^D$, $-C(O)OR^D$, $-C(O)N(R^D)_2$, $-CN$, $-N(R^D)_2$, $-N(R^d)C(O)R^D$, $-N(R^d)C(O)OR^D$, $-SO_2R^D$, $-SO_2N(R^D)_2$, $-N(R^d)SO_2R^D$, a $C_{1-6}$ aliphatic, $-(C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;
each $R^D$ is independently selected from hydrogen, a $C_{1-6}$ aliphatic, $-(C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^5$;
each $R^d$ is independently selected from hydrogen, a $C_{1-6}$ aliphatic, $-(C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;
each $R^f$ is independently selected from a $C_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;
alternatively, two instances of $R^D$ linked to the same nitrogen atom of $J^D$, together with said nitrogen atom of $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$; or
alternatively, one instance of $R^D$ linked to a carbon, oxygen or sulfur atom of $J^D$ and one instance of $R^d$ linked to a nitrogen atom of the same $J^D$, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
each $R^5$ is independently selected from halogen, $-CN$, $-NO_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, $-OR^6$, $-SR^6$, $-COR^6$, $-C(O)OR^6$, $-C(O)N(R^6)_2$, $-N(R^6)C(O)R^6$, $-N(R^6)_2$, $-SO_2R^6$, $-SO_2N(R^6)_2$, $-N(R^6)SO_2R^6$, phenyl or an oxo group; wherein each said phenyl group is optionally and independently substituted with up to 3 instances of halogen, $-OH$, $-NH_2$, $-NH(C_{1-4}$ alkyl), $-N(C_{1-4}$ alkyl)$_2$, $-NO_2$, $-CN$, $C_{1-4}$ alkyl, $C_{1-4}$ haloalkyl, $-O(C_{1-4}$ alkyl) or $-O(C_{1-4}$ haloalkyl); and wherein each said $C_{7-12}$ aralkyl and each said cycloalkyl group is optionally and independently substituted with up to 3 instances of halogen;
each $R^6$ is independently selected from hydrogen, a $C_{1-4}$ alkyl, phenyl, a $C_{7-12}$ aralkyl or a $C_{3-8}$ cycloalkyl ring; wherein each of said $C_{1-4}$ alkyl, each said phenyl, each said $C_{7-12}$ aralkyl and each said cycloalkyl group is optionally and independently substituted with up to 3 instances of halogen;
alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or
alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;
or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, $-OH$, $-NH_2$, $-NH(C_{1-4}$ alkyl), $-N(C_{1-4}$ alkyl)$_2$, $-CN$, $C_{1-4}$ alkyl, $C_{1-4}$ haloalkyl, $-O(C_{1-4}$ alkyl), $-O(C_{1-4}$ haloalkyl) or oxo;
$R^C$ is selected a halogen, $-CN$, $C_{1-6}$ alkyl or a ring C;
ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;
each $J^C$ is independently selected from halogen, $-CN$, $-NO_2$, a $C_{1-6}$ aliphatic, $-OR^H$, $-SR^H$, $-N(R^H)_2$, a $C_{3-8}$ cycloaliphatic ring or a 4 to 8-membered heterocyclic ring;

wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^7$; or each $R^7$ is independently selected from halogen, —CN, —$NO_2$, $C_{1-4}$ alkyl, $C_{1-4}$ haloalkyl, $C_{3-8}$ cycloalkyl ring, —$OR^8$, —$SR^8$, —$N(R^8)_2$, or an oxo group; wherein each said cycloalkyl group is optionally and independently substituted with up to 3 instances of halogen;

each $R^8$ is independently selected from hydrogen, a $C_{1-4}$ alkyl, $C_{1-4}$ haloalkyl or a $C_{3-8}$ cycloalkyl ring; wherein each said cycloalkyl group is optionally and independently substituted with up to 3 instances of halogen;

alternatively, two instances of $R^8$ linked to the same nitrogen atom of $R^7$, together with said nitrogen atom of $R^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

$R^A$ is selected from hydrogen, halogen, $C_{1-4}$ alkyl or $C_{1-4}$ haloalkyl; provided that the compound is not one of the compounds represented below:

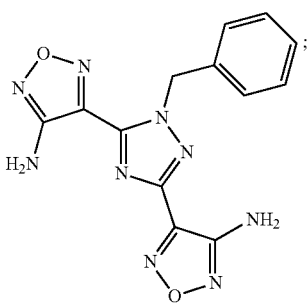

(CAS #799825-21-1)

-continued

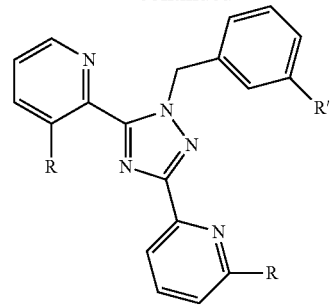

$R' = H$ and
- $R = H$ (CAS #150223-76-0)
- $R = —CN$ (CAS #150223-78-2)
- $R = —COOMe$ (CAS #189263-49-8)
- $R = —CH_2OH$ (CAS #189263-50-1)
- $R = —CH_2NH_2$ (CAS #150202-42-9)
- $R = —CH_2Br$ (CAS #189263-51-2)

$R' = —NO_2$ and
- $R = H$ (CAS #150223-82-8)
- $R = —CN$ (CAS #150223-84-0)
- $R = —CH_2NH_2$ (CAS #150202-43-0)

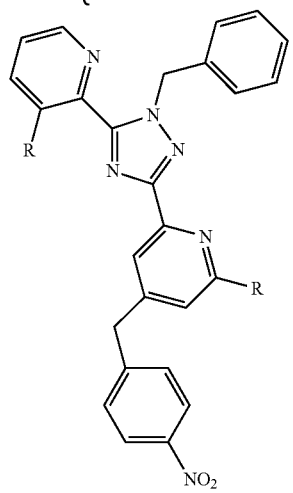

- $R = H$ (CAS #150223-91-9)
- $R = —CN$ (CAS #150223-95-3)
- $R = —CH2NH2$ (CAS #150223-97-5)

The invention also provides pharmaceutical compositions comprising a compound of Formula IA or Formula IB or a pharmaceutically acceptable salt thereof.

The invention also provides a method of treating or preventing a disease, health condition or disorder in a subject in need thereof, comprising administering, alone or in combination therapy, a therapeutically or prophylactically effective amount of the compound of Formula IA or Formula IB or a pharmaceutically acceptable salt thereof to the subject; wherein the disease, health condition or disorder is a peripheral or cardiac vascular disorder/condition, or a urogenital system disorder that can benefit from sGC stimulation.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

DEFINITIONS AND GENERAL TERMINOLOGY

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

As described herein, compounds of Formula IA or Formula IB may be optionally substituted with one or more substituents, such as illustrated generally below, or as exemplified by particular classes, subclasses, and species of the invention. The phrase "optionally substituted" is used interchangeably with the phrase "substituted or unsubstituted." In general, the term "substituted", refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. If a substituent radical or structure is not identified or defined as "optionally substituted", the substituent radical or structure is not substituted. As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound or chemically feasible compound is one that is not substantially altered when kept at a temperature of 25° C. or less, in the absence of moisture or other chemically reactive conditions, for at least a week.

A compound, such as the compounds of Formula IA or Formula IB or other compounds herein disclosed, may be present in its free form or as part of a co-form. The compound may be present in a solid form (e.g. an amorphous form, or a crystalline form or polymorph). Under certain conditions, compounds may also form salts. When one of the components in the co-form has clearly transferred a proton to the other component, the resulting co-form is referred to as a "salt". The formation of a salt is determined by how large the difference is in the pKas between the partners that form the mixture.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are within the scope of the disclosure.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like.

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, $sp^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term can be used in the phrase "aromatic carbocycle", and in this case it refers to an "aryl group" as defined below.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_3$-$C_{12}$ hydrocarbon or a bicyclic $C_7$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Heterocycle" (or "heterocyclyl" or "heterocyclic), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is on the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "aralkyl" refers to a radical having an aryl ring substituted with an alkylene group, wherein the open end of the alkylene group allows the aralkyl radical to bond to another part of the compound of Formula IA or Formula IB. The alkylene group is a bivalent, straight-chain or branched, saturated hydrocarbon group. As used herein, the term "$C_{7-12}$ aralkyl" means an aralkyl radical wherein the total number of carbon atoms in the aryl ring and the alkylene group combined is 7 to 12. Examples of "aralkyl" include, but not limited to, a phenyl ring substituted by a $C_{1-6}$ alkylene group, e.g., benzyl and phenylethyl, and a naphthyl group substituted by a $C_{1-2}$ alkylene group.

The term "heteroaryl" (or "heteroaromatic" or "heteroaryl group" or "aromatic heterocycle") used alone or as part of a larger moiety as in "heteroaralkyl" or "heteroarylalkoxy"

refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6, 5 heteroaromatic system, as used herein, for example, is a six membered heteroaromatic ring fused to a second five membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to an atom or a chain of atoms connecting two different parts of a molecule. The two atoms that are connected through the bridge (usually but not always, two tertiary carbon atoms) are referred to as "bridgeheads". In addition to the bridge, the two bridgeheads are connected by at least two of individual atoms or chains of atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0³,⁷]nonyl. "Spiro" bicyclic ring systems share only one ring atom (usually a quaternary carbon atom) between the two rings.

The term "ring atom" refers to an atom such as C, N, O or S that is part of the ring of an aromatic group, a cycloaliphatic group or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR⁺ (as in N-substituted pyrrolidinyl).

In some embodiments, two independent occurrences of a variable may be taken together with the atom(s) to which each variable is bound to form a 5-8-membered, heterocyclyl, aryl, or heteroaryl ring or a 3-8-membered cycloalkyl ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, carbocyclyl or aryl ring, wherein the group is attached to the rest of the molecule by a single point of attachment; and b) two independent occurrences of a substituent that are bound to different atoms and are taken together with both of those atoms to form a heterocyclyl, heteroaryl, carbocyclyl or aryl ring, wherein the ring that is formed has two points of attachment with the rest of the molecule. For example, where a phenyl group is substituted with two occurrences of R° as in Formula D1:

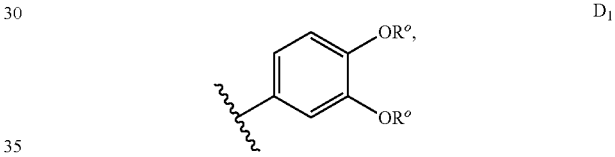

these two occurrences of R° are taken together with the oxygen atoms to which they are bound to form a fused 6-membered oxygen containing ring as in Formula D2:

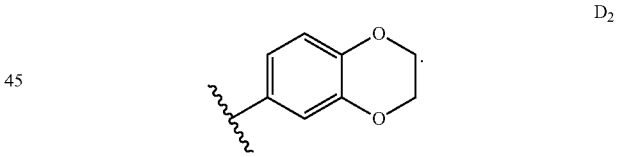

It will be appreciated that a variety of other rings can be formed when two independent occurrences of a substituent are taken together with the atom(s) to which each substituent is bound and that the examples detailed above are not intended to be limiting.

In some embodiments, an alkyl or aliphatic chain can be optionally interrupted with another atom or group. This means that a methylene unit of the alkyl or aliphatic chain can optionally be replaced with said other atom or group. Unless otherwise specified, the optional replacements form a chemically stable compound. Optional interruptions can occur both within the chain and/or at either end of the chain; i.e. both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to an H on the terminal end. For example, if —CH₂CH₂CH₃ were optionally interrupted with —O—, the resulting compound could be —OCH₂CH₃, —CH₂OCH₃, or —CH₂CH₂OH. In another example, if the divalent linker —CH₂CH₂CH₂— were optionally interrupted with —O—, the resulting compound could be —OCH₂CH₂—, —CH₂OCH₂—, or —CH₂CH₂O—. The optional replacements can also completely replace all of the carbon atoms in a chain. For example, a C₃ aliphatic can be optionally replaced by —N(R')—, —C(O)—, and —N(R')— to form —N(R')C(O)N(R')— (a urea).

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R^XO(O)C-alkyl is an example of a carboxy group used terminally. A group is internal when the group is present in the middle of a substituent at the end of the substituent bound to the rest of the chemical structure. Alkylcarboxy (e.g., alkyl-C(O)O— or alkyl-O(CO)—) and alkylcarboxyaryl (e.g., alkyl-C(O)O-aryl- or alkyl-O(CO)-aryl-) are examples of carboxy groups used internally.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

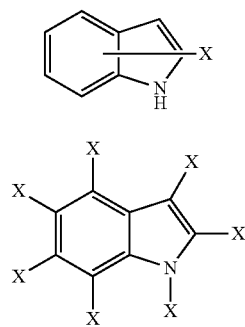

This also applies to multiple ring systems fused to optional ring systems (which would be represented by dotted lines). For example, in Formula D5, X is an optional substituent both for ring A and ring B.

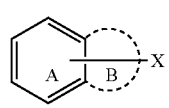

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

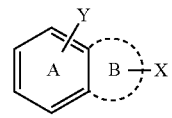

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

The terms C. "alkoxyalkyl", $C_{n-m}$ "alkoxyalkenyl", $C_{n-m}$ "alkoxyaliphatic", and $C_{n-m}$ "alkoxyalkoxy" mean alkyl, alkenyl, aliphatic or alkoxy, as the case may be, substituted with one or more alkoxy groups, wherein the combined total number of carbons of the alkyl and alkoxy groups, alkenyl and alkoxy groups, aliphatic and alkoxy groups or alkoxy and alkoxy groups, combined, as the case may be, is between the values of n and m. For example, a $C_{4-6}$ alkoxyalkyl has a total of 4-6 carbons divided between the alkyl and alkoxy portion; e.g. it can be —CH₂OCH₂CH₂CH₃, —CH₂CH₂OCH₂CH₃ or —CH₂CH₂CH₂OCH₃.

When the moieties described in the preceding paragraph are optionally substituted, they can be substituted in either or both of the portions on either side of the oxygen or sulfur. For example, an optionally substituted C₄ alkoxyalkyl could be, for instance, —CH₂CH₂OCH₂(Me)CH₃ or —CH₂(OH)OCH₂CH₂CH₃; a C₅ alkoxyalkenyl could be, for instance, —CH=CHO CH₂CH₂CH₃ or —CH=CHCH₂OCH₂CH₃.

The terms aryloxy, arylthio, benzyloxy or benzylthio, refer to an aryl or benzyl group attached to the molecule, or to another chain or ring, through an oxygen ("aryloxy", benzyloxy e.g., —O-Ph, —OCH₂Ph) or sulfur ("arylthio" e.g., —S-Ph, —S—CH₂Ph) atom. Further, the terms "aryloxyalkyl", "benzyloxyalkyl" "aryloxyalkenyl" and "aryloxyaliphatic" mean alkyl, alkenyl or aliphatic, as the case may be, substituted with one or more aryloxy or benzyloxy groups, as the case may be. In this case, the number of atoms for each aryl, aryloxy, alkyl, alkenyl or aliphatic will be indicated separately. Thus, a 5-6-membered aryloxy($C_{1-4}$alkyl) is a 5-6 membered aryl ring, attached via an oxygen atom to a $C_{1-4}$ alkyl chain which, in turn, is attached to the rest of the molecule via the terminal carbon of the $C_{1-4}$ alkyl chain.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH₂CHF₂ and a $C_{1-2}$ haloalkoxy could be —OC(Br)HCHF₂. This term includes perfluorinated alkyl groups, such as —CF₃ and —CF₂CF₃.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1-3}$ cyanoalkyl could be —C(CN)₂CH₂CH₃ and a $C_{1-2}$ cyanoalkenyl could be =CHC(CN)H₂.

As used herein, an "amino" group refers to —NH$_2$.

The terms "aminoalkyl", "aminoalkenyl", "aminoaliphatic", and "aminoalkoxy" mean alkyl, alkenyl, aliphatic or alkoxy, as the case may be, substituted with one or more amino groups. For example a C$_{1-3}$ aminoalkyl could be —CH(NH$_2$)CH$_2$CH$_2$NH$_2$ and a C$_{1-2}$ aminoalkoxy could be —OCH$_2$CH$_2$NH$_2$.

The term "hydroxyl" or "hydroxy" refers to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a C$_{1-3}$ hydroxyalkyl could be —CH$_2$(CH$_2$OH)CH$_3$ and a C$_4$ hydroxyalkoxy could be —OCH$_2$C(CH$_3$)(OH)CH$_3$.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$.

As used herein, in the context of resin chemistry (e.g. using solid resins or soluble resins or beads), the term "linker" refers to a bifunctional chemical moiety attaching a compound to a solid support or soluble support.

In all other situations, a "linker", as used herein, refers to a divalent group in which the two free valences are on different atoms (e.g. carbon or heteroatom) or are on the same atom but can be substituted by two different substituents. For example, a methylene group can be C$_1$ alkyl linker (—CH$_2$—) which can be substituted by two different groups, one for each of the free valences (e.g. as in Ph-CH$_2$-Ph, wherein methylene acts as a linker between two phenyl rings). Ethylene can be C$_2$ alkyl linker (—CH$_2$CH$_2$—) wherein the two free valences are on different atoms. The amide group, for example, can act as a linker when placed in an internal position of a chain (e.g. —CONH—). A linker can be the result of interrupting an aliphatic chain by certain functional groups or of replacing methylene units on said chain by said functional groups. E.g. a linker can be a C$_{1-6}$ aliphatic chain in which up to two methylene units are substituted by —C(O)— or —NH— (as in —CH$_2$—NH—CH$_2$—C(O)—CH$_2$— or —CH$_2$—NH—C(O)—CH$_2$—). An alternative way to define the same —CH$_2$—NH—CH$_2$—C(O)—CH$_2$— and —CH$_2$—NH—C(O)—CH$_2$— groups is as a C$_3$ alkyl chain optionally interrupted by up to two —C(O)— or —NH— moieties. Cyclic groups can also form linkers: e.g. a 1,6-cyclohexanediyl can be a linker between two R groups, as in

A linker can additionally be optionally substituted in any portion or position.

Divalent groups of the type R—CH= or R$_2$C=, wherein both free valences are in the same atom and are attached to the same substituent, are also possible. In this case, they will be referred to by their IUPAC accepted names. For instance an alkylidene (such as, for example, a methylidene (=CH$_2$) or an ethylidene (=CH—CH$_3$)) would not be encompassed by the definition of a linker in this disclosure.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W. et al., "Protective Groups in Organic Synthesis", Third Edition, John Wiley & Sons, New York: 1999, the entire contents of which is hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-ethyl-3-(3-dimethylaminopropyl)carbodiimide), DCC (dicyclohexylcarbodiimide), BOP (benzotriazol-1-yloxy-tris (dimethylamino)-phosphonium hexafluorophosphate), pyBOP ((benzotriazol-1-yloxy)tripyrrolidinophosphonium hexafluorophosphate), etc.

One of the aspects of the present invention is directed to a compound according to Formula IA or IB, or a pharmaceutically acceptable salt thereof,

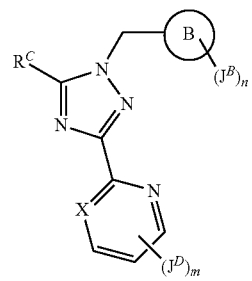

Formula IA

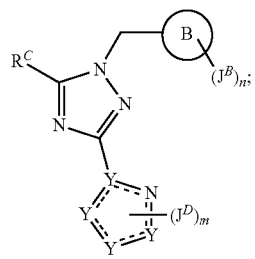

Formula IB wherein:
the symbol with the encircled letter B represents ring B, and ring B is a phenyl or a 6-membered heteroaryl ring, containing 1 or 2 nitrogen ring atoms;

n is an integer selected from 0 to 3;

each $J^B$ is independently selected from halogen, —CN, —NO$_2$, a C$_{1-6}$ aliphatic, —OR$^B$ or a C$_{3-8}$ cycloaliphatic group; wherein each said C$_{1-6}$ aliphatic and each said C$_{3-8}$ cycloaliphatic group is optionally and independently substituted with up to 3 instances of R$^3$;

each R$^B$ is independently selected from hydrogen, a C$_{1-6}$ aliphatic or a C$_{3-8}$ cycloaliphatic; wherein each said C$_{1-6}$ aliphatic and each said C$_{3-8}$ cycloaliphatic ring is optionally and independently substituted with up to 3 instances of R$^3$;

each R$^3$ is independently selected from halogen, —CN, C$_{1-4}$ alkyl, C$_{1-4}$ haloalkyl, —O(C$_{1-4}$ alkyl) or —O(C$_{1-4}$ haloalkyl);

X is selected from N or C;

each Y is independently selected from C, N, O or S;

m is an integer selected from 0 to 3;

each $J^D$ is a substituent on a carbon or nitrogen ring atom and is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a C$_{1-6}$ aliphatic, —(C$_{1-6}$ aliphatic)-R$^D$, a C$_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said C$_{1-6}$ aliphatic, each said C$_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of R$^5$;

each R$^D$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted with up to 3 instances of R$^5$;

each R$^d$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted by up to 3 instances of R$^5$;

each R$^f$ is independently selected from a C$_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted by up to 3 instances of R$^5$;

alternatively, two instances of R$^D$ linked to the same nitrogen atom of J$^D$, together with said nitrogen atom of J$^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^5$; or alternatively, one instance of R$^D$ linked to a carbon, oxygen or sulfur atom of J$^D$ and one instance of R$^d$ linked to a nitrogen atom of the same J$^D$, together with said carbon, oxygen or sulfur and said nitrogen atom of that same J$^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^5$;

each R$^5$ is independently selected from halogen, —CN, —NO$_2$, C$_{1-4}$ alkyl, a C$_{7-12}$ aralkyl, C$_{3-8}$ cycloalkyl ring, C$_{1-4}$ haloalkyl, C$_{1-4}$ cyanoalkyl, —OR$^6$, —SR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each R$^6$ is independently selected from hydrogen, a C$_{1-4}$ alkyl, phenyl, a C$_{7-12}$ aralkyl or a C$_{3-8}$ cycloalkyl ring; wherein each of said C$_{1-4}$ alkyl, each said phenyl, each said C$_{7-12}$ aralkyl and each said cycloalkyl group is optionally and independently substituted with up to 3 instances of halogen;

alternatively, two instances of R$^6$ linked to the same nitrogen atom of R$^5$, together with said nitrogen atom of R$^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of R$^6$ linked to a nitrogen atom of R$^5$ and one instance of R$^6$ linked to a carbon or sulfur atom of the same R$^5$, together with said nitrogen and said carbon or sulfur atom of the same R$^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two J$^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ alkyl)$_2$, —CN, C$_{1-4}$ alkyl, C$_{1-4}$ haloalkyl, —O(C$_{1-4}$ alkyl), —O(C$_{1-4}$ haloalkyl) or oxo;

R$^C$ is selected from halo, —CN, C$_{1-6}$ alkyl or a ring C; ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of J$^C$;

each J$^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of R$^7$; or alternatively, two J$^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each R$^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of R$^7$;

alternatively, two instances of R$^H$ linked to the same nitrogen atom of J$^C$, together with said nitrogen atom of J$^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^7$; or each R$^7$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each R$^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of R$^8$ linked to the same nitrogen atom of R$^7$, together with said nitrogen atom of R$^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; and R$^A$ is selected from hydrogen, halogen, C$_{1-4}$ alkyl or C$_{1-4}$ haloalkyl; provided that the compound is not one of the compounds represented below:

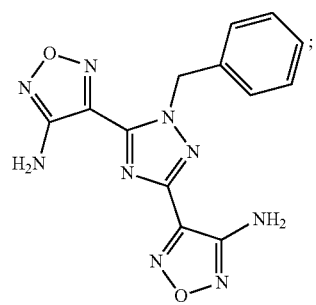

(CAS #799825-21-1)

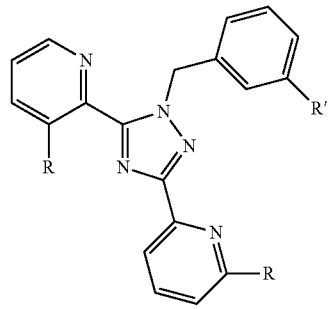

R' = H and
- R = H (CAS #150223-76-0)
- R = —CN (CAS #150223-78-2)
- R = —COOMe (CAS #189263-49-8)
- R = —CH$_2$OH (CAS #189263-50-1)
- R = —CH$_2$NH$_2$ (CAS #150202-42-9)
- R = —CH$_2$Br (CAS #189263-51-2)

R' = —NO$_2$ and
- R = H (CAS #150223-82-8)
- R = —CN (CAS #150223-84-0)
- R = —CH$_2$NH$_2$ (CAS #150202-43-0)

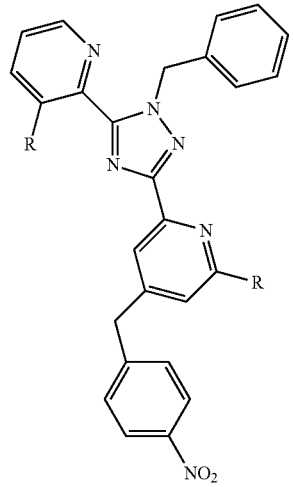

R = H (CAS #150223-91-9)
R = —CN (CAS #150223-95-3)
R = —CH2NH2 (CAS #150223-97-5)

In some of the embodiments of the compound of Formula IA or IB, or a pharmaceutically acceptable salt thereof, ring B is phenyl.

In some of the embodiments of Formula IA or IB, or a pharmaceutically acceptable salt thereof, n is an integer selected from 1 to 3, wherein each J$^B$ is independently selected from halogen, a C$_{1-6}$ aliphatic or —OR$^B$. In further embodiments, each J$^B$ is independently selected from halogen atoms. In still further embodiments, each $J^B$ is independently selected from fluoro or chloro. In yet further embodiments, each $J^B$ is fluoro.

In some of the embodiments of Formula IA or IB, or a pharmaceutically acceptable salt thereof, n is an integer selected from 1 to 3, and each $J^B$ is a $C_{1-6}$ aliphatic. In further embodiments, each $J^B$ is methyl or ethyl.

In some of the embodiments of Formula IA or IB, or a pharmaceutically acceptable salt thereof, n is 1. In further embodiments, $J^B$ is selected from halogen atoms. In still further embodiments, $J^B$ is fluoro or chloro. In yet further embodiments, $J^B$ is fluoro.

In some of the embodiments of Formula IA or IB, or a pharmaceutically acceptable salt thereof, n is an integer selected from 1 to 3, and each $J^B$ is independently selected from halogen, a $C_{1-6}$ aliphatic or —$OR^B$. In further embodiments, at least one $J^B$ is ortho to the attachment of the methylene linker between ring B and the triazolyl ring. In still further embodiments, each $J^B$ is independently selected from halogen atoms. In yet further embodiments, each $J^B$ is independently selected from fluoro or chloro. In yet still further embodiments, each $J^B$ is fluoro.

In some of the embodiments of Formula IA or IB, or a pharmaceutically acceptable salt thereof, n is 1, and each $J^B$ is independently selected from halogen, a $C_{1-6}$ aliphatic or —$OR^B$, wherein at least one of the $J^B$ groups is ortho to the attachment of the methylene linker between ring B and the triazolyl ring is fluoro.

In some of the embodiments of Formula IA or IB, or a pharmaceutically acceptable salt thereof, ring B is a 6-membered heteroaryl ring.

In some of the embodiments of Formula IA or IB, or a pharmaceutically acceptable salt thereof, ring B is a pyridyl or pyrimidinyl ring.

In some of the embodiments of Formula IA, or a pharmaceutically acceptable salt thereof, X in ring D of Formula AI is a ring carbon atom and it is optionally substituted. In further embodiments, ring B is a phenyl ring or 6-membered heteroaryl ring. In still further embodiments, ring B is phenyl. Alternatively, in some of the embodiments, ring B is pyridyl or pyrimidinyl ring.

In some of the embodiments of Formula IA, or a pharmaceutically acceptable salt thereof, X in ring D of Formula AI is a ring nitrogen atom.

In some of the embodiments of Formula IB, or a pharmaceutically acceptable salt thereof, one of the 4 instances of Y in ring D is selected from N, O or S and the other 3 instances of Y in ring D are carbon atoms, wherein said carbon atoms are optionally substituted.

In some of the embodiments of the compounds of Formula IB, or a pharmaceutically acceptable salt thereof, ring D is a thiazolyl or oxazolyl ring such as thiazol-2-yl, thiazol-4-yl, oxazol-2-yl or oxazol-4-yl ring. In further embodiments of the compounds of Formula IB, $R^C$ is ring C, and ring C is a pyridyl, pyrimidinyl, oxazolyl or thiazol ring.

In some of the embodiments of Formula IA or IB, or a pharmaceutically acceptable salt thereof, m is 0.

In some of the embodiments of Formula IA or IB, or a pharmaceutically acceptable salt thereof, m is an integer selected from 1, 2 or 3 and each $J^D$ is independently selected from halogen, a $C_{1-6}$ aliphatic, —$N(R^D)_2$, —$N(R^d)C(O)R^D$, —$N(R^d)C(O)OR^D$, —$SO_2R^D$, —$SO_2N(R^D)_2$, —$N(R^d)SO_2R^D$, —$SR^D$, —$OR^D$ or an optionally substituted $C_{3-8}$ cycloaliphatic ring. In further embodiments, each $J^D$ is independently selected from halogen atoms. In still further embodiments, each $J^D$ is independently selected from a chloro or fluoro.

In some of the embodiments of Formula IA or IB, or a pharmaceutically acceptable salt thereof, m is an integer selected from 1, 2 or 3 and each $J^D$ is independently selected from a $C_{1-6}$ aliphatic or a $C_{3-8}$ cycloaliphatic ring. In further embodiments, each $J^D$ is independently methyl, ethyl, propyl, cyclobutyl, cyclopropyl or isopropyl. In still further embodiments, each $J^D$ is independently methyl, ethyl or cyclopropyl.

In some of the embodiments of Formula IA or IB, or a pharmaceutically acceptable salt thereof, m is an integer selected from 1, 2 or 3 and each $J^D$ is independently selected from —$N(R^D)_2$, —$N(R^d)C(O)R^D$, —$N(R^d)C(O)OR^D$, —$SO_2R^D$, —$SO_2N(R^D)_2$, —$N(R^d)SO_2R^D$ or —$OR^D$. In further embodiments, each $R^d$ is independently selected from a $C_{1-4}$ alkyl or hydrogen and each $R^D$ is independently selected from hydrogen or $C_{1-4}$ alkyl. In still further embodiments, each $R^d$ is independently selected from hydrogen or methyl, and each $R^D$ is independently selected from hydrogen, methyl, ethyl, propyl or isopropyl. In yet further embodiments, each $R^d$ and each $R^D$ is independently selected from hydrogen or methyl.

In some of the embodiments of Formula IA or IB, or a pharmaceutically acceptable salt thereof, m is an integer selected from 1, 2 or 3 and each $J^D$ is independently selected from methyl, fluoro, —$N(R^D)_2$, —$N(R^d)C(O)RD$, —$N(R^d)C(O)OR^D$, —$SO_2R^D$, —$SO_2N(R^D)_2$ or —$N(R^d)SO_2R^D$; wherein each $R^d$ and each $R^D$ is independently selected from hydrogen or methyl. In further embodiments, $R^C$ is —CN or halo. Alternatively, $R^C$ is a $C_{1-6}$ alkyl. In other alternative embodiments, $R^C$ is ring C. In some of the alternative embodiments, $R^C$ is ring C, wherein ring C is a phenyl ring, a monocyclic 5 or 6-membered heteroaryl ring, a monocyclic 3 to 10-membered cycloaliphatic ring or a monocyclic 4 to 10-membered heterocycle; each of the phenyl ring, a monocyclic 5 or 6-membered heteroaryl ring, a monocyclic 3 to 10-membered cycloaliphatic ring or a monocyclic 4 to 10-membered heterocycle is optionally and independently substituted with up to 6 instances of $J^C$.

In some of the embodiments of Formula IA or IB, or a pharmaceutically acceptable salt thereof, $R^C$ is —CN or halo.

In some of the embodiments of Formula IA or IB, or a pharmaceutically acceptable salt thereof, $R^C$ is a $C_{1-6}$ alkyl. In further embodiments, $R^C$ is selected from methyl, ethyl, propyl, isopropyl or butyl.

In some of the embodiments of Formula IA or IB, or a pharmaceutically acceptable salt thereof, $R^C$ is a ring C. In further embodiments, ring C is a phenyl ring, a monocyclic 5 or 6-membered heteroaryl ring, a monocyclic 3 to 10-membered cycloaliphatic ring or a monocyclic 4 to 10-membered heterocycle; each of the phenyl ring, a monocyclic 5 or 6-membered heteroaryl ring, a monocyclic 3 to 10-membered cycloaliphatic ring or a monocyclic 4 to 10-membered heterocycle is optionally and independently substituted with up to 6 instances of $J^C$. In still further embodiments, ring C is a phenyl, a monocyclic 5 or 6-membered heteroaryl ring, a monocyclic 3 to 6-membered cycloaliphatic ring or a monocyclic 4 to 6-membered heterocycle; each of them optionally and independently substituted with up to 3 instances of $J^C$.

In some of the embodiments of Formula IA or IB, or a pharmaceutically acceptable salt thereof, $R^C$ is a ring C, wherein ring C is a monocyclic 3 to 6-membered cycloaliphatic ring, optionally substituted with up to 2 instances of $J^C$. In further embodiments, ring C is cyclopropyl, cyclobutyl, cyclopentyl or cyclohexyl.

In some of the embodiments of Formula IA or IB, or a pharmaceutically acceptable salt thereof, $R^C$ is a ring C, wherein ring C is a 4-membered cycloaliphatic ring substituted by 1 to 3 instances of $J^C$, a 5-membered cycloaliphatic ring substituted by 1 to 4 instances of $J^C$ or a 6-membered cycloaliphatic ring substituted by 1 to 5 instances of $J^C$, and wherein each $J^C$ is independently selected from halogen or $C_{1-6}$ aliphatic.

In some of the embodiments of Formula IA or IB, or a pharmaceutically acceptable salt thereof, $R^C$ is a ring C, wherein ring C is phenyl, optionally and independently substituted by up to 5 instances of $J^C$. In further embodiments, $R^C$ is ring C and ring C is unsubstituted phenyl.

In some of the embodiments of Formula IA or IB, or a pharmaceutically acceptable salt thereof, $R^C$ is ring C and ring C is substituted phenyl. In further embodiments, ring C is substituted by 1 to 3 instances of $J^C$ and wherein each $J^C$ is independently selected from halogen, $C_{1-6}$ aliphatic, —$NH_2$, —CN or —O($C_{1-6}$ aliphatic). In still further embodiments, each $J^C$ is independently selected from halogen, $C_{1-4}$ alkyl, —O($C_{1-4}$ alkyl), —CN or —$NH_2$. In yet further embodiments, ring C is phenyl substituted by 1 to 2 instances of $J^C$. In yet still further embodiments, each $J^C$ is independently selected from fluoro, methyl, —CN or —$OCH_3$.

In some of the embodiments of Formula IA or IB, or a pharmaceutically acceptable salt thereof, $R^C$ is ring C, wherein ring C is a 5 to 6-membered heteroaryl ring, optionally substituted by up to 5 instances of $J^C$.

In some of the embodiments of Formula IA or IB, or a pharmaceutically acceptable salt thereof, $R^C$ is ring C, wherein ring C is an unsubstituted 5 to 6-membered heteroaryl ring. In further embodiments, the 5 to 6-membered heteroaryl ring as ring C is selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl. In still further embodiments, the 5 to 6-membered heteroaryl ring as ring C is selected from furanyl, thienyl, thiazolyl, oxazolyl,1,3,4-oxadiazolyl, pyridinyl, pyrimidinyl or pyrazin-3-yl. In yet further embodiments, the 5 to 6-membered heteroaryl ring as ring C is selected from thienyl, thiazolyl, oxazoly, 1,3,4-oxadiazolyl or pyridinyl. In yet still further embodiments, the 5 to 6-membered heteroaryl ring as ring C is selected from furan-2-yl, furan-3-yl, thien-3-yl, thien-2-yl, thiazol-2-yl, thiazol-4-yl, oxazol-2-yl, oxazol-4-yl, pyridin-2-yl, pyridin-3-yl, pyridin-4-yl, pyrimidin-2-yl or pyrimidin-4-yl.

In some of the embodiments of Formula IA or IB, or a pharmaceutically acceptable salt thereof, $R^C$ is ring C, wherein ring C is a 5 to 6-membered heteroaryl ring substituted by up to 5 instances of $J^C$. In further embodiments, the 5 to 6-membered heteroaryl ring as ring C is selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl. In still further embodiments, the 5 to 6-membered heteroaryl ring as ring C is selected from furanyl, thienyl, thiazolyl, oxazolyl, 1,3,4-oxadiazolyl, pyridinyl, pyrimidinyl or pyrazin-3-yl. In yet further embodiments, the 5 to 6-membered heteroaryl ring as ring C is selected from thienyl, thiazolyl, oxazolyl, 1,3,4-oxadiazolyl or pyridinyl. In yet still further embodiments, the 5 to 6-membered heteroaryl ring as ring C is selected from furan-2-yl, furan-3-yl, thien-3-yl, thien-2-yl, thiazol-2-yl, thiazol-4-yl, oxazol-2-yl, oxazol-4-yl, pyridin-2-yl, pyridin-3-yl, pyridin-4-yl, pyrimidin-2-yl or pyrimidin-4-yl; and is independently substituted with up to 2 instances of $J^C$. In some of the embodiments, each $J^C$ is independently selected from halogen, $C_{1-6}$ aliphatic, —CN, —$NH_2$ or —O($C_{1-6}$ aliphatic).

In some of the embodiments of Formula IA or IB, or a pharmaceutically acceptable salt thereof, $R^C$ is ring C, wherein ring C is thienyl or pyridinyl substituted by 1 to 3 instances of $J^C$ and each $J^C$ is independently selected from a halogen, $C_{1-6}$ aliphatic, —$NH_2$ or —O($C_{1-6}$ aliphatic). In further embodiments, each $J^C$ is independently selected from $C_{1-6}$ aliphatic. In still further embodiments, each $J^C$ is independently selected from methyl, ethyl, propyl or isopropyl. In yet further embodiments, each $J^C$ is independently selected from a halogen atom, methyl, —$NH_2$ or —$OCH_3$.

In some of the embodiments of Formula IA or IB, or a pharmaceutically acceptable salt thereof, RC is ring C, wherein ring C is a bicyclic 7 to 10-membered heteroaryl ring. In further embodiments, ring C is benzofuran-2-yl, furo[3,2-b]pyridinyl, furo[2,3-b]pyridinyl, benzothienyl or indolyl. In still further embodiments, ring C is benzofuran-2-yl, furo[3,2-b]pyridinyl or benzothienyl.

In some of the embodiments, the invention is directed to the compound having Formula IA, or a pharmaceutically acceptable salt thereof.

In some of the embodiments of the compound of Formula IA, or a pharmaceutically acceptable salt thereof, the compound has Formula IIA,

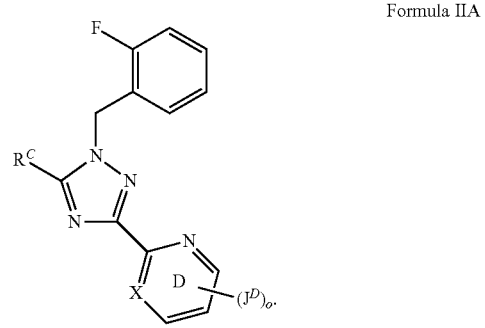

Formula IIA

In some of the embodiments of the compound of Formula IA, or a pharmaceutically acceptable salt thereof, the compound has Formula III or Formula IV:

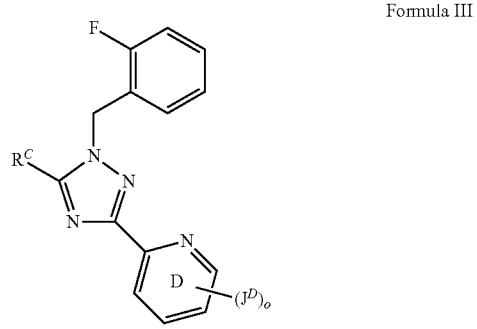

Formula III

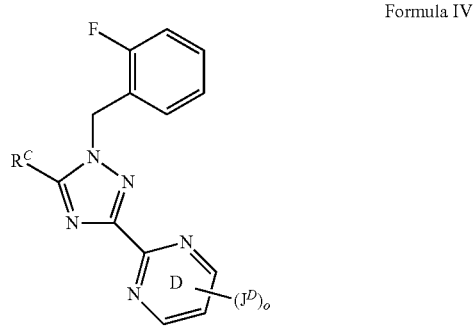

Formula IV

In further embodiments, the compound has one of Formulae VA, VC, VD and VF:

VA
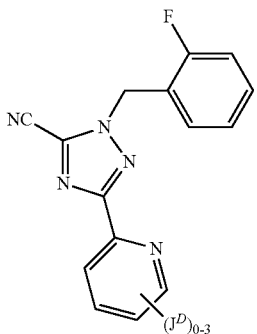

VC
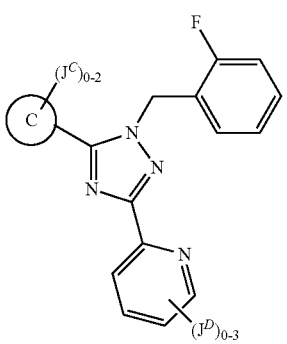

VD
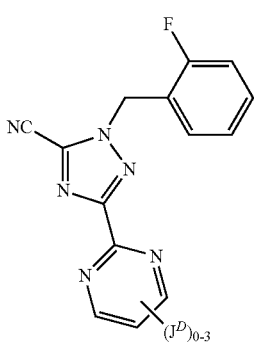

VF
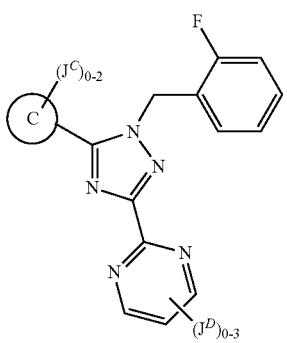

In some of the embodiments, the invention is directed to the compound of Formula IB, or a pharmaceutically acceptable salt thereof. In further embodiments, the compound has Formula IIB:

Formula IIB
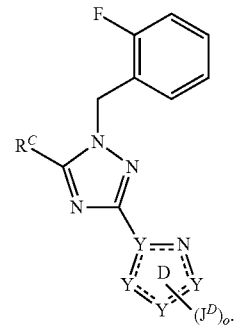

In some of the embodiments of the compound of Formula IIB, $R^C$ is halo, —CN or —$C_{1-6}$ alkyl.

In some of the embodiments of the compound of Formula IIB, $R^C$ is —CN and the compound is represented by Formula VI:

Formula VI
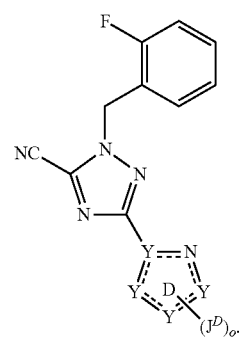

In some of the embodiments of the compound of Formula IIB, $R^C$ is ring C and the compound is represented by Formula VII:

Formula VII
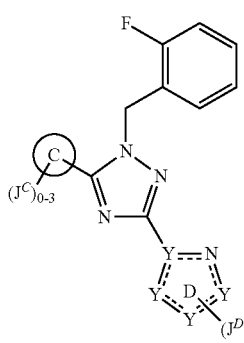

wherein the symbol of the encircled letter C represents ring C. In further embodiments, ring C is selected from a phenyl ring, a monocyclic 5 or 6-membered heteroaryl ring, a monocyclic 3 to 10-membered cycloaliphatic ring, or a monocyclic 4, 5 or 6-membered heterocycle; wherein each of said phenyl ring, monocyclic 5 or 6-membered heteroaryl ring, monocyclic 3 to 8-membered cycloaliphatic ring, or monocyclic 4, 5 or 6-membered heterocycle is optionally and independently substituted with up to 3 instances of $J^C$. In still further embodiments, ring C is selected from a phenyl ring, cyclopropyl ring, cyclobutyl ring, azetidinyl ring, thiazolyl ring or oxazolyl ring. In yet further embodiments, ring C is a thiazolyl ring or oxazolyl ring, e.g., thiazol-2-yl ring, thiazol-4-yl ring, oxazol-2-yl ring and oxazol-4-yl ring. In yet still further embodiments, ring C is a thiazol-2-yl ring or thiazol-4-yl ring.

In some embodiments, compounds of Formula IA and Formula IB are selected from those listed in Tables 1a and 1b herein.

TABLE 1b

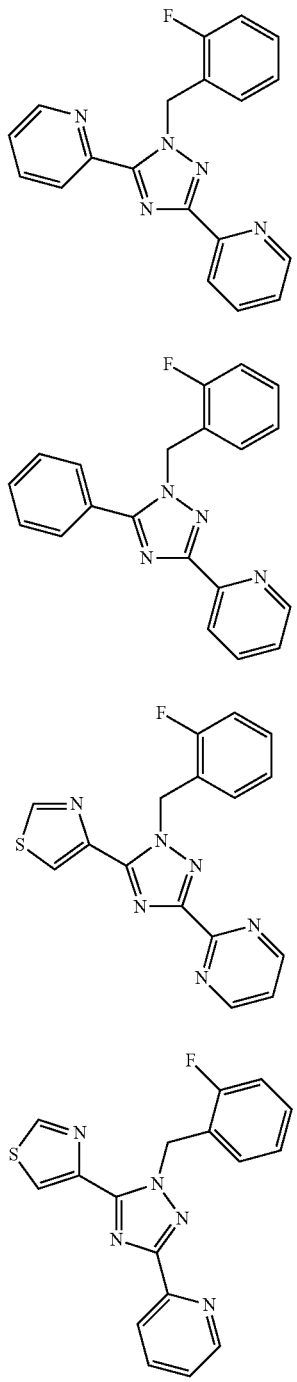

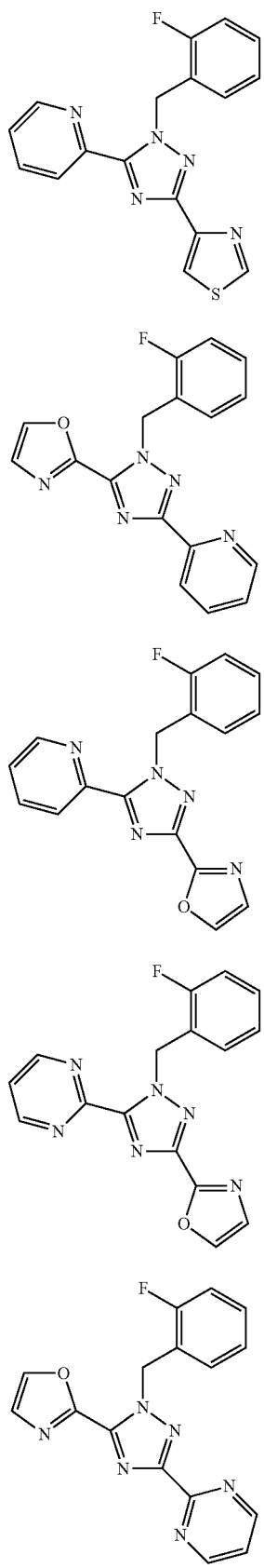

TABLE 1b-continued
| | |
|---|---|
| 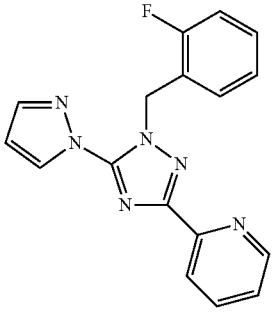 [SMILES: Fc1ccccc1Cn1nc(-c2ccccn2)nc1-n1cccn1] | I-10 |
| 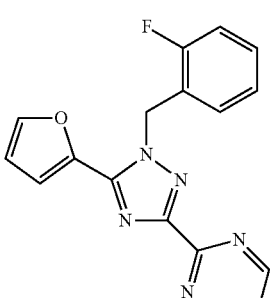 | I-11 |
| 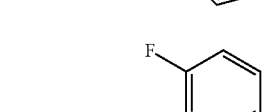 | I-12 |
| 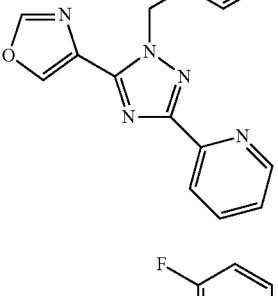 | I-13 |
| 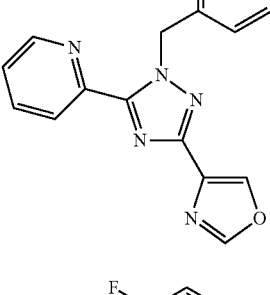 | I-14 |
TABLE 1b-continued
| | |
|---|---|
| 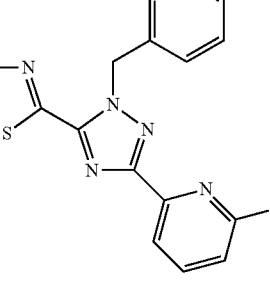 | I-15 |
|  | I-16 |
| 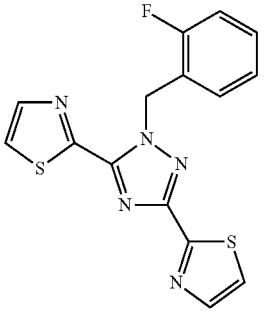 [SMILES: Fc1ccccc1Cn1nc(-c2nccs2)nc1-c1nccs1] | I-17 |
| 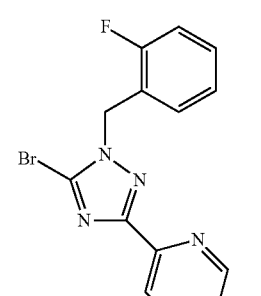 | I-18 |
| 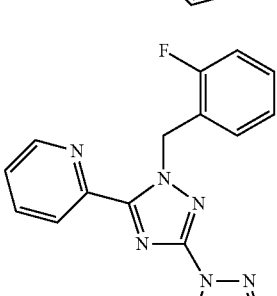 | I-19 |

TABLE 1b-continued
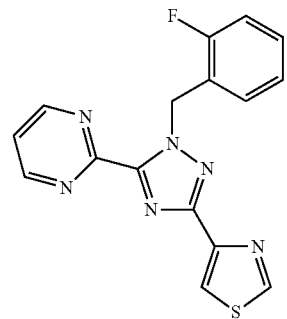 [SMILES: Fc1ccccc1Cn1nc(-c2cscn2)nc1-c1ncccn1] I-20
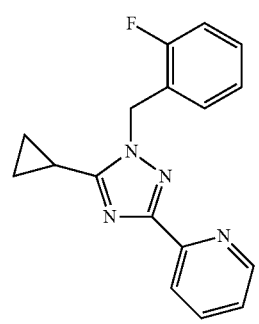 [SMILES: Fc1ccccc1Cn1nc(-c2ccccn2)nc1C1CC1] I-21
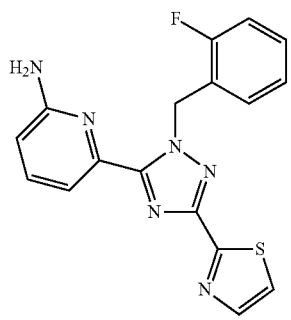 [SMILES: Nc1cccc(-c2nc(-c3nccs3)nn2Cc2ccccc2F)n1] I-22
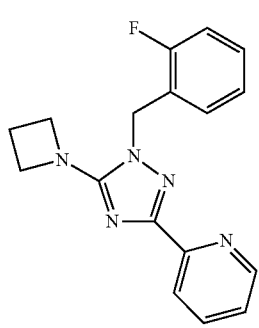 [SMILES: Fc1ccccc1Cn1nc(-c2ccccn2)nc1N1CCC1] I-23
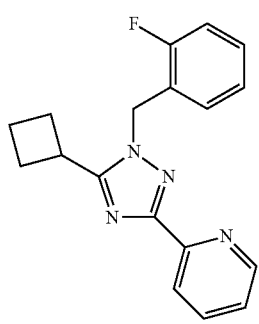 [SMILES: Fc1ccccc1Cn1nc(-c2ccccn2)nc1C1CCC1] I-24
TABLE 1b-continued
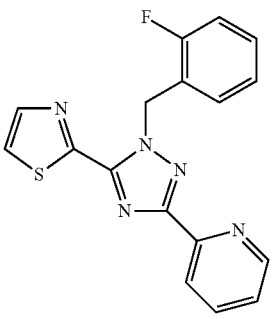 [SMILES: Fc1ccccc1Cn1nc(-c2ccccn2)nc1-c1nccs1] I-25
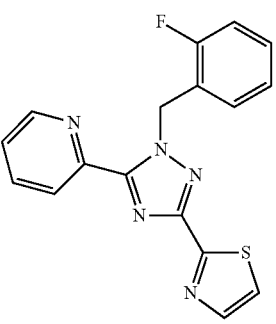 [SMILES: Fc1ccccc1Cn1nc(-c2nccs2)nc1-c1ccccn1] I-26
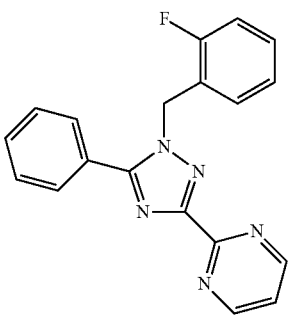 [SMILES: Fc1ccccc1Cn1nc(-c2ncccn2)nc1-c1ccccc1] I-27
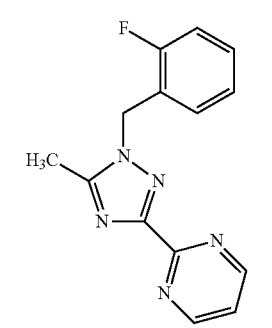 [SMILES: Cc1nc(-c2ncccn2)nn1Cc1ccccc1F] I-28
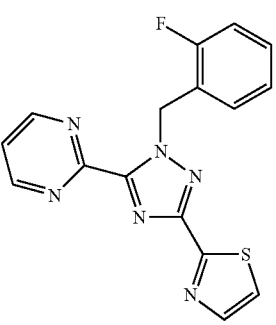 [SMILES: Fc1ccccc1Cn1nc(-c2nccs2)nc1-c1ncccn1] I-29

TABLE 1b-continued
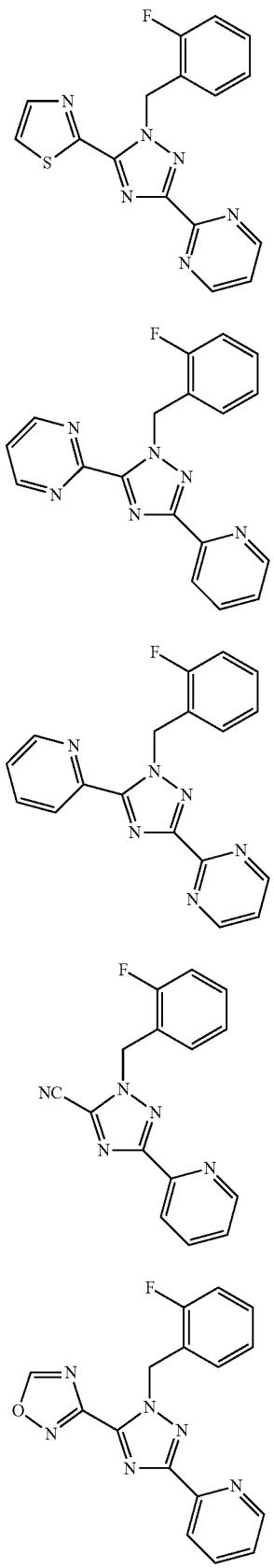
I-30
I-31
I-32
I-33
I-34
TABLE 1b
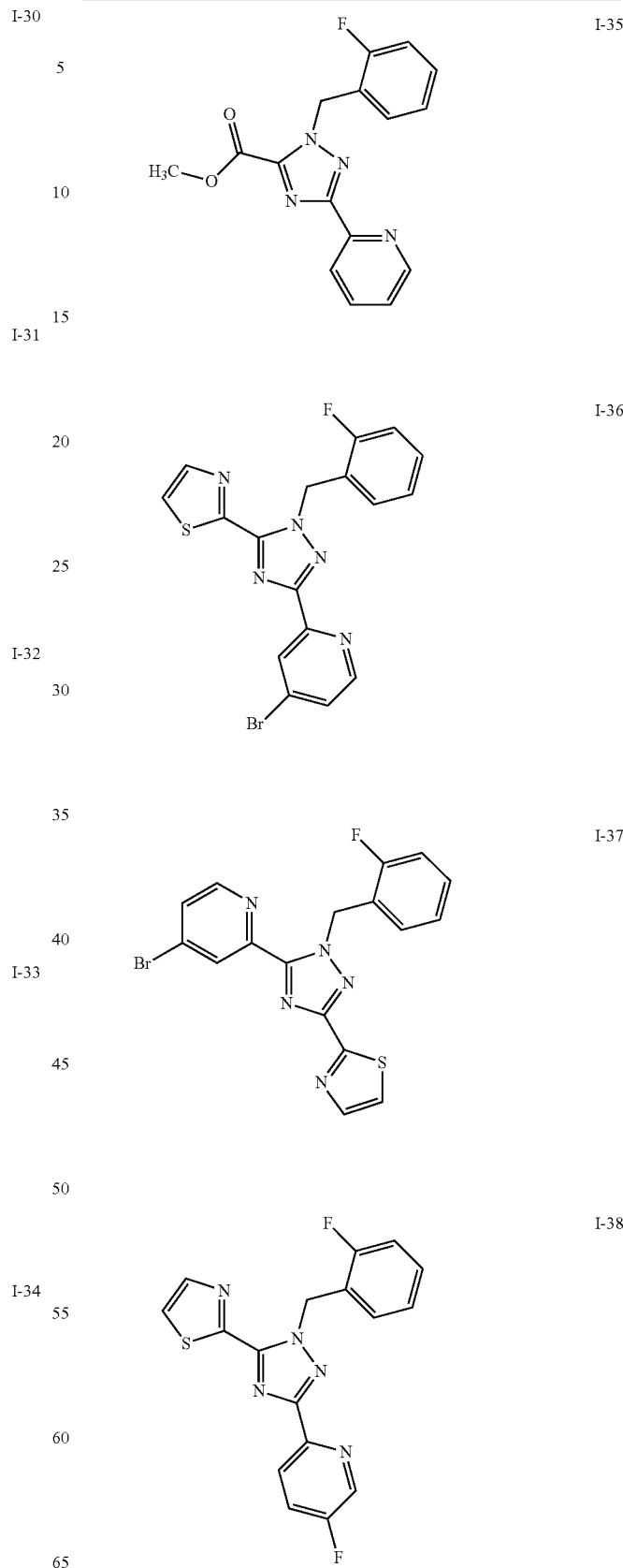
I-35
I-36
I-37
I-38

TABLE 1b-continued
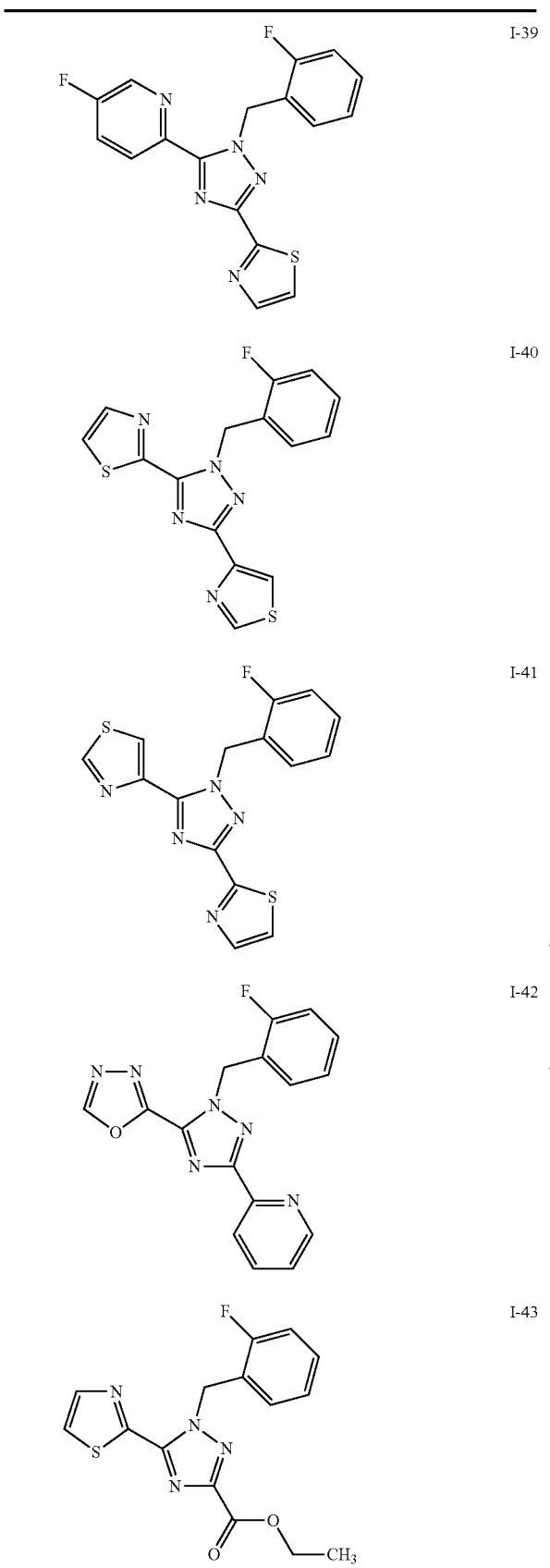
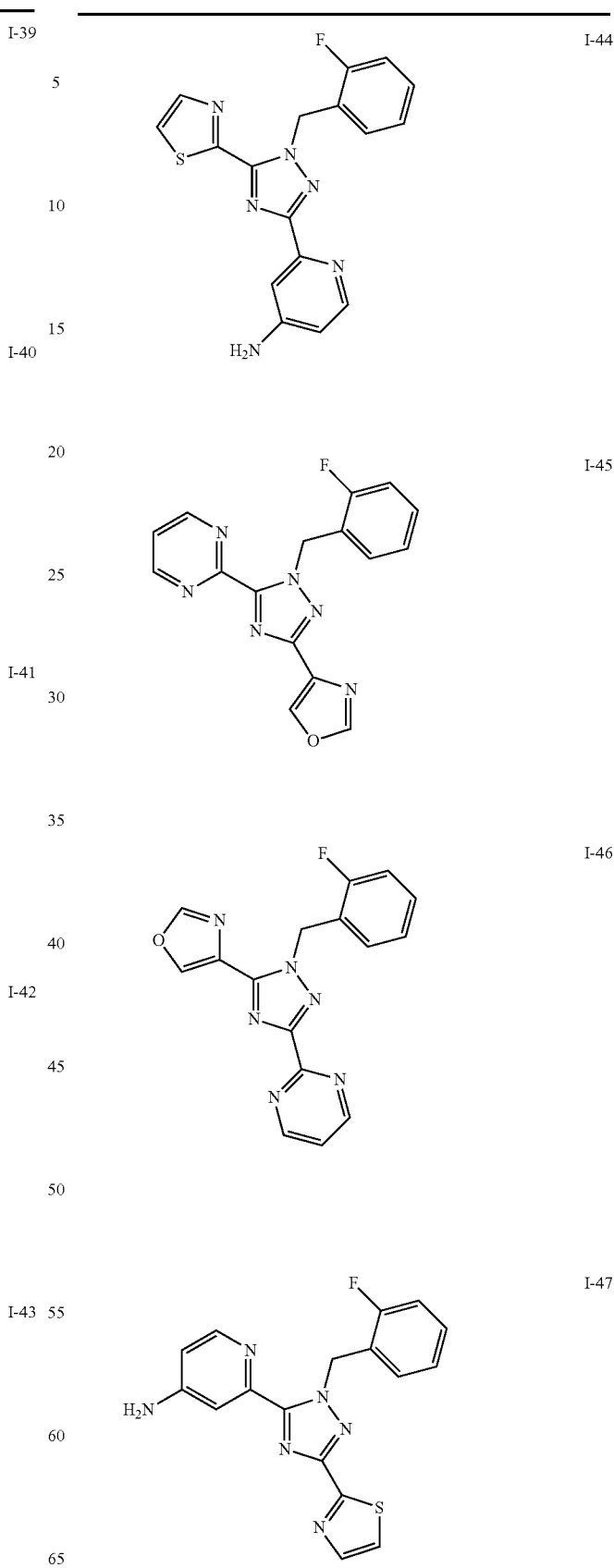

TABLE 1b-continued
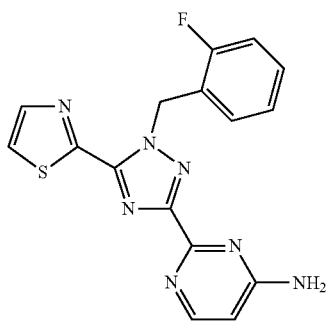 [SMILES: Nc1ccnc(-c2nc(-c3nccs3)n(Cc3ccccc3F)n2)n1] I-48
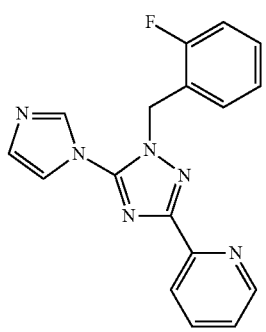 [SMILES: Fc1ccccc1Cn1nc(-c2ccccn2)nc1-n1ccnc1] I-49
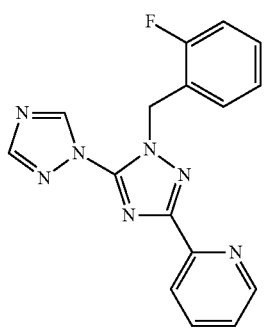 [SMILES: Fc1ccccc1Cn1nc(-c2ccccn2)nc1-n1cncn1] I-50
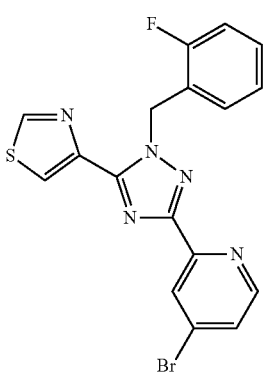 [SMILES: Fc1ccccc1Cn1nc(-c2cc(Br)ccn2)nc1-c1cscn1] I-51
TABLE 1b-continued
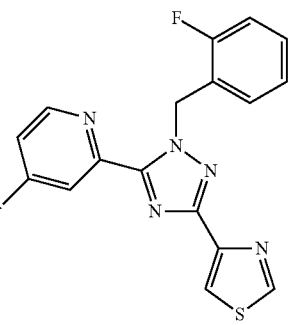 I-52
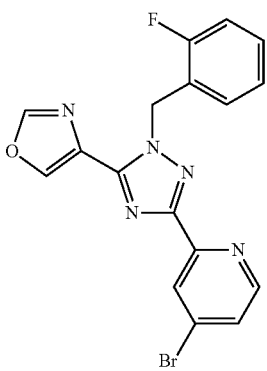 [SMILES: Fc1ccccc1Cn1nc(-c2cc(Br)ccn2)nc1-c1cocn1] I-53
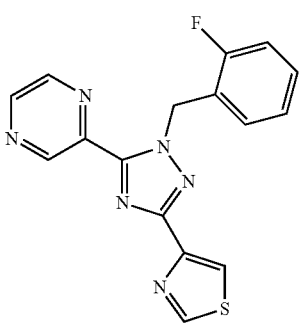 [SMILES: Fc1ccccc1Cn1nc(-c2cscn2)nc1-c1cnccn1] I-54
I-55

TABLE 1b-continued
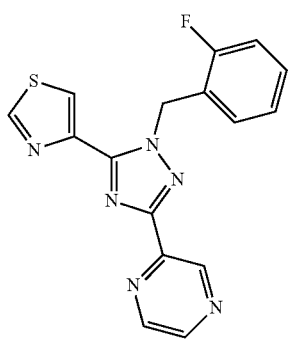 [SMILES: Fc1ccccc1Cn1nc(-c2cnccn2)nc1-c1cscn1]
I-56
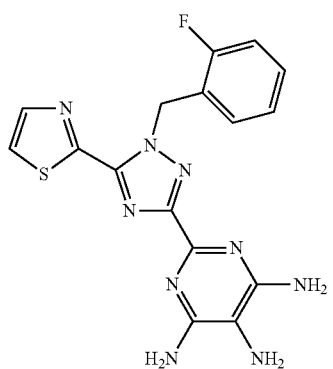 [SMILES: Nc1nc(-c2nc(-c3nccs3)n(Cc3ccccc3F)n2)nc(N)c1N]
I-57
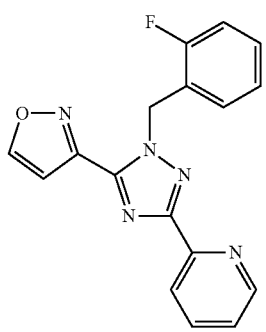 [SMILES: Fc1ccccc1Cn1nc(-c2ccccn2)nc1-c1ccon1]
I-58
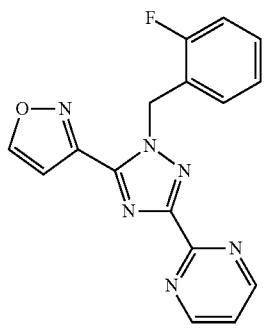 [SMILES: Fc1ccccc1Cn1nc(-c2ncccn2)nc1-c1ccon1]
I-59
TABLE 1b-continued
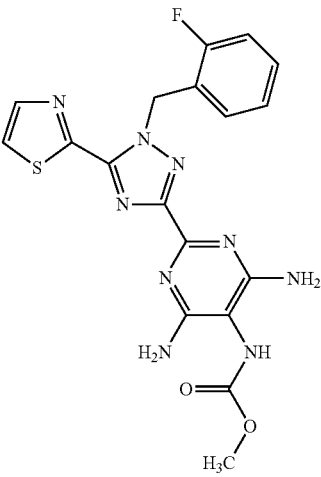 [SMILES: COC(=O)Nc1c(N)nc(-c2nc(-c3nccs3)n(Cc3ccccc3F)n2)nc1N]
I-60
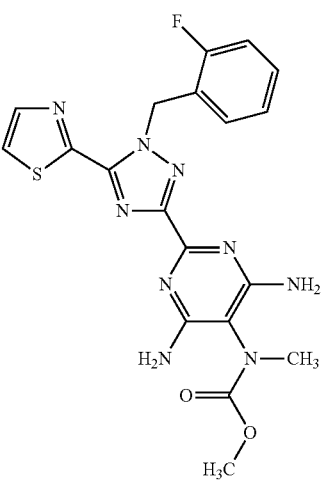 [SMILES: COC(=O)N(C)c1c(N)nc(-c2nc(-c3nccs3)n(Cc3ccccc3F)n2)nc1N]
I-61
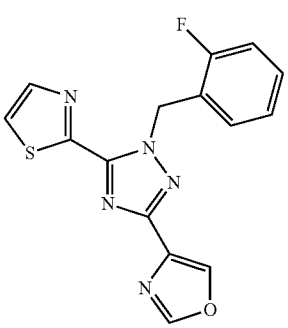 [SMILES: Fc1ccccc1Cn1nc(-c2cocn2)nc1-c1nccs1]
I-62
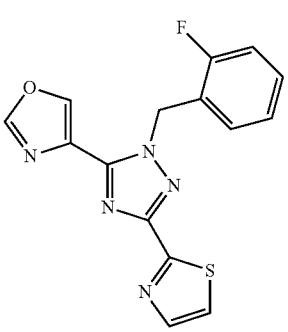 [SMILES: Fc1ccccc1Cn1nc(-c2nccs2)nc1-c1cocn1]
I-63

TABLE 1b-continued

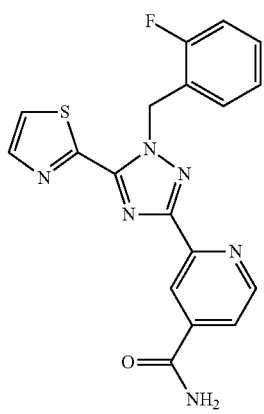 [SMILES: NC(=O)c1ccnc(-c2nc(-c3nccs3)n(Cc3ccccc3F)n2)c1]
I-64

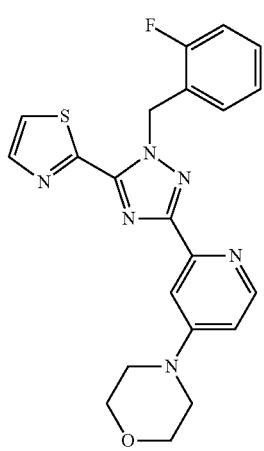 [SMILES: Fc1ccccc1Cn1nc(-c2cc(N3CCOCC3)ccn2)nc1-c1nccs1]
I-65

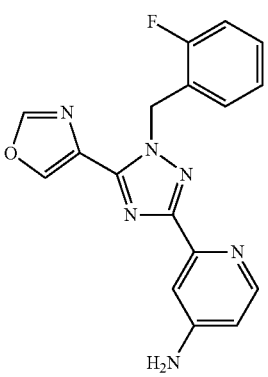 [SMILES: Nc1ccnc(-c2nc(-c3cocn3)n(Cc3ccccc3F)n2)c1]
I-66

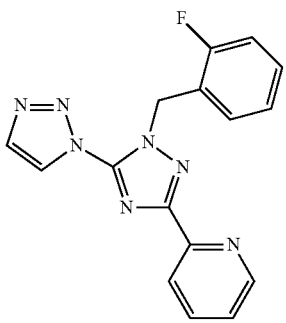 [SMILES: Fc1ccccc1Cn1nc(-c2ccccn2)nc1-n1ccnn1]
I-67A

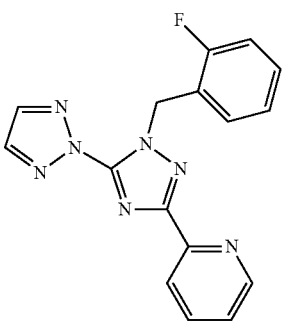 [SMILES: Fc1ccccc1Cn1nc(-c2ccccn2)nc1-n1nccn1]
I-67B

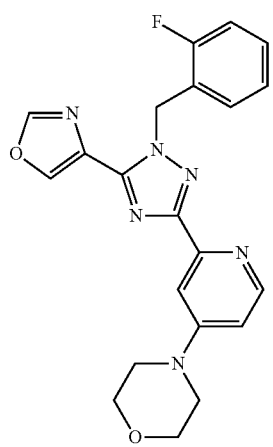 [SMILES: Fc1ccccc1Cn1nc(-c2cc(N3CCOCC3)ccn2)nc1-c1cocn1]
I-68

Methods of Preparing the Compounds

The compounds of Formula IA or Formula IB may be prepared according to the schemes and examples depicted and described below. Unless otherwise specified, the starting materials and various intermediates may be obtained from commercial sources, prepared from commercially available compounds or prepared using well-known synthetic methods. Another aspect of the present invention is a process for preparing the compounds of Formula IA or Formula IB as disclosed herein.

General synthetic procedures for the compounds of this invention are described below. The synthetic schemes are presented as examples and do not limit the scope of the invention in any way.

General Procedure A

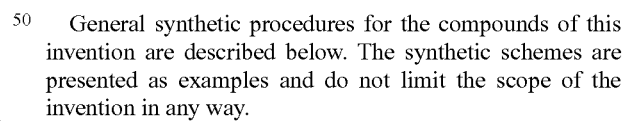
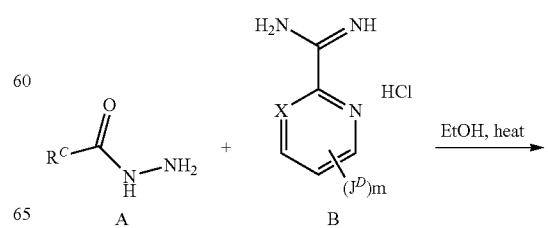
A    B

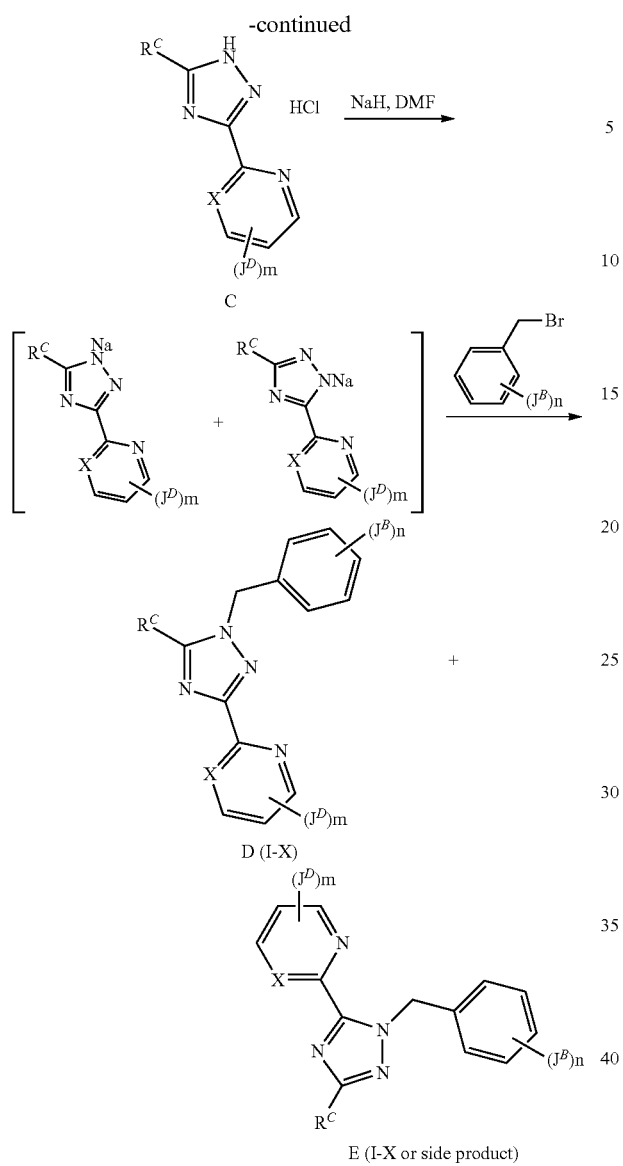

D (I-X)

E (I-X or side product)

Step 1: Triazole Formation:

A mixture of hydrazide A (1.0 eq) and amidine B (1.0 eq) in EtOH (0.05 to 0.3 M depending on solubility) in a sealed vial is heated, e.g., to about 100-110° C. (bath temperature) and monitored by LC/MS analysis. Once complete (reaction time typically 24 h), the reaction mixture is concentrated, azeotroped with toluene and dried in vacuo to afford triazole C as the hydrochloride salt. It is carried on to alkylation step without any further purification.

Step 2: Alkylation:

Triazole C is dissolved in DMF and treated with sodium hydride (e.g., about 60% w/w in mineral oil, about 2.0 eq) and the appropriate benzyl bromide (e.g., about 1.5 eq). The reaction is stirred at room temperature and monitored by LC/MS analysis. Once complete (reaction time typically 30 min), the reaction solution is diluted with ethyl acetate and washed with water (e.g., 4 times) and brine. The organic layer is dried, e.g., over $MgSO_4$ or $Na_2SO4$, filtered and concentrated. The crude material is purified using SiO2 chromatography and an appropriate solvent gradient (ethyl acetate/hexanes or DCM/methanol) to afford products D and E. In all cases, the two regioisomers are readily separable. Structural assignments are based on 1H NMR analysis and confirmed by observed activities in biological assays.

General Procedure B

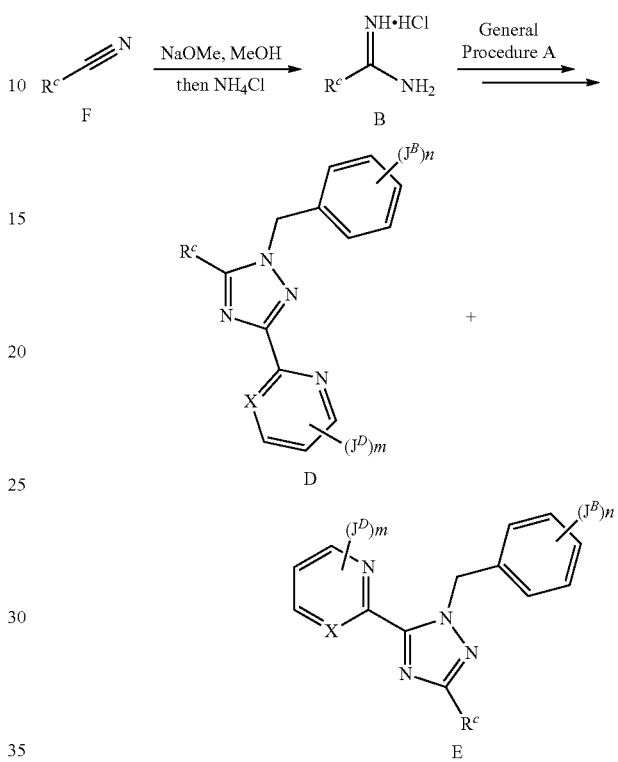

Amidine Formation:

Nitrile F is treated with sodium methoxide (e.g., about 0.5 M in methanol, about 0.5 eq) at room temperature and monitored by LC/MS analysis. Once the starting nitrile is consumed (reaction time was typically 2-7 h), ammonium chloride (e.g., about 1.1 eq) is added and the reaction mixture is stirred for about 16-24 h. The reaction mixture is concentrated and dried in vacuo. In some case, the crude amidine is collected by filtration.

The crude amidine is then used as one of the starting compounds in General Procedure A described above without any further purification to yield Compounds D and E.

General Procedure C

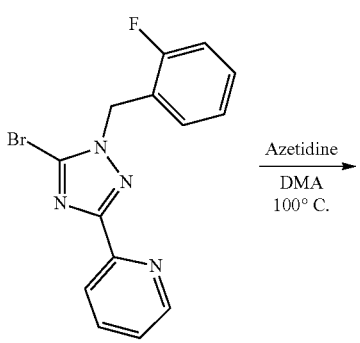

-continued

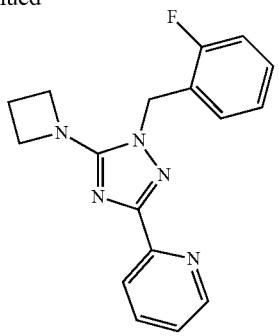

A solution of 2-(5-bromo-1-(2-fluorobenzyl)-1H-1,2,4-triazol-3-yl)pyridine (I-16), in DMA is treated with a large excess of azetidine (e.g., ~30 eq). The resultant solution is warmed to about 100° C. and stirred at that temperature for about 18 h. The reaction solution is cooled to room temperature, poured into 1N NaOH solution and then extracted with EtOAc. The organic phases are dried, e.g., over MgSO4 or Na2SO4, filtered and concentrated. The crude product is purified using SiO2 chromatography and an appropriate gradient (MeOH—CH3CN (1:7)/CH2Cl2) to yield 2-(5-(azetidin-1-yl)-1-(2-fluorobenzyl)-1H-1,2,4-triazol-3-yl)pyridine (I-23) as a solid.

General Procedure D

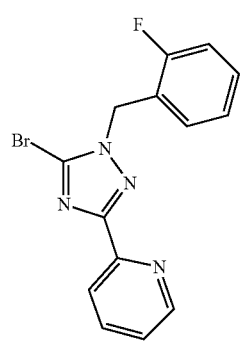

Pyrazole, NaH
DMF
50° C.

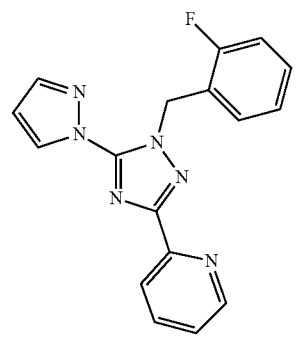

A solution of pyrazole (1.1 eq) in DMF is treated with sodium hydride (e.g., about 60% w/w in mineral oil, about 1.2 eq) and stirred for about 10 min at room temperature. 2-(5-Bromo-1-(2-fluorobenzyl)-1H-1,2,4-triazol-3-yl)pyridine (I-16, e.g., 1.0 eq) is then added. The resultant mixture is warmed to about 50° C. and stirred at that temperature for about 1 h. The reaction solution is cooled to room temperature, poured into water, and filtered to yield 2-(1-(2-fluorobenzyl)-5-(1H-pyrazol-1-yl)-1H-1,2,4-triazol-3-yl)pyridine (I-10) as a solid.

General Procedure E

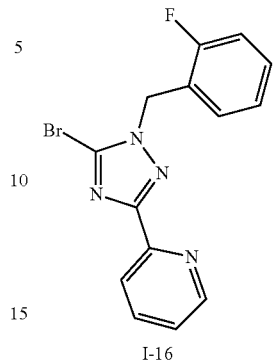

I-16

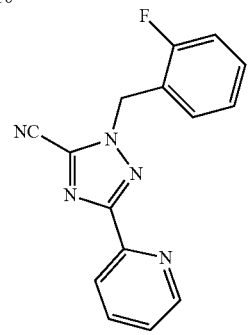

I-33

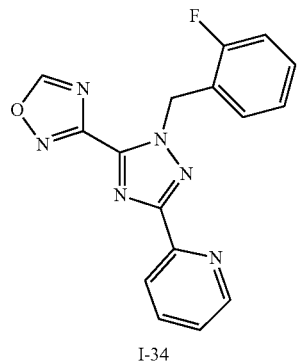

I-34

To a solution of 2-(5-bromo-1-(2-fluorobenzyl)-1H-1,2,4-triazol-3-yl)pyridine (I-16, e.g., about 0.95 g, 2.9 mmol) in N,N-dimethylformamide (e.g., 9.5 mL) is added potassium cyanide (e.g., about 0.928 g, 14.3 mmol). After heating the solution at about 100° C. for about 22 h, the solution is diluted with ethyl acetate (e.g., about 125 mL) and water (e.g., about 100 mL). The layers are separated, and the aqueous layer is extracted with ethyl acetate (e.g., about 2×50 mL). The organics are combined, washed with water (e.g., about 50 mL) and brine (e.g., about 50 mL), dried, e.g., over sodium sulfate or magnesium sulfate, filtered, and the solvent is removed in vacuo to give the crude product, I-33. Purification by silica gel chromatography (0-15% ethyl acetate in dichloromethane) yields 1-(2-fluorobenzyl)-3-(pyridin-2-yl)-1H-1,2,4-triazole-5-carbonitrile I-33 (I-33) as a solid.

To a solution of 1-(2-fluorobenzyl)-3-(pyridin-2-yl)-1H-1,2,4-triazole-5-carbonitrile (I-33, e.g., about 100 mg, 0.358 mmol) and potassium carbonate (e.g., about 198 mg, 1.43 mmol) in methanol (e.g., about 3.6 mL) is added hydroxylamine hydrochloride (e.g., about 75 mg, 1.1 mmol). The solution is heated to about 70° C. for about 1.25 h, at which point the solution is diluted with ethyl acetate (e.g., about 20 mL) and the solids are filtered off through a cotton plug. The solvent is removed in vacuo and the crude residue is diluted with water (e.g., about 50 mL) and a mixture of dichloromethane and 2-propanol, e.g., a 5:1 mixture of dichloromethane and 2-propanol (e.g., about 50 mL). The layers are separated and the organic layer is washed with water (e.g., about 50 mL), dried, e.g., over sodium sulfate or magnesium sulfate, and the solvent is removed in vacuo. To the resulting crude 1-(2-fluorobenzyl)-N'-hydroxy-3-(pyridin-2-yl)-1H-1,2,4-triazole-5-carboximidamide is added trimethyl orthoformate (e.g., about 4.5 mL, 41 mmol) and a catalytic amount of p-toluensulfonic acid monohydrate (e.g., about 3.4 mg, 0.018 mmol). The solution is heated to about 100° C. for about 1.5 h, and the excess orthoformate is removed in vacuo to give the crude product, I-34. Purification by silica gel chromatography (e.g., 20-80% ethyl acetate in hexanes) yields 3-(1-(2-fluorobenzyl)-3-(pyridin-2-yl)-1H-1,2,4-triazol-5-yl)-1,2,4-oxadiazole, I-34, as a solid.

General Procedure F

In the compounds of Formula IA or IB, any bromo substituent on ring D, i.e., when $J^D$ is Br, can be converted into an amino substituent with the procedure as shown below to obtain the corresponding compound having —NH$_2$ as $J^D$. Similarly, any bromo substituent on ring C, i.e., when $J^C$ is Br, in a compound of Formula IA or IB can be converted into an amino substituent with the procedure as shown below to obtain the corresponding compound having —NH$_2$ as $J^C$. In the reaction scheme described below, compound I-19 is used as an example to demonstrate the conversion of a bromo ring substituent, e.g., Br as $J^D$, to an amino ring substituent, e.g., —NH$_2$ as $J^D$, in a compound of Formula IA or IB.

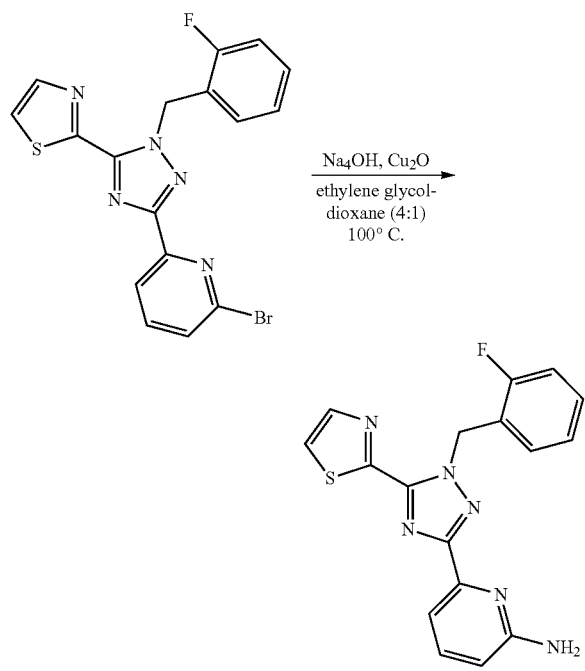

To a suspension of 2-(3-(6-bromopyridin-2-yl)-1-(2-fluorobenzyl)-1H-1,2,4-triazol-5-yl)thiazole (I-19) and copper(I) oxide (e.g., about 0.2 eq) in ethylene glycol-dioxane (e.g., about 4:1) in a sealed tube is added ammonium hydroxide solution (e.g., ~29% in water, ~30 eq). The resultant mixture is warmed to about 100° C. and stirred at that temperature for about 24 h. The reaction solution is cooled to room temperature, poured into 1N NaOH solution and then extracted with EtOAc. The organic phases are dried, e.g., over Na$_2$SO$_4$ or MgSO$_4$, filtered and concentrated. The crude product is purified using SiO2 chromatography and an appropriate gradient (EtOAc/hexanes) to give 6-(1-(2-fluorobenzyl)-5-(thiazol-2-yl)-1H-1,2,4-triazol-3-yl)pyridin-2-amine (I-14) as a solid.

Pharmaceutically Acceptable Salts

The phrase "pharmaceutically acceptable salt," as used herein, refers to pharmaceutically acceptable organic or inorganic salts of a compound of Formula IA or Formula IB. For use in medicine, the salts of the compounds of Formula IA or Formula IB will be pharmaceutically acceptable salts. Other salts may, however, be useful in the preparation of the compounds of Formula IA or Formula IB or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When the compound of Formula IA or Formula IB is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N.sup.1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of Formula IA or Formula IB is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and palmoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

Pharmaceutical Compositions and Methods of Administration

The compounds herein disclosed, and their pharmaceutically acceptable salts, may be formulated as pharmaceutical compositions or "formulations".

A typical formulation is prepared by mixing a compound of Formula IA or Formula IB, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of Formula IA or Formula IB is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula IA or Formula IB or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula IA or Formula IB, a pharmaceutically acceptable salt thereof, wherein the compound of Formula IA or IB, or its pharmaceutically acceptable salt, can be in a stabilized form, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula IA or Formula IB or a pharmaceutically acceptable salt thereof, is typically formulated into pharmaceutical dosage forms to provide an easily controllable dosage of the drug and to enable patient compliance with the prescribed regimen. Pharmaceutical formulations of compounds of Formula IA or Formula IB, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula IA or Formula IB will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, tretralose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacrylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e g ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semipermeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolat. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e. g., Explotab™ CLV), microcrystalline cellulose (e. g., Avicel™), microcrystalline silicified cellulose (e. g., ProSolv™) and croscarmellose sodium (e. g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multi-layered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. No. 6,419,952, U.S. Pat. No. 6,342,249, U.S. Pat. No. 5,324,280, U.S. Pat. No. 4,672,850, U.S. Pat. No. 4,627,850, U.S. Pat. No. 4,203,440, and U.S. Pat. No. 3,995,631.

As further noted above, the agents described herein may be provided in the form of microparticulates, generally ranging in size from about 10 µm to about 2 mm (including, for example, from about 100 µm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 µm) can be designed using polymers able to be degraded in vivo (e.g. biodegradable poly-alkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula IA or Formula IB that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending the compound of Formula IA or Formula IB in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of compounds of Formula IA or Formula IB contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using compounds of Formula IA or Formula IB may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of compounds of Formula IA or Formula IB include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula IA or Formula IB or a pharmaceutically acceptable salt thereof, may be formulated in a veterinary composition comprising a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Therapeutic Methods

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO might be desirable, such as pulmonary hypertension, arterial hypertension, heart failure, atherosclerosis, inflammation, thrombosis, renal fibrosis and failure, liver cirrhosis, erectile dysfunction and other related cardiovascular disorders.

In one embodiment, the compounds herein disclosed are NO-independent, heme-dependent sGC stimulators that can be used to prevent and/or treat conditions, diseases or disorders in which it is considered desirable to increase the concentration of cGMP. Increased concentration of cGMP leads to vasodilatation, inhibition of platelet aggregation and adhesion, anti-hypertensive effects, anti-remodeling effects, anti-apoptotic effects, anti-inflammatory effects and neuronal signal transmission effects. Thus, sGC stimulators may be used to treat and/or prevent a range of diseases and disorders, including but not limited to cardiovascular, endothelial, pulmonary, renal, hepatic and sexual diseases and disorders.

In other embodiments, the compounds here disclosed are sGC stimulators that may be useful in the prevention and/or treatment of diseases and disorders characterized by undesirable reduced bioavailability of and/or sensitivity to NO, such as those associated with conditions of oxidative stress or nitrosative stress.

Specific diseases of disorders which may be treated and/or prevented by administering an sGC stimulator, include but are not limited to: arterial hypertension, pulmonary hypertension, heart failure, stroke, septic shock, atherosclerosis, thrombosis, renal fibrosis, ischemic renal disease and renal failure, liver cirrhosis, erectile dysfunction, male and female sexual dysfunction, sickle cell anemia, asthma, chronic obstructive pulmonary disease, and neuro inflammatory diseases or disorders.

Pulmonary hypertension (PH) is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

The compounds according to Formula IA or Formula IB of the present invention as well as pharmaceutically acceptable salts thereof, as stimulators of sGC, are useful in the prevention and/or treatment of the following types of diseases, conditions and disorders which can benefit from sGC stimulation:

(1) Peripheral or cardiac vascular disorders/conditions:
pulmonary hypertension, pulmonary arterial hypertension, and associated pulmonary vascular remodeling (e.g. localized thrombosis and right heart hypertrophy); pulmonary hypertonia; primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; pulmonary hypertension associated with or related to: left ventricular dysfunction, hypoxemia, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), connective tissue disease, lupus, schitosomiasis, sarcoidosis, chronic obstructive pulmonary disease, emphysema, chronic bronchitis, pulmonary capillary hemangiomatosis; histiocytosis X, lymphangiomatosis and compressed pulmonary vessels (such as due to adenopathy, tumor or fibrosing mediastinitis)

disorders related to high blood pressure and decreased coronary blood flow such as increased acute and chronic coronary blood pressure, arterial hypertension and vascular disorder resulting from cardiac and renal complications (e.g. heart disease, stroke, cerebral ischemia, renal failure); congestive heart failure; thromboembolic disorders and ischemias such as myocardial infarction, stroke, transient ischemic attacks; stable or unstable angina pectoris; arrhythmias; diastolic dysfunction; coronary insufficiency;

Atherosclerosis (e.g., associated with endothelial injury, platelet and monocyte adhesion and aggregation, smooth muscle proliferation and migration); restenosis (e.g. developed after thrombolysis therapies, percutaneous transluminal angioplasties (PTAs), percutaneous transluminal coronary angioplasties (PTCAs) and bypass); inflammation;

liver cirrhosis, associated with chronic liver disease, hepatic fibrosis, hepatic stellate cell activation, hepatic fibrous collagen and total collagen accumulation; liver disease of necro-inflammatory and/or of immunological origin; and (2) Urogenital system disorders, such as renal fibrosis and renal failure resulting from chronic kidney diseases or insufficiency (e.g. due to accumulation/deposition and tissue injury, progressive sclerosis, glomerunephritis); prostate hypertrophy; erectile dysfunction; female sexual dysfunction and incontinence.

In some embodiments of the invention, the compounds according to Formula IA or Formula IB as well as pharmaceutically acceptable salts thereof are also useful in the prevention and/or treatment of the following types of diseases, conditions and disorders which can benefit from sGC stimulation:

(a) A peripheral or cardiac vascular disorder or health condition selected from: pulmonary hypertension, pulmonary arterial hypertension, and associated pulmonary vascular remodeling, localized pulmonary thrombosis, right heart hypertrophy, pulmonary hypertonia, primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; pulmonary hypertension associated with or related to: left ventricular dysfunction, hypoxemia, mitral valve disease, constrictive pericarditis, aortic stenosis, cardiomyopathy, mediastinal fibrosis, pulmonary fibrosis, anomalous pulmonary venous drainage, pulmonary venooclusive disease, pulmonary vasculitis, collagen vascular disease, congenital heart disease, pulmonary venous hypertension, interstitial lung disease, sleep-disordered breathing, apnea, alveolar hypoventilation disorders, chronic exposure to high altitude, neonatal lung disease, alveolar-capillary dysplasia, sickle cell disease, other coagulation disorders, chronic thromboembolism, pulmonary embolism, connective tissue disease, lupus, schitosomiasis, sarcoidosis, chronic obstructive pulmonary disease, emphysema, chronic bronchitis, pulmonary capillary hemangiomatosis; histiocytosis X, lymphangiomatosis or compressed pulmonary vessels;

(b) Liver cirrhosis, or (c) a urogenital system disorder selected from renal fibrosis, renal failure resulting from chronic kidney diseases or insufficiency, erectile dysfunction or female sexual dysfunction.

In other embodiments of the invention, the compounds according to Formula IA or Formula IB as well as pharmaceutically acceptable salts thereof are useful in the prevention and/or treatment of the following types of diseases, conditions and disorders which can benefit from sGC stimulation:

pulmonary hypertension, pulmonary arterial hypertension, and associated pulmonary vascular remodeling, localized pulmonary thrombosis, right heart hypertrophy, pulmonary hypertonia, primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy or chronic obstructive pulmonary disease, liver cirrhosis, renal fibrosis, renal failure resulting from chronic kidney diseases or insufficiency, erectile dysfunction or female sexual dysfunction.

In still other embodiments, the compounds according to Formula IA or Formula IB as well as pharmaceutically acceptable salts thereof are useful in the prevention and/or treatment of the following types of diseases, conditions and disorders which can benefit from sGC stimulation:

Pulmonary hypertension, pulmonary arterial hypertension, and associated pulmonary vascular remodeling, pulmonary hypertonia, primary pulmonary hypertension, secondary pulmonary hypertension, familial pulmonary hypertension, sporadic pulmonary hypertension, pre-capillary pulmonary hypertension or idiopathic pulmonary hypertension.

The terms, "disease", "disorder" and "condition" may be used interchangeably here to refer to a sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of these diseases, conditions and disorders in a subject, comprising administering a therapeutically effective amount of the compound of Formula IA or Formula IB, or a pharmaceutically acceptable salt thereof, in the subject in need of the treatment. Alternatively, the invention provides the use of the compound of Formula IA or Formula IB, or a pharmaceutically acceptable salt thereof, in the treatment of one of these diseases, conditions and disorders in a subject in need of the treatment. The invention further provides a method of making a medicament useful for treating one of these diseases, conditions and disorders comprising using the compound of Formula IA or Formula IB, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of a sGC, cGMP and/or NO mediated condition, or the amelioration of one or more symptoms (preferably, one or more discernable symptoms) of said condition (i.e. "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of a sGC, cGMP and/or NO mediated condition. In other embodiments the terms "treat", "treatment" and "treating" refer to the inhibition of the progression of a sGC, cGMP and/or NO mediated condition, either physically by, e.g., stabilization of a discernable symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "preemptive" measure to a patient, specifically a human, having a predisposition (e.g. a genetic predisposition) to developing a sGC, cGMP and/or NO related disease, disorder or symptom.

In other embodiments, the methods of the invention are a preventative or "preemptive" measure to a patient, specifically a human, suffering from a disease, disorder or condition that makes him at risk of developing a sGC, cGM or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula IA or Formula IB or a pharmaceutically acceptable salt thereof, and a second amount of an additional suitable therapeutic agent.

In one embodiment of this invention, the compound of Formula IA or Formula IB and the additional therapeutic agent are each administered in an effective amount (i.e., each in an amount which would be therapeutically effective if administered alone). In another embodiment, the compound of Structural Formula IA or Formula IB and the additional therapeutic agent are each administered in an amount which alone does not provide a therapeutic effect (a sub-therapeutic dose). In yet another embodiment, the compound of Structural Formula IA or Formula IB can be administered in an effective amount, while the additional therapeutic agent is administered in a sub-therapeutic dose. In still another embodiment, the compound of Structural Formula IA or Formula IB can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Structural Formulae I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula IA or Formula IB and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of this disclosure, either administered separately or in the same pharmaceutical composition, include, but are not limited to:

(1) Endothelium-derived releasing factor (EDRF);
(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitroglycerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatrate®-SR, Imdur®, Ismo®, Isordil®, Isordil®, Titradose®, Monoket®), FK 409 (NOR-3); FR 144420 (NOR-4); 3-morpholinosydnonimine; Linsidomine chlorohydrate ("SIN-1"); S-nitroso-N-acetylpenicillamine ("SNAP"); AZD3582 (CINOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), 5-nitrosoglutathione (GSNO), S-nitrosoglutathione mono-ethyl-ester (GSNO-ester), 6-(2-hydroxy-1-methyl-nitrosohydrazino)-N-methyl-1-hexanamine (NOC-9) or diethylamine NONOate. Nitric oxide donors are also as disclosed in U.S. Pat. Nos. 5,155,137, 5,366,997, 5,405,919, 5,650,442, 5,700,830, 5,632,981, 6,290,981, 5,691,423 5,721,365, 5,714,511, 6,511,911, and 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;
(3) Other substances that enhance cGMP concentrations such as protoporphyrin IX, arachidonic acid and phenyl hydrazine derivatives;
(4) Nitric Oxide Synthase substrates: for example, n-hydroxyguanidine based analogs, such as N[G]-hydroxy-L-arginine (NOHA), 1-(3,4-dimethoxy-2-chlorobenzylideneamino)-3-hydroxyguanidine, and PR5 (1-(3,4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluormethyl) propylguanidine; and others reviewed in Cali et al. (2005, Current Topics in Medicinal Chemistry 5:721-736) and disclosed in the references cited therein;
(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g. 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schäfer et al., Journal of Thrombosis and Homeostasis 2005; Volume 3, Supplement 1: abstract number P1487);
(6) NO independent heme-independent sGC activators, including, but not limited to:
BAY 58-2667 (see patent publication DE19943635)

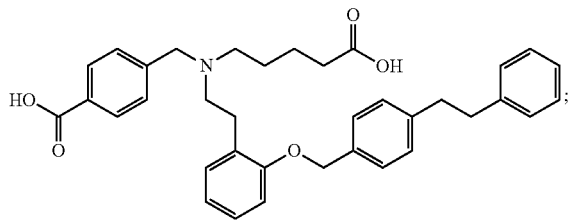 [SMILES: O=C(O)CCCCN(CCc1ccccc1OCc1ccc(CCc2ccccc2)cc1)Cc1ccc(C(=O)O)cc1]

HMR-1766 (ataciguat sodium, see patent publication WO2000002851)

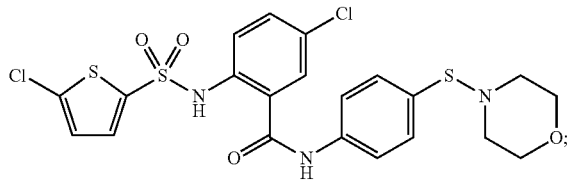 [SMILES: O=C(Nc1ccc(SN2CCOCC2)cc1)c1cc(Cl)ccc1NS(=O)(=O)c1ccc(Cl)s1]

S 3448 (2-(4-chloro-phenylsulfonylamino)-4,5-dimethoxy-N-(4-(thiomorpholine-4-sulfonyl)-phenyl)-benzamide (see patent publications DE19830430 and WO2000002851)

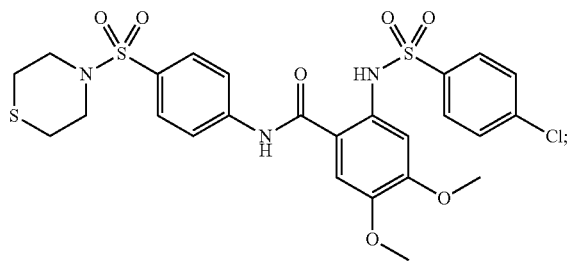 [SMILES: COc1cc(NS(=O)(=O)c2ccc(Cl)cc2)c(C(=O)Nc2ccc(S(=O)(=O)N3CCSCC3)cc2)cc1OC]

and
HMR-1069 (Sanofi-Aventis).
(7) Heme-dependent sGC stimulators including, but not limited to:

YC-1 (see patent publications EP667345 and DE19744026)

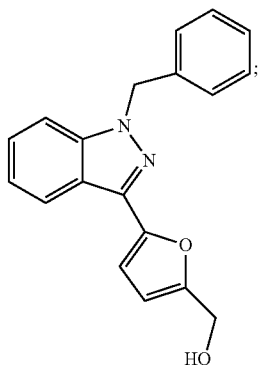 [SMILES: OCc1ccc(-c2nn(Cc3ccccc3)c3ccccc23)o1]

BAY 41-2272 (see patent publications DE19834047 and DE19942809)

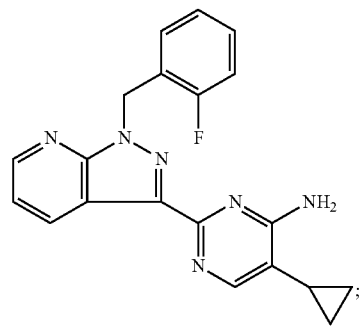 [SMILES: Nc1nc(-c2nn(Cc3ccccc3F)c3ncccc23)ncc1C1CC1]

BAY 41-8543 (see patent publication DE19834044)

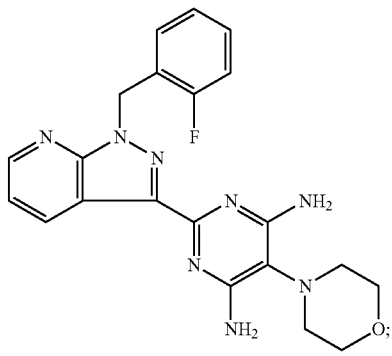 [SMILES: Nc1nc(-c2nn(Cc3ccccc3F)c3ncccc23)nc(N)c1N1CCOCC1]

BAY 63-2521 (see patent publication DE19834044)
CFM-1571 (see patent publication WO2000027394)

A350-619

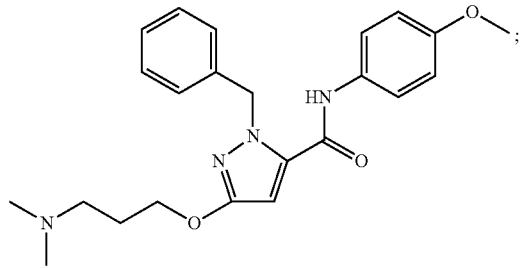

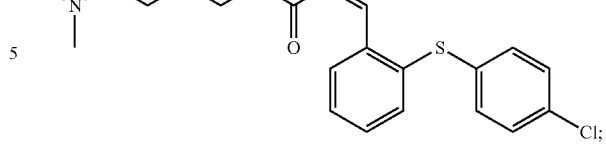

A-344905

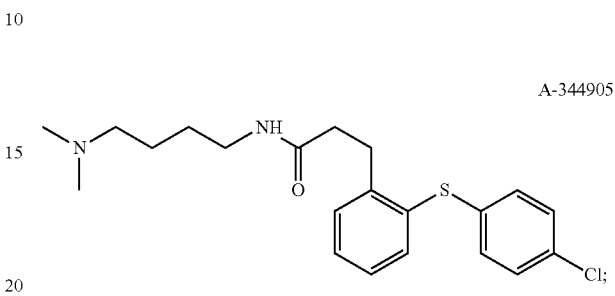

A-778935

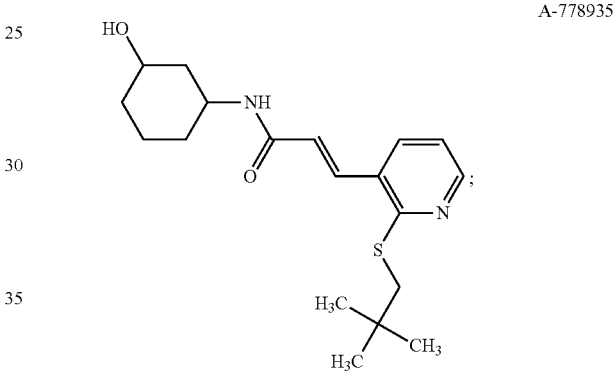

and other compounds disclosed in Tetrahedron Letters (2003), 44(48): 8661-8663.

(8) Compounds that inhibit the degradation of cGMP, such as: PDE5 inhibitors, such as, for example, Sildenafil (Viagra®) and other related agents such as Avanafil, Lodenafil, Mirodenafil, Sildenafil citrate, Tadalafil (Cialis®), Vardenafil (Levitra®) and Udenafil; Alprostadil; and Dipyridamole;

(9) Calcium channel blockers such as:

Dihydropyridine calcium channel blockers: Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas);

Phenylalkylamine calcium channel blockers: Verapamil (Calan, Isoptin)

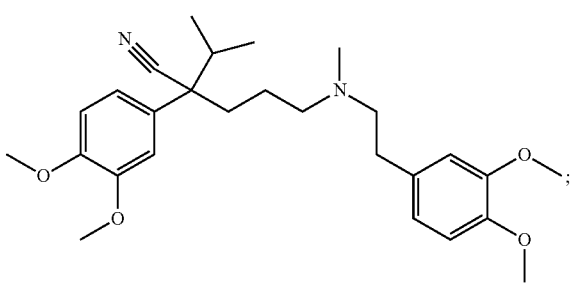

Gallopamil (Procorum, D600);
Benzothiazepines: Diltiazem (Cardizem);

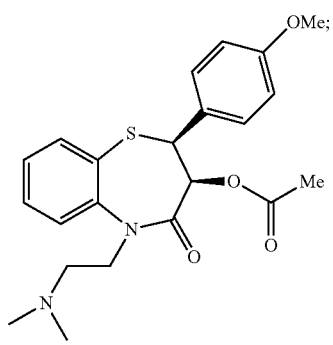 [SMILES: COc1ccc([C@@H]2Sc3ccccc3N(CCN(C)C)C(=O)[C@@H]2OC(C)=O)cc1]

Nonselective calcium channel inhibitors such as: mibefradil, bepridil and fluspirilene, fendiline
(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S; dual/nonselective endothelin antagonist Actelion-1, that entered clinical trials in 2008;
(11) Prostacyclin derivatives: for instance prostacyclin (prostaglandin $I_2$), Epoprostenol (synthetic prostacyclin, marketed as Flolan®); Treprostinil (Remodulin®) Iloprost (Ilomedin®), Iloprost (marketed as Ventavis®); oral and inhaled forms of Remodulin® that are under development; Beraprost, an oral prostanoid available in Japan and South Korea;
(12) Antihyperlipidemics such as: cholestyramine, colestipol, and colesevelam; statins such as Atorvastatin, Simvastatin, Lovastatin and Pravastatin; Rosuvastatin; also combinations of statins, niacin, intestinal cholesterol absorption-inhibiting supplements (ezetimibe and others, and to a much lesser extent fibrates);
(13) Anticoagulants, such as the following types:
Coumarines (Vitamin K antagonists): Warfarin® (Coumadin) mostly used in the US and UK; Acenocoumarol® and Phenprocoumon®, mainly used in other countries; Phenindione®;
Heparin and derivative substances such as: Heparin; low molecular weight heparin, Fondaparinux and Idraparinux;
Direct thrombin inhibitors such as: Argatroban, Lepirudin, Bivalirudin and Dabigatran; Ximelagatran (Exanta®), not approved in the US;
Tissue plasminogen activators, used to dissolve clots and unblock arteries, such as Alteplase;
(14) Antiplatelet drugs: for instance thienopyridines such as Lopidogrel and Ticlopidine; Dipyridamole; Aspirin;
(15) ACE inhibitors, for example the following types:
Sulfhydryl-containing agents such as Captopril (trade name Capoten®), the first ACE inhibitor and Zofenopril;
Dicarboxylate-containing agents such as Enalapril (Vasotec/Renitec®); Ramipril (Altace/Tritace/Ramace/Ramiwin®); Quinapril (Accupril®) Perindopril (Coversyl/Aceon®); Lisinopril (Lisodur/Lopril/Novatec/Prinivil/Zestril®) and Benazepril (Lotensin®);
Phosphonate-containing agents such as: Fosinopril;
Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;
(16) Supplemental oxygen therapy;
(17) Beta blockers, such as the following types:
Non-selective agents: Alprenolol®, Bucindolol®, Carteolol®, Carvedilol® (has additional α-blocking activity), Labetalol® (has additional α-blocking activity), Nadolol®, Penbutolol® (has intrinsic sympathomimetic activity), Pindolol® (has intrinsic sympathomimetic activity), Propranolol® and Timolol®;
$β_1$-Selective agents: Acebutolol® (has intrinsic sympathomimetic activity), Atenolol®, Betaxolol®, Bisoprolol®, Celiprolol®, Esmolol®, Metoprolol® and Nebivolol®;
$β_2$-Selective agents: Butaxamine® (weak α-adrenergic agonist activity);
(18) Antiarrhythmic agents such as the following types:
Type I (sodium channel blockers): Quinidine, Lidocaine, Phenytoin, Propafenone
Type III (potassium channel blockers): Amiodarone, Dofetilide, Sotalol
Type V: Adenosine, Digoxin
(19) Diuretics such as: Thiazide diuretics, e.g., chlorothiazide, chlorthalidone, and hydrochlorothiazide; Loop diuretics, such as furosemide; potassium-sparing diuretics such as amiloride, spironolactone, and triamterene; combinations of these agents;
(20) Exogenous vasodilators such as:
Adenocard®, an adenosine agonist, primarily used as an anti-arrhythmic;
Alpha blockers (which block the vasoconstricting effect of adrenaline);
Atrial natriuretic peptide (ANP);
Ethanol;
Histamine-inducers, which complement proteins C3a, C4a and C5a work by triggering histamine release from mast cells and basophil granulocytes;
Tetrahydrocannabinol (THC), major active chemical in marijuana which has minor vasodilatory effects;
Papaverine, an alkaloid found in the opium poppy papaver somniferum;
(21) Bronchodilators: there are two major types of bronchodilator, $β_2$ agonists and anticholinergics, exemplified below:
$β_2$ agonists: Salbutamol® or albuterol (common brand name: Ventolin) and Terbutaline® are short acting $β_2$ agonists for rapid relief of COPD symptoms. Long acting $β_2$ agonists (LABAs) such as Salmeterol® and Formoterol®;

anticholinergics: Ipratropium® is the most widely prescribed short acting anticholinergic drug. Tiotropium® is the most commonly prescribed long-acting anticholinergic drug in COPD;
Theophylline®, a bronchodilator and phosphodiesterase inhibitor;
(22) Corticosteroids: such as beclomethasone, methylprednisolone, betamethasone, prednisone, prenisolone, triamcinolone, dexamethasone, fluticasone, flunisolide and hydrocortisone, and corticosteroid analogs such as budesonide
(23) Dietary supplements such as, for example: omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;
(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WO0178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;
(25) Immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);
(26) Non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);
(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufumic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);
(28) Cyclooxygenase-2 (COX-2) inhibitors such as celecoxib (Celebrex®), rofecoxib (Vioxx®), valdecoxib, etoricoxib, parecoxib and lumiracoxib; (opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and
(29) Anti-diabetic agents such as insulin and insulin mimetics, sulfonylureas (e.g., glyburide, meglinatide), biguanides, e.g., metformin (Glucophage®), α-glucosidase inhibitors (acarbose), thiazolidinone compounds, e.g., rosiglitazone (Avandia®), troglitazone (Rezulin®), ciglitazone, pioglitazone (Actos®) and englitazone.

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference in their entirety. As used herein, all abbreviations, symbols and conventions are consistent with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

The products of Examples 1-3 below were prepared using General Procedure A described above, containing the following two steps.

Step 1: Triazole Formation:

A mixture of hydrazide A (1.0 eq) and amidine B (1.0 eq) in EtOH (0.05 to 0.3 M depending on solubility) in a sealed vial was heated at 100-110° C. (bath temperature) and monitored by LC/MS analysis. Once complete (reaction time was typically 24 h), the reaction mixture was concentrated, azeotroped with toluene and dried in vacuo to afford triazole C as the hydrochloride salt. Triazole C was carried on to the alkylation step without any further purification.

Step 2: Alkylation:

Triazole C was dissolved in DMF and treated with sodium hydride (60% w/w in mineral oil, 2.0 eq) and the appropriate benzyl bromide (1.5 eq). The reaction was stirred at room temperature and monitored by LC/MS analysis. Once complete (reaction time was typically 30 min), the reaction mixture was diluted with ethyl acetate and washed with water (4 times) and brine. The organic layer was dried over $Na_2SO_4$, filtered and concentrated. The crude material was purified using $SiO_2$ chromatography and an appropriate solvent gradient (ethyl acetate/hexanes or DCM/methanol) to afford products D and E. In all cases, the two regioisomers were readily separable. Structural assignments were based on $^1H$ NMR analysis and confirmed by observed activities in biological assays.

Example 1

Compounds I-8 and I-9

Step 1

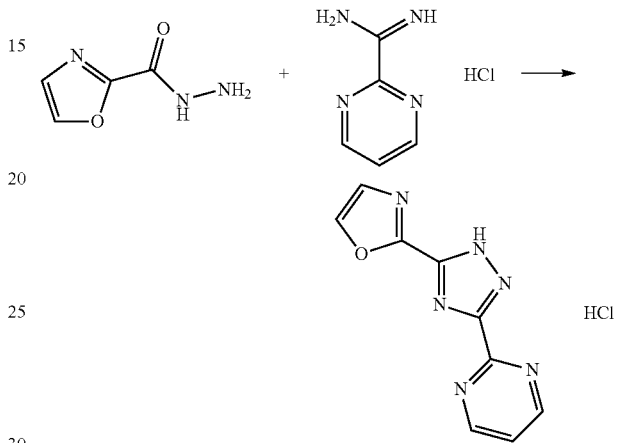

To a vial charged with pyrimidine-2-carboximidamide hydrochloride (250 mg, 1.576 mmol) and oxazole-2-carbohydrazide (200 mg, 1.576 mmol) was added EtOH (12 mL). The vial was sealed and heated at 100° C. for 23 h. The two starting materials went into solution almost immediately. The yellow solution was cooled (a ppt formed) and concentrated. The sample was azeotroped two times with toluene. LCMS of the major peak: m/z 215.15 (M+1). This crude product was used without further purification or characterization. The product was a yellow solid.

Step 2

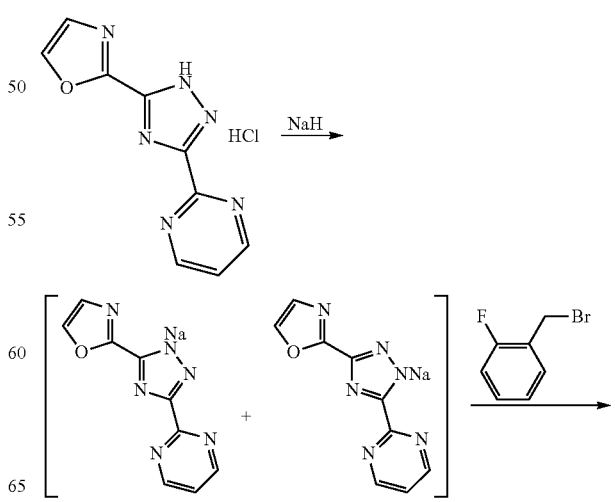

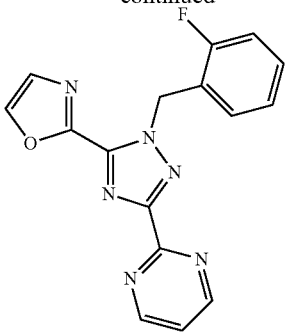

I-9

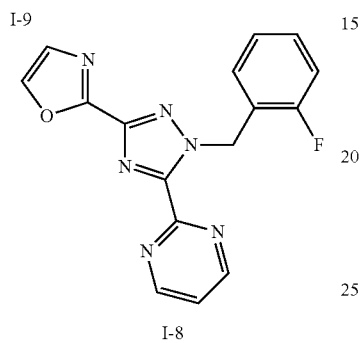

I-8

To a vial charged with 2-(3-(pyrimidin-2-yl)-1H-1,2,4-triazol-5-yl)oxazole hydrochloride (395 mg, 1.575 mmol) was added sodium hydride (157 mg, 3.94 mmol) followed by DMF (8 mL). The reaction evolved gas, became yellow, and was stirred at rt for ~30 min. Then 1-(bromomethyl)-2-fluorobenzene (0.310 mL, 2.52 mmol) was added and the reaction stirred at room temperature for 1 h. The reaction was poured into water and extracted with EtOAc (twice). The organic layers were washed with water and dried with $MgSO_4$. The crude product was added to an 80 g ISCO silica gel column and was purified with a gradient of 0% to 20% ($CH_3CN$/MeOH [7:1])/DCM.

Examination of both products, I-8 and I-9, with mass spectrometry resulted in the following peak: LCMS m/z 323.3 (M+1).

I-8: $^1$H NMR ($CDCl_3$/400 MHz) δ 8.88 (d, 2H), 7.76 (s, 1H), 7.35 (t, 1H), 7.29 (s, 1H), 7.22-7.15 (m, 1H), 7.10 (td, 1H), 7.00-6.94 (m, 2H), 6.21 (s, 2H); MS m/z: 323.3 (M+1).

I-9: $^1$H NMR ($CDCl_3$/400 MHz) δ 8.90 (d, 2H), 7.83 (d, 1H), 7.35-7.33 (m, 2H), 7.26-7.20 (m, 1H), 7.09 (td, 1H), 7.05-6.98 (m, 2H), 6.19 (s, 2H); MS m/z: 323.3 (M+1).

Example 2

Compounds I-12 and I-13

To a solution of oxazole-4-carbohydrazide (228 mg, 1.794 mmol) in ethanol (8.9 mL) was added picolinimidamide hydrochloride (283 mg, 1.79 mmol). After heating the orange solution at 100° C. for 50 h, the solvent was removed in vacuo and the residue was azeotroped with toluene (2×4 mL) to give 514 mg of crude material. 187 mg of the crude material (0.75 mmol) was dissolved in N,N-dimethylformamide (3.7 mL) and treated with sodium hydride (60% dispersion in mineral oil, 75 mg, 1.9 mmol) in a single portion at ambient temperature. After stirring for 20 min, 1-(bromomethyl)-2-fluorobenzene (0.136 mL, 1.12 mmol) was added. The solution was stirred for an additional 45 min, at which point the solution was poured into water (75 mL) and extracted with ethyl acetate (3×50 mL). The organics were combined, washed with water (2×50 mL) and brine (1×50 mL), dried over magnesium sulfate, filtered, and the solvent was removed in vacuo to give the crude product as an orange oil. Purification by silica gel chromatography (10-100% ethyl acetate in hexanes) provided 4-(1-(2-fluorobenzyl)-3-(pyridin-2-yl)-1H-1,2,4-triazol-5-yl)oxazole, I-12 (58 mg, 0.18 mmol, 24% yield over two steps) as a tan solid and 4-(1-(2-fluorobenzyl)-5-(pyridin-2-yl)-1H-1,2,4-triazol-3-yl)oxazole, I-13 (21 mg, 0.06 mmol, 8.7% yield over two steps) as a brown solid.

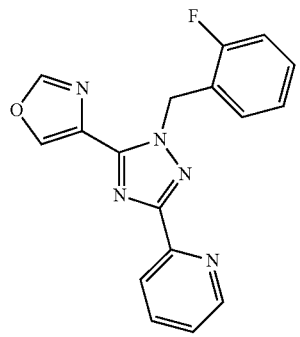

I-12

I-12: $^1$H NMR (400 MHz, $CDCl_3$) δ 8.75-8.53 (m, 1H), 8.50 (s, 1H), 8.17-8.15 (m, 1H), 7.97 (s, 1H), 7.77 (dt, 1H), 7.32-7.29 (m, 1H), 7.26-7.21 (m, 1H), 7.07-6.99 (m, 3H), 6.10 (s, 2H).

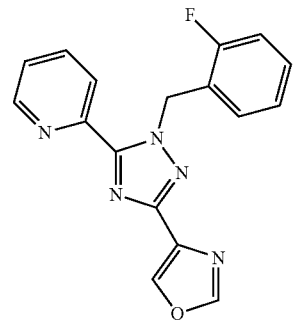

I-13

I-13: $^1$H NMR (400 MHz, $CDCl_3$) δ 8.63-8.61 (m, 1H), 8.32-8.30 (m, 1H), 8.27 (s, 1H), 7.99 (s, 1H), 7.84-7.80 (m, 1H), 7.34-7.31 (m, 1H), 7.23-7.17 (m, 1H), 7.10-6.97 (m, 3H), 6.23 (s, 2H).

Example 3

Compounds I-1, I-2, I-3, I-4, I-5, I-6, I-7, I-11, I-16, I-20, I-21, I-24, I-25, I-26, I-27, I-28, I-29, I-30, I-31, I-32, I-58, I-59, I-51, I-52, I-45, I-46 and I-54, and Intermediate-1

Compounds I-1, I-2, I-3, I-4, I-5, I-6, I-7, I-11, I-16, I-20, I-21, I-24, I-25, I-26, I-27, I-28, I-29, I-30, I-31, I-32, I-58, I-59, I-51, I-52, I-45, I-46 and I-54, and Intermediate-1 were prepared, analogously, using the conditions summarized in General Scheme A and exemplified by Example 1 and Example 2.

Compound I-1

Compound I-1 was synthesized as a white solid (9.4% yield over 2 steps) following the General Procedure A using picolinohydrazide and picolinimidamide in step 1 and 2-fluorobenzyl bromide in step 2.

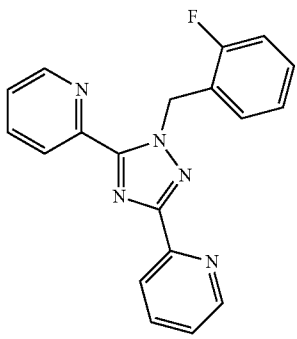

I-1

I-1: $^1$H NMR (400 MHz, CDCl$_3$) δ 8.76 (d, 1H), 8.62 (d, 1H), 8.41 (d, 1H), 8.22 (d, 1H), 7.82 (ddd, 1H), 7.79 (ddd, 1H), 7.33-7.30 (m, 2H), 7.22-7.16 (m, 1H), 7.09-7.00 (m, 2H), 6.97 (t, 1H), 6.29 (s, 2H) ppm.

Compound I-2

Compound I-2 was synthesized as a clear oil (20%) over 2 steps, following General Procedure A and using benzoic hydrazide and 2-amidinopyridine hydrochloride in step 1 and 2-fluorobenzyl bromide in step 2.

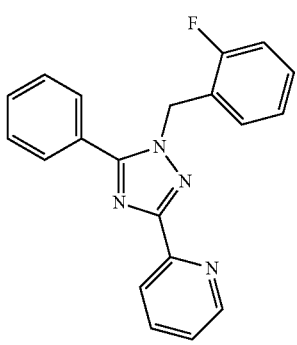

I-2

I-2: $^1$H NMR (400 MHz, CDCl$_3$) δ 8.76 (m, 1H), 8.22 (d, 1H), 7.80 (app. td, 1H), 7.65 (m, 2H), 7.52-7.42 (m, 3H), 7.32-7.26 (m, 2H), 7.16 (app. t, 1H), 7.12-7.04 (m, 2H), 5.59 (s, 2H) ppm. MS: [M+H]=331.

Compounds I-3 and I-20

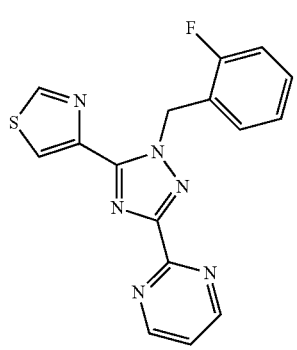

I-3

I-3: $^1$H NMR (CDCl$_3$/400 MHz) δ 8.92 (d, 2H), 8.85 (dd, 1H), 8.48 (dd, 1H), 7.33 (td, 1H), 7.22-7.16 (m, 1H), 7.03-6.94 (m, 3H), 6.26 (s, 2H); MS m/z: 339.3 (M+1).

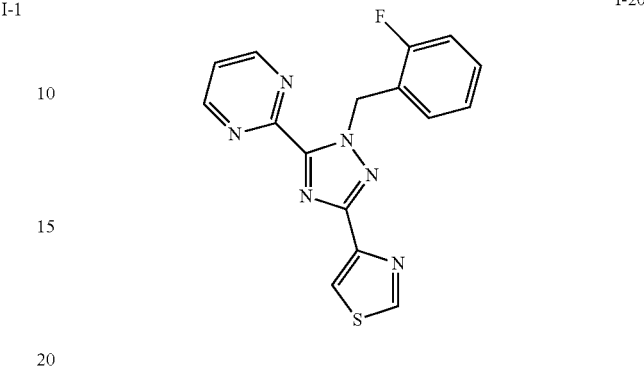

I-20

I-20: $^1$H NMR (CDCl$_3$/400 MHz) δ 8.91 (dd, 2H), 8.72 (br d, 1H), 8.27 (d, 1H), 7.36 (t, 1H), 7.23-7.17 (m, 1H), 7.11 (td, 1H), 7.04-6.95 (m, 2H), 6.24 (s, 2H); MS m/z: 339.3 (M+1).

Compounds I-4 and I-5

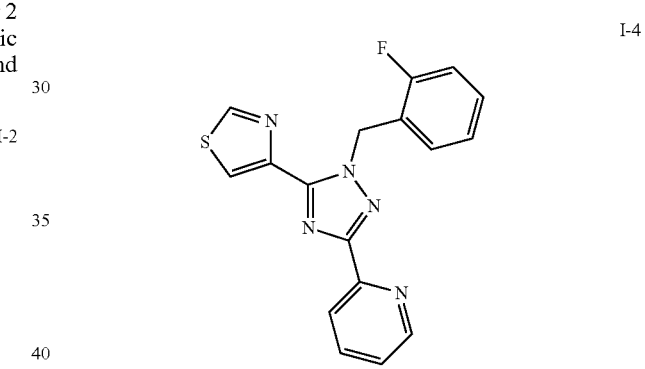

I-4

I-4: $^1$H NMR (CDCl$_3$/400 MHz) 8.86 (dd, 1H), 8.77-8.75 (m, 1H), 8.39 (dd, 1H), 8.21-8.18 (m, 1H), 7.81-7.76 (m, 1H), 7.33-7.30 (m, 1H), 7.25-7.18 (m, 1H), 7.06-6.97 (m, 3H), 6.20 (s, 2H); MS m/z: 338.3 (M+1).

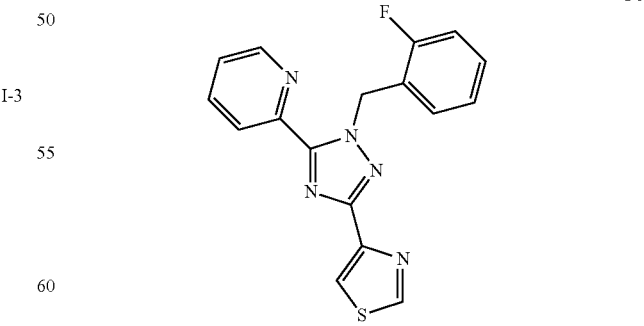

I-5

I-5: $^1$H NMR (CDCl$_3$/400 MHz) 8.92 (d, 1H), 8.64-8.62 (m, 1H), 8.36 (dt, 1H), 8.05 (d, 1H), 7.83 (td, 1H), 7.35-7.31 (m, 1H), 7.23-7.17 (m, 1H), 7.09 (td, 1H), 7.05-6.96 (m, 2H), 6.26 (s, 2H); MS m/z: 338.3 (M+1).

Compounds I-6 and I-7

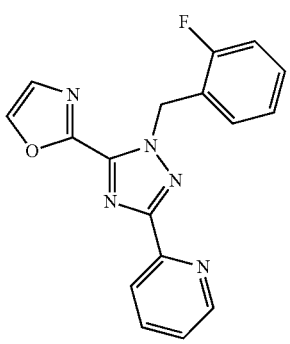

I-6: First eluting product: (Rf 0.51 in 15% (CH$_3$CN/MeOH [7/1])/DCM) (I-6) was obtained as a white solid (124.3 mg, 24%). $^1$H NMR (CDCl$_3$/400 MHz) δ 8.74-8.73 (m, 1H), 8.23 (d, 1H), 7.84 (d, 1H), 7.78 (td, 1H), 7.33-7.30 (m, 2H), 7.25-7.20 (m, 1H), 7.11 (td, 1H), 7.06-7.00 (m, 2H), 6.15 (s, 2H); MS m/z: 322.3 (M+1).

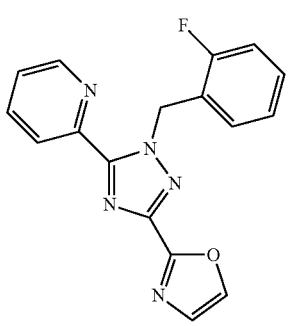

I-7: Second eluting product: (Rf 0.40 in 15% (CH$_3$CN/MeOH [7/1])/DCM) (I-7) was obtained as a white solid (132.7 mg, 26%). $^1$H NMR (CDCl$_3$/400 MHz) δ 8.64-8.62 (m, 1H), 8.40-8.37 (m, 1H), 7.85-7.80 (m, 1H), 7.78 (t, 1H), 7.36-7.32 (m, 1H), 7.32 (t, 1H), 7.23-7.17 (m 1H), 7.12-7.08 (m, 1H), 7.05-6.97 (m, 2H), 6.29 (s, 2H); MS m/z: 322.3 (M+1).

Compound I-11

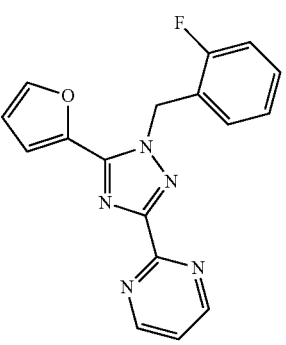

I-11: $^1$H NMR (CDCl$_3$/400 MHz) δ 8.90 (d, 2H), 7.53 (dd, 1H), 7.35 (t, 1H), 7.24-7.18 (m, 2H), 7.08-6.98 (m, 3H), 6.52 (dd, 1H), 6.21 (s, 2H); MS m/z: 322.3 (M+1).

Compound I-16 and Intermediate-1

I-16 and Intermediate-1 were synthesized as a white solid (49%) and an off-white solid (39%), respectively, following General Procedure A (step 2 only) and using commercially available 2-(5-bromo-1H-1,2,4-triazol-3-yl)pyridine and 2-fluorobenzyl bromide.

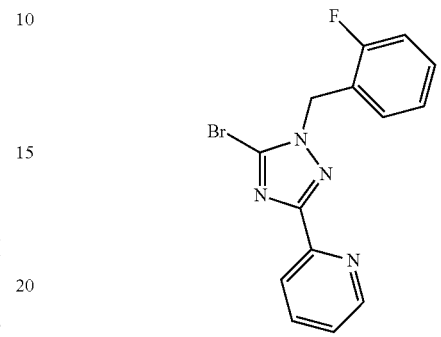

I-16: $^1$H NMR (400 MHz, CDCl$_3$) δ 8.73 (m, 1H), 8.11 (d, 1H), 7.79 (m, 1H), 7.35-7.29 (m, 2H), 7.22 (app. t, 1H), 7.13-7.08 (m, 2H), 5.54 (s, 2H) ppm. MS: [M+H]=333, 335 (bromine isotopes).

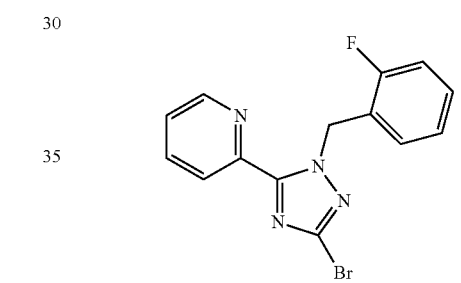

Intermediate 1: $^1$H NMR (400 MHz, CDCl$_3$) δ 8.64 (m, 1H), 8.21 (d, 1H), 7.84 (app. td, 1H), 7.36 (m, 1H), 7.25 (m, 1H), 7.14 (m, 1H), 7.06-7.01 (m, 2H), 6.18 (s, 2H) ppm. MS: [M+H]=333, 335 (bromine isotopes).

Compound I-21

Compound I-21 was synthesized as a white solid (16%) over 2 steps, following General Procedure A and using cyclopropanecarbohydrazide and 2-amidinopyridine hydrochloride in step 1 and 2-fluorobenzyl bromide in step 2.

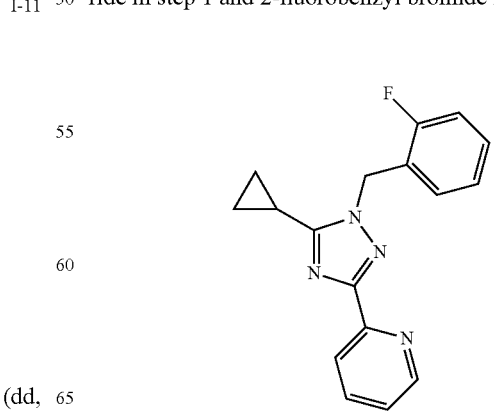

I-21: ¹H NMR (400 MHz, CDCl₃) δ 8.60 (br. d, 1H), 8.07 (d, 1H), 7.73 (app. td, 1H), 7.32-7.24 (m, 2H), 7.18 (app. t, 1H), 7.11-7.05 (m, 2H), 5.55 (s, 2H), 1.89 (m, 1H), 1.20 (m, 2H), 1.04 (m, 2H) ppm. MS: [M+H]=295.

Compound I-24

Compound I-24 was synthesized as a clear oil (17%, over 2 steps) following General Procedure A and using cyclobutanecarbohydrazide and 2-amidinopyridine hydrochloride in step 1 and 2-fluorobenzyl bromide in step 2. The other isomer was not isolated in this experiment.

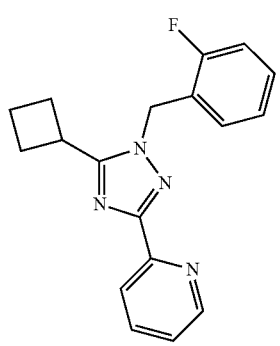

I-24

I-24: ¹H NMR (400 MHz, CDCl₃) δ 8.72 (m, 1H), 8.14 (d, 1H), 7.75 (app. td, 1H), 7.29-7.23 (m, 2H), 7.10-7.02 (m, 3H), 5.38 (s, 2H), 3.59 (app. pent., 1H), 2.54 (m, 2H), 2.27 (m, 2H), 2.07-1.93 (m, 2H) ppm. MS: [M+H]=309.

Compounds I-25 and I-26

Compounds I-25 and I-26 were synthesized as white solids (26% and 16%, respectively, over 2 steps) following General Procedure A and using thiazole-2-carboxylic acid hydrazide and 2-amidinopyridine hydrochloride in step 1 and 2-fluorobenzyl bromide in step 2.

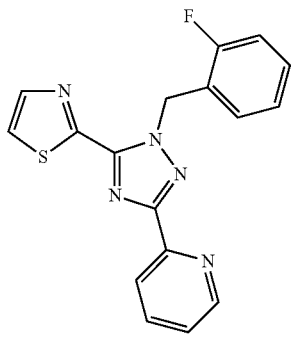

I-25

I-25: ¹H NMR (400 MHz, CDCl₃) δ 8.64 (m, 1H), 8.39 (d, 1H), 7.96 (m, 1H), 7.84 (m, 1H), 7.43 (m, 1H), 7.35 (m, 1H), 7.22 (m, 1H), 7.12 (app. t, 1H), 7.05-6.98 (m, 2H), 6.28 (s, 2H) ppm. MS: [M+H]=338.

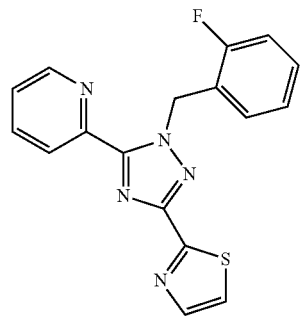

I-26

I-26: ¹H NMR (400 MHz, CDCl₃) δ 8.77 (m, 1H), 8.21 (d, 1H), 7.95 (d, 1H), 7.80 (app. td, 1H), 7.54 (d, 1H), 7.33 (m, 1H), 7.24 (m, 1H), 7.14-7.00 (m, 3H), 6.24 (s, 2H) ppm. MS: [M+H]=338.

Compound I-27

Compound I-27 was synthesized as a white solid (48% over 2 steps) following General Procedure A using benzoic hydrazide and 2-amidinopyrimidine hydrochloride in step 1 and 2-fluorobenzyl bromide in step 2.

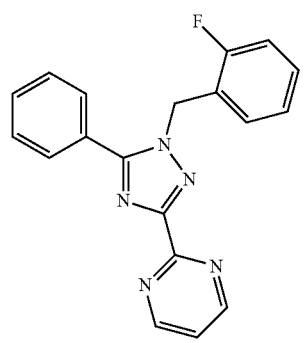

I-27

I-27: ¹H NMR (400 MHz, CDCl₃) δ 8.93 (d, 2H), 7.69 (m, 2H), 7.52-7.43 (m, 3H), 7.34 (app. t, 1H), 7.30 (m, 1H), 7.15-7.04 (m, 3H), 5.65 (s, 2H) ppm. MS: [M+H]=332.

Compound I-28

Compound I-28 was synthesized as a clear oil (48% over 2 steps) following General Procedure A and using acetic acid hydrazide and 2-amidinopyrimidine hydrochloride in step 1 and 2-fluorobenzyl bromide in step 2.

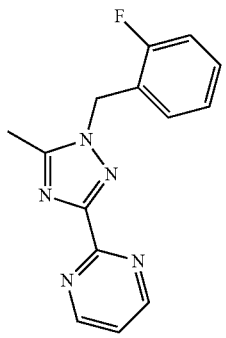

I-28

I-28: ¹H NMR (400 MHz, CDCl₃) δ 8.88 (d, 2H), 7.32-7.29 (m, 1H), 7.31 (app. t, 1H), 7.23-7.19 (m, 1H), 7.10-7.07 (m, 2H), 5.48 (s, 2H), 2.54 (s, 3H) ppm. MS: [M+H]=270.

Compounds I-29 and I-30

These two regioisomers, I-29 and I-30, were synthesized as a white solid (20%, I-30) and light yellow solid (26%, I-29)

over 2 steps, following General Procedure A and using thiazole-2-carboxylic acid hydrazide and 2-amidinopyrimidine hydrochloride in step 1 and 2-fluorobenzyl bromide in step 2.

I-29

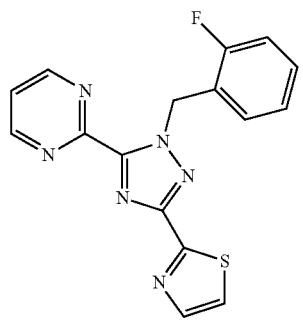

I-29: ¹H NMR (400 MHz, CDCl₃) δ 8.92 (d, 2H), 7.96 (d, 1H), 7.45 (d, 1H), 7.37 (app. t, 1H), 7.22-7.13 (m, 2H), 7.03-6.98 (m, 2H), 6.23 (s, 2H) ppm. MS: [M+H]=339.

I-30

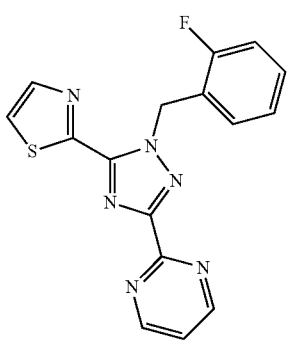

I-30: ¹H NMR (400 MHz, CDCl₃) δ 8.94 (d, 2H), 7.95 (d, 1H), 7.55 (d, 1H), 7.36 (app. t, 1H), 7.22 (m, 1H), 7.09-6.98 (m, 3H), 6.29 (s, 2H) ppm. MS: [M+H]=339.

Compounds I-31 and I-32

These regioisomers, I-31 and I-32, were synthesized as white solids (29% and 23% for I-31 and I-32, respectively, over 2 steps) following General Procedure A using picolinohydrazide and 2-amidinopyrimidine hydrochloride in step 1 and 2-fluorobenzyl bromide in step 2.

I-31

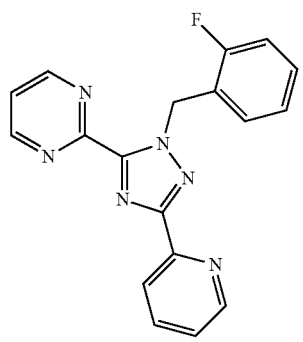

I-31: ¹H NMR (400 MHz, CDCl₃) δ 8.90 (d, 2H), 8.74 (m, 1H), 8.40 (d, 1H), 7.81 (app. td, 1H), 7.34 (app. t, 1H), 7.33 (m, 1H), 7.18 (m, 1H), 7.08 (app. br t, 1H), 7.03-6.95 (m, 2H), 6.27 (s, 2H) ppm. MS: [M+H]=333.

I-32

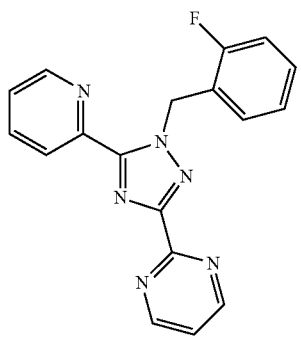

I-32: ¹H NMR (400 MHz, CDCl₃) δ 8.94 (d, 2H), 8.62 (m, 1H), 8.48 (d, 1H), 7.82 (app. td, 1H), 7.35 (app. t, 1H), 7.33 (m, 1H), 7.18 (m, 1H), 7.06-6.94 (m, 3H), 6.35 (s, 2H) ppm. MS: [M+H]=333.

Compounds I-58 and I-59

Step 2:

To a stirring solution of 3-(3-(pyridin-2-yl)-1H-1,2,4-triazol-5-yl)isoxazole hydrochloride (1 eq) in DMF was added sodium hydride (2.1 eq). After 10 minutes, 1-(bromomethyl)-2-fluorobenzene (1.1 eq) was added and the reaction was stirred overnight at room temperature. Brine was used to quench the reaction. Methylene chloride was used to extract the aqueous layer. The combined organic layers were washed with brine, dried over sodium sulfate and concentrated. SiO₂ chromatography yielded 3-(1-(2-fluorobenzyl)-3-(pyridin-2-yl)-1H-1,2,4-triazol-5-yl)isoxazole in 13.5% yield as a solid and 3-(1-(2-fluorobenzyl)-3-(pyrimidin-2-yl)-1H-1,2,4-triazol-5-yl)isoxazole in 15.7% yield as a solid.

I-58

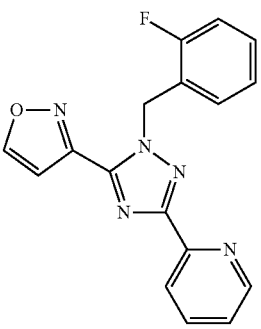

I-58: ¹H NMR (400 MHz, CDCl₃) 8.72-8.74 (m, 1H), 8.51 (d, 1H), 8.14 (td, 1H), 7.75 (dt, 1H), 7.28-7.31 (m, 1H), 7.19-7.24 (m, 1H), 7.13 (d, 1H), 6.97-7.09 (m, 3H), 6.02 (s, 2H).

I-59

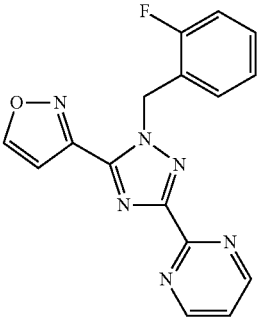

I-59: ¹H NMR (400 MHz, CDCl₃) 8.90-8.92 (m, 2H), 8.49-8.50 (m, 1H), 7.36 (t, 1H), 7.17-7.24 (m, 1H), 7.08-7.12 (m, 1H), 7.06-7.07 (m, 1H), 6.97-7.04 (m, 2H), 6.23 (s, 2H).

Compounds I-51 and 52

Step 2:

To a stirring solution of 4-(3-(4-bromopyridin-2-yl)-1H-1,2,4-triazol-5-yl)thiazole (1 eq) in DMF was added sodium hydride (2.1 eq). After 10 minutes, 1-(bromomethyl)-2-fluorobenzene (1.1 eq) was added and the reaction was stirred overnight at room temperature. Brine was used to quench the reaction. Methylene chloride was used to extract the aqueous layer. The combined organic layers were washed with brine, dried over sodium sulfate and concentrated. SiO₂ chromatography yielded 4-(3-(4-bromopyridin-2-yl)-1-(2-fluorobenzyl)-1H-1,2,4-triazol-5-yl)thiazole in 1% yield as a solid and 4-(5-(4-bromopyridin-2-yl)-1-(2-fluorobenzyl)-1H-1,2,4-triazol-3-yl)thiazole in 1% yield as a solid.

Compound I-54

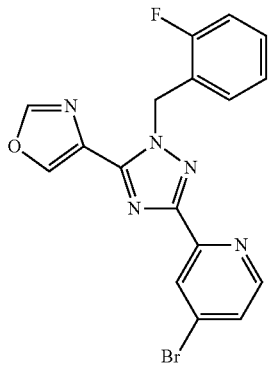

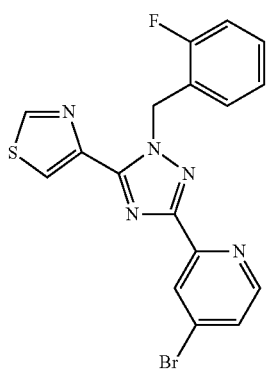

I-51: ¹H NMR (400 MHz, CDCl₃) 8.88 (d, 1H), 8.56 (d, 1H), 8.39-8.40 (m, 2H), 7.48-7.50 (m, 1H), 7.21-7.25 (m, 1H), 6.99-7.07 (m, 3H), 6.21 (s, 2H).

Step 2:

To a stirring solution of 4-(3-(4-bromopyridin-2-yl)-1H-1,2,4-triazol-5-yl)oxazole (1 eq) in DMF was added sodium hydride (2.1 eq). After 10 minutes, 1-(bromomethyl)-2-fluorobenzene (1.1 eq) was added and the reaction was stirred overnight at room temperature. Brine was used to quench the reaction. Methylene chloride was used to extract the aqueous layer. The combined organic layers were washed with brine, dried over sodium sulfate and concentrated. SiO₂ chromatography yielded 4-(3-(4-bromopyridin-2-yl)-1-(2-fluorobenzyl)-1H-1,2,4-triazol-5-yl)oxazole as a solid in 1% yield.

I-54: ¹H NMR (400 MHz, CDCl₃) 8.55 (dd, 1H), 8.50 (d, 1H), 8.36 (dd, 1H), 7.98 (d, 1H), 7.48 (dd, 1H), 7.22-7.28 (m, 1H), 7.00-7.14 (m, 3H), 6.10 (s, 2H).

Compounds I-45 and I-46

These were synthesized (white solids, 1.5% and 2.7% respectively over 2 steps) following General Procedure A using pyrimidine-2-carboximidamide hydrochloride and oxazole-4-carbohydrazide in step 1.

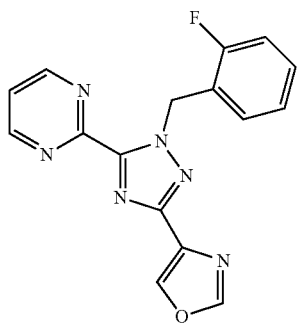

I-52: ¹H NMR (400 MHz, CDCl₃) 8.92 (d, 1H), 8.43 (d, 1H), 8.27 (d, 1H), 8.24 (s, 1H), 7.97 (dd, 1H), 7.27-7.28 (m, 1H), 7.03-7.11 (m, 3H), 6.15 (s, 2H).

I-45: ¹H NMR (400 MHz, CDCl₃) δ8.90 (d, 2H), 8.42 (s, 1H), 7.98 (s, 1H), 7.34 (t, 1H), 7.22-7.17 (m, 1H), 7.11-7.07 (m, 1H), 7.02-6.95 (m, 2H), 6.21 (s, 2H).

I-46: ¹H NMR (400 MHz, CDCl₃) δ 8.89 (d, 2H), 8.57 (s, 1H), 7.95 (s, 1H), 7.32 (t, 1H), 7.23-7.17 (m, 1H), 7.03-6.95 (m, 3H), 6.16 (s, 2H).

Example 4

I-15, I-18, I-19, I-36, I-37, I-38, I-39, I-40, I-41, I-55, I-56, I-62 and I-63

Compounds I-15, I-18, I-19, I-36, I-37, I-38, I-39, I-40, I-41, I-55, I-56, I-62 and I-63 were synthesized following General Procedure B described above according to the following conditions.

Step 1: Amidine Formation:

Nitrile F was treated with sodium methoxide (0.5 M in methanol, 0.5 eq) at room temperature and the reaction monitored by LC/MS analysis. Once the starting nitrile was consumed (reaction time was typically 2-7 h), ammonium chloride (1.1 eq) was added and the reaction mixture was stirred for 16-24 h. The reaction mixture was concentrated and dried in vacuo resulting in the amidine B. In some case, the crude amidine was collected by filtration. The crude amidine was carried on as described in General Procedure A without any further purification to yield products D and E.

Compound I-15

Compound I-15 was synthesized as a light yellow solid (33% over 3 steps) following General Procedure B and using 2-cyanothiazole in step 1. The subsequent steps were performed as described following General Procedure A, using thiazole-2-carboxylic acid hydrazide and 2-fluorobenzyl bromide in the respective steps.

I-15: ¹H NMR (400 MHz, CDCl₃) δ 7.97 (d, 2H), 7.56 (d, 1H), 7.44 (d, 1H), 7.26 (m, 1H), 7.16 (app. t, 1H), 7.09-7.02 (m, 2H), 6.22 (s, 2H) ppm. MS: [M+H]=344.

Compounds I-18 and I-19

Compounds I-19 and I-18 were synthesized as white solids (13% and 8%, respectively, over 3 steps) following General Procedure B and using 6-bromopicolinonitrile in step 1. The subsequent steps were performed as described following General Procedure A using thiazole-2-carboxylic acid hydrazide and 2-fluorobenzyl bromide in the respective steps.

I-18: ¹H NMR (400 MHz, CDCl₃) δ 8.35 (d, 1H), 7.97 (d, 1H), 7.70 (app. t, 1H), 7.53 (d, 1H), 7.44 (d, 1H), 7.24 (m, 1H), 7.16 (app. t, 1H), 7.08-7.00 (m, 2H), 6.20 (s, 2H) ppm. MS: [M+H]=416, 418 (bromine isotopes).

I-19: ¹H NMR (400 MHz, CDCl₃) δ 8.16 (d, 1H), 7.95 (m, 1H), 7.65 (app. t, 1H), 7.54 (m, 2H), 7.25 (m, 1H), 7.11-7.00 (m, 3H), 6.24 (s, 2H) ppm. MS: [M+H]=416, 418 (bromine isotopes).

Compounds I-36 and I-37

These compounds were synthesized (white solids, 33% and 24% yields, respectively, over 3 steps) following General Procedure B and using 4-bromopicolinonitrile in step 1. The subsequent steps were performed as described following General Procedure A using thiazole-2-carboxylic acid hydrazide and 2-fluorobenzyl bromide in the respective steps.

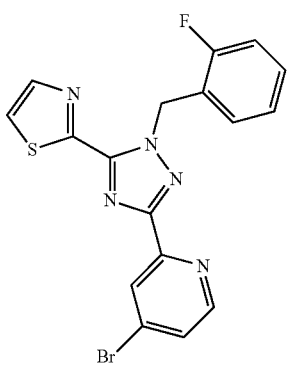

I-36

I-36: ¹H NMR (400 MHz, CDCl₃) δ 8.57 (d, 1H), 8.40 (d, 1H), 7.96 (d, 1H), 7.55 (d, 1H), 7.51 (dd, 1H), 7.26 (m, 1H), 7.14-7.01 (m, 3H), 6.24 (s, 2H) ppm. MS: [M+H]=416, 418 (bromine isotopes).

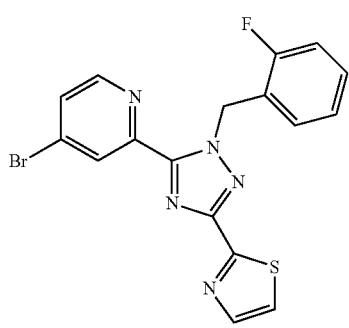

I-37

I-37: ¹H NMR (400 MHz, CDCl₃) δ 8.64 (d, 1H), 8.45 (d, 1H), 7.98 (d, 1H), 7.52 (dd, 1H), 7.45 (d, 1H), 7.23 (m, 1H), 7.12-6.99 (m, 3H), 6.25 (s, 2H) ppm. MS: [M+H]=416, 418 (bromine isotopes).

Compounds I-38 and I-39

These compounds were synthesized (white solids, 22% and 20% respectively over 3 steps) following General Procedure B using 5-fluoropicolinonitrile in step 1. The subsequent steps were performed as described following General Procedure A using thiazole-2-carboxylic acid hydrazide and 2-fluorobenzyl bromide in the respective steps.

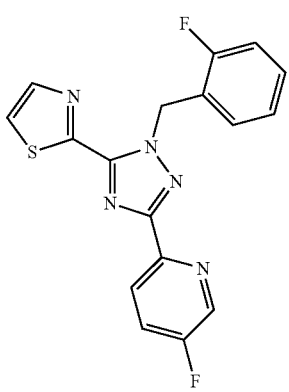

I-38

I-38: ¹H NMR (400 MHz, CDCl₃) δ 8.61 (d, 1H), 8.23 (dd, 1H), 7.96 (d, 1H), 7.54 (d, 1H), 7.51 (app. td, 1H), 7.25 (m, 1H), 7.14-7.00 (m, 3H), 6.23 (s, 2H) ppm. MS: [M+H]=356.

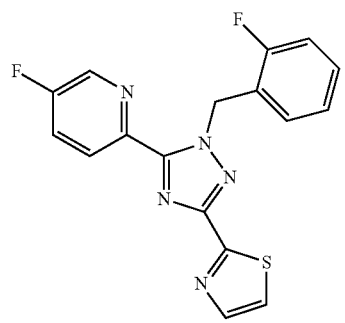

I-39

I-39: ¹H NMR (400 MHz, CDCl₃) δ 8.49 (d, 1H), 8.45 (dd, 1H), 7.97 (d, 1H), 7.55 (app. td, 1H), 7.44 (d, 1H), 7.23 (m, 1H), 7.12-6.98 (m, 3H), 6.21 (s, 2H) ppm. MS: [M+H]=356.

Compounds I-40 and I-41

These compounds were synthesized (off-white solids, 11% and 30% respectively over 3 steps) following General Procedure B using 2-cyanothiazole in step 1. The subsequent steps were performed as described following General Procedure A using thiazole-4-carboxylic acid hydrazide and 2-fluorobenzyl bromide in the respective steps.

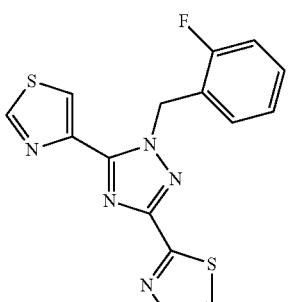

I-40

I-40: ¹H NMR (400 MHz, CDCl₃) δ 8.92 (d, 1H), 8.07 (d, 1H), 7.95 (d, 1H), 7.54 (d, 1H), 7.24 (m, 1H), 7.13 (app. t, 1H), 7.08-7.00 (m, 2H), 6.21 (s, 2H) ppm. MS: [M+H]=344.

I-41

I-41: ¹H NMR (400 MHz, CDCl₃) δ 8.89 (d, 1H), 8.39 (d, 1H), 7.96 (d, 1H), 7.43 (d, 1H), 7.24 (m, 1H), 7.12-6.89 (m, 3H), 6.19 (s, 2H) ppm. MS: [M+H]=344.

Compounds I-55 and I-56

These compounds were synthesized (off-white solids, 14% and 38% respectively over 3 steps) following General Procedure B using pyrazine-2-carbonitrile in step 1. The subsequent steps were performed as described following General Procedure A using thiazole-4-carboxylic acid hydrazide and 2-fluorobenzyl bromide in the respective steps.

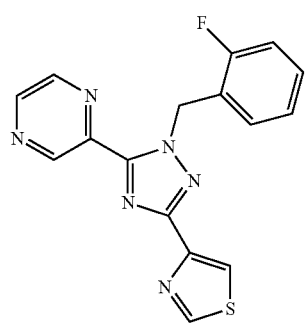

I-55

I-55: ¹H NMR (400 MHz, CDCl₃) δ 9.61 (d, 1H), 8.95 (d, 1H), 8.64 (d, 1H), 8.60 (dd, 1H), 8.10 (d, 1H), 7.23 (m, 1H), 7.12-6.98 (m, 3H), 6.19 (s, 2H) ppm. MS: [M+H]=339.

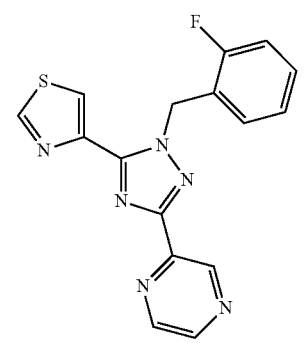

I-56

I-56: ¹H NMR (400 MHz, CDCl₃) δ 9.44 (d, 1H), 8.90 (d, 1H), 8.70 (dd, 1H), 8.61 (d, 1H), 8.41 (d, 1H), 7.25 (m, 1H), 7.11-7.00 (m, 3H), 6.23 (s, 2H) ppm. MS: [M+H]=339.

Compounds I-62 and I-63

These compounds were synthesized (tan solid, 3% and white solid, 5% respectively over 3 steps) following General Procedure B using oxazole-4-carbonitrile in step 1. The subsequent steps were performed as described following General Procedure A using thiazole-2-carboxylic acid hydrazide and 2-fluorobenzyl bromide in the respective steps.

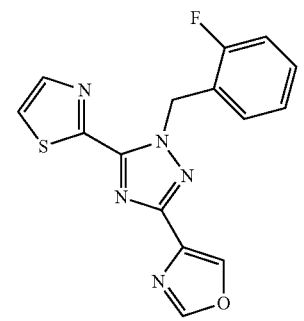

I-62

I-62: ¹H NMR (400 MHz, CDCl₃) δ 8.28 (s, 1H), 7.99 (s, 1H), 7.95 (d, 1H), 7.53 (d, 1H), 7.25 (m, 1H), 7.12 (app. t, 1H), 7.08-7.00 (m, 2H), 6.19 (s, 2H) ppm. MS: [M+H]=328.

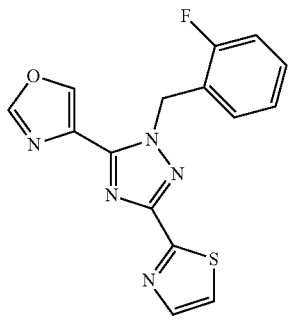

I-63

I-63: ¹H NMR (400 MHz, CDCl₃) δ 8.49 (s, 1H), 7.99 (s, 1H), 7.95 (d, 1H), 7.42 (d, 1H), 7.26 (m, 1H), 7.13-7.02 (m, 3H), 6.09 (s, 2H) ppm. MS: [M+H]=328.

Example 5

Compound I-23

This compound was prepared according to General Procedure C.

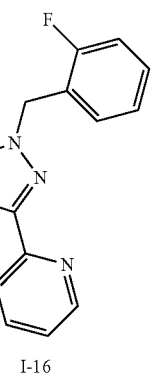

I-16

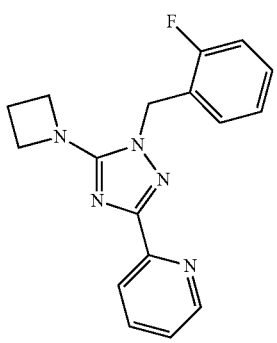

I-23

A solution of 2-(5-bromo-1-(2-fluorobenzyl)-1H-1,2,4-triazol-3-yl)pyridine (I-16), in DMA was treated with a large excess of azetidine (~30 eq). The resultant solution was warmed to 100° C. and stirred at that temperature for 18 h. The reaction solution was cooled to rt, poured into 1N NaOH solution and then extracted with EtOAc. The organic phases were dried over Na₂SO₄, filtered and conc. The crude product was purified using SiO₂ chromatography and an appropriate gradient (MeOH—CH₃CN (1:7)/CH₂Cl₂) to give 2-(5-(azetidin-1-yl)-1-(2-fluorobenzyl)-1H-1,2,4-triazol-3-yl)pyridine, I-23, as a white solid (88% yield).

I-23: ¹H NMR (400 MHz, CDCl₃) δ 8.70 (m, 1H), 8.06 (m, 1H), 7.73 (m, 1H), 7.29-7.23 (m, 2H), 7.16-7.03 (m, 3H), 5.26 (s, 2H), 4.13 (t, 4H), 2.34 (pent., 2H) ppm. MS: [M+H]=310.

Example 6

Compounds I-10, I-17, I-67, I-49 and I-50

Compounds I-10, I-17, I-67, I-49 and I-50 were prepared with General Procedure D.

Compound I-10

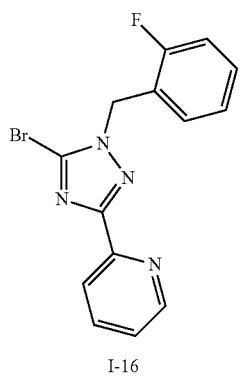

I-16

Pyrazole, NaH
DMF
50°C.

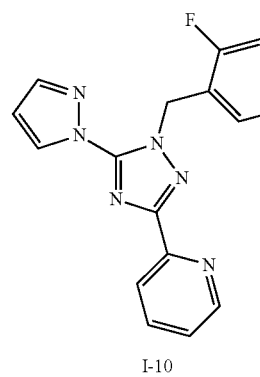

I-10

A solution of pyrazole (1.1 eq) in DMF was treated with sodium hydride (60% w/w in mineral oil, 1.2 eq) and stirred for 10 min at room temperature. 2-(5-Bromo-1-(2-fluorobenzyl)-1H-1,2,4-triazol-3-yl)pyridine (I-16, 1.0 eq) was then added. The resultant mixture was warmed to 50° C. and stirred at that temperature for 1 h. The reaction solution was cooled to rt, poured into water, and filtered to give 2-(1-(2-fluorobenzyl)-5-(1H-pyrazol-1-yl)-1H-1,2,4-triazol-3-yl) pyridine, I-10, as a white solid (84% yield).

I-10: ¹H NMR (400 MHz, CDCl₃) δ 8.76 (br. d, 1H), 8.43 (d, 1H), 8.15 (d, 1H), 7.79 (app. td, 1H), 7.77 (br. s, 1H), 7.33 (m, 1H), 7.24 (m, 1H), 7.14 (app. t, 1H), 7.06-7.01 (m, 2H), 6.50 (m, 1H), 6.07 (s, 2H) ppm. MS: [M+H]=321.

Compound I-17

Compound I-17 was synthesized as an off-white solid (12% yield) from 2-(3-bromo-1-(2-fluorobenzyl)-1H-1,2,4-triazol-5-yl)pyridine (Intermediate 1). In this experiment, the temperature was raised to 140° C. and additional equivalents of pyrazole and sodium hydride were added during the reaction.

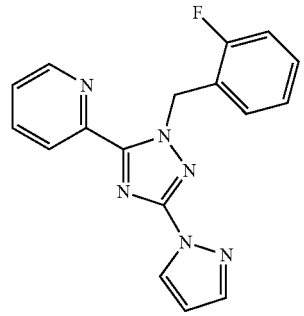

I-17

I-17: ¹H NMR (400 MHz, CDCl₃) δ 8.65 (br. d, 1H), 8.34 (d, 1H), 8.28 (d, 1H), 7.85 (app. td, 1H), 7.78 (m, 1H), 7.36 (m, 1H), 7.23 (m, 1H), 7.17 (app. t, 1H), 7.06-7.00 (m, 2H), 6.46 (m, 1H), 6.23 (s, 2H) ppm. MS: [M+H]=321.

Compound I-67 (A+B mixture)

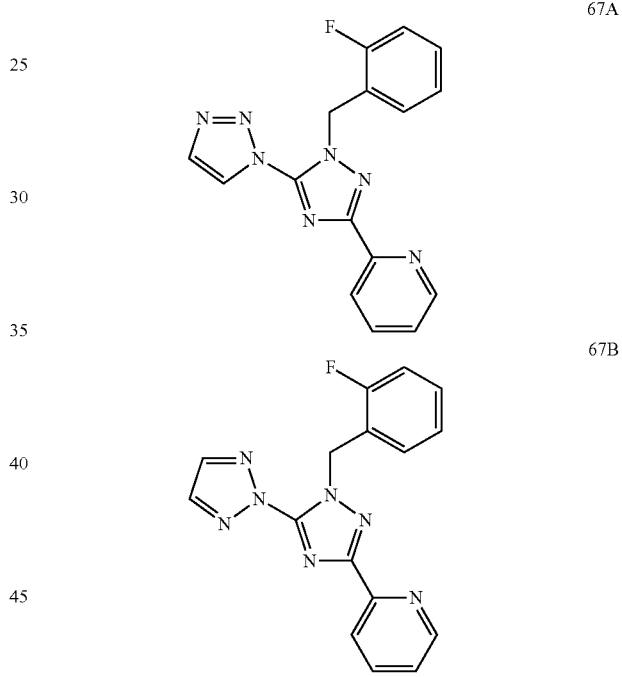

1,2,3-triazole (1.8 eq) was stirred in a vial in DMF. Sodium hydride (2.5 eq) was added and this mixture was stirred for 20 minutes. 2-(5-bromo-1-(2-fluorobenzyl)-1H-1,2,4-triazol-3-yl)pyridine (I-16) was added and the reaction mixture was stirred at 100° C. for 12 hr. Brine was poured into the reaction mixture. The aqueous layer was extracted with ethyl acetate, dried over sodium sulfate and concentrated. Two isomers were generated, which were purified together by SiO₂ chromatography. Both isomers were characterized as 2-(1-(2-fluorobenzyl)-5-(1H-1,2,3-triazol-1-yl)-1H-1,2,4-triazol-3-yl)pyridine and 2-(1-(2-fluorobenzyl)-5-(2H-1,2,3-triazol-2-yl)-1H-1,2,4-triazol-3-yl)pyridine in 47.1% yield. They seem to be present in a 3:1 mixture although it is difficult to tell which compound is in the majority.

I-67 (A+B): ¹H NMR (400 MHz, CDCl₃) 8.75-8.78 (m, 1H), 8.5 (d, 0.3H), 8.26-8.28 (m, 1H), 8.14-8.16 (m, 0.3H), 7.88 (d, 0.3H), 7.8-7.84 (m, 1.3H), 7.34-7.39 (m, 1.3H), 7.15-7.24 (m, 2H), 6.99-7.08 (m, 2.5H), 6.02 (s, 1H), 5.97 (s, 2H).

Compound I-49

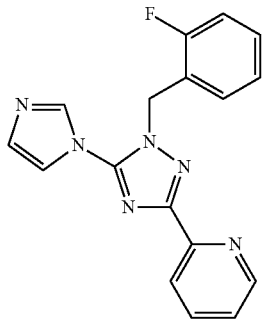

To a stirring suspension of imidazole (1.2 eq) in DMF was added sodium hydride (2 eq). The reaction generated gas and was stirred for 10 minutes. Then 2-(5-bromo-1-(2-fluorobenzyl)-1H-1,2,4-triazol-3-yl)pyridine (I-16) was added. The reaction was stirred at 100° C. for 12 hr. The reaction was quenched with brine, extracted with methylene chloride, dried over sodium sulfate and concentrated. The mixture was purified by SiO$_2$ chromatography to afford 2-(1-(2-fluorobenzyl)-5-(1H-imidazol-1-yl)-1H-1,2,4-triazol-3-yl)pyridine as a solid in 26.7% yield.

I-49: $^1$H NMR (400 MHz, CDCl$_3$) 8.75-8.77 (m, 1H), 8.13-8.16 (m, 1H), 7.90 (s, 1H), 7.82 (dt, 1H), 7.31-7.38 (m, 2H), 7.28-7.29 (m, 1H), 7.23-7.24 (m, 1H), 7.18-7.20 (m, 1H), 7.07-7.15 (m, 2H), 5.50 (s, 2H).

Compound I-50

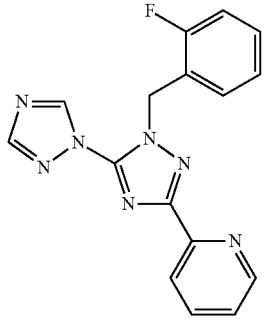

To a stirring suspension of 1,2,3-triazole (1.8 eq) in DMF was added sodium hydride (2.5 eq). The reaction generated gas and was stirred for 10 minutes. Then 2-(5-bromo-1-(2-fluorobenzyl)-1H-1,2,4-triazol-3-yl)pyridine (I-16) was added. The reaction was stirred at 100° C. for 12 hr. The reaction was quenched with brine, extracted with methylene chloride, dried over sodium sulfate and concentrated. The mixture was purified by SiO$_2$ chromatography to afford 2'-(2-fluorobenzyl)-5'-(pyridin-2-yl)-2'H-1,3'-bi(1',2',4-triazole) in 17.3% yield.

I-50: $^1$H NMR (400 MHz, CDCl$_3$) 9.05 (s, 1H), 8.76 (d, 1H), 8.17 (s, 1H), 8.14 (d, 1H), 7.81 (dt, 1H), 7.34-7.37 (m, 1H), 7.24-7.30 (m, 1H), 7.16-7.20 (m, 1H), 7.02-7.07 (m, 2H), 5.98 (s, 2H).

Example 7

Compounds I-33 and I-34

Compounds I-33 and I-34 were prepared in accordance with General Procedure E.

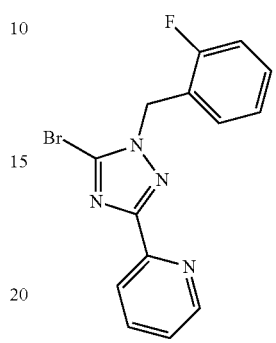

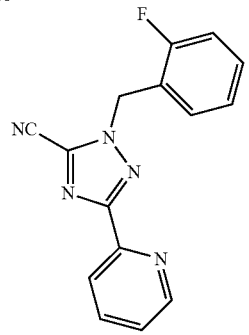

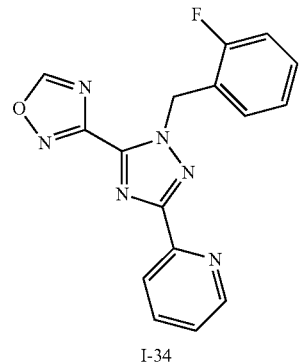

Compound I-33

To a solution of 2-(5-bromo-1-(2-fluorobenzyl)-1H-1,2,4-triazol-3-yl)pyridine (I-16, 0.95 g, 2.9 mmol) in N,N-dimethylformamide (9.5 mL) was added potassium cyanide (0.928 g, 14.3 mmol). After heating the solution at 100° C. for 22 h, the solution was diluted with ethyl acetate (125 mL) and water (100 mL). The layers were separated, and the aqueous layer was extracted with ethyl acetate (2×50 mL). The organics were combined, washed with water (50 mL) and brine (50 mL), dried over magnesium sulfate, filtered, and the solvent was removed in vacuo to give the crude product as an orange oil. Purification by silica gel chromatography (0-15% ethyl acetate in dichloromethane) gave 1-(2-fluorobenzyl)-3-(pyridin-2-yl)-1H-1,2,4-triazole-5-carbonitrile, I-33 (250 mg, 0.90 mmol, 31% yield) as a white solid.

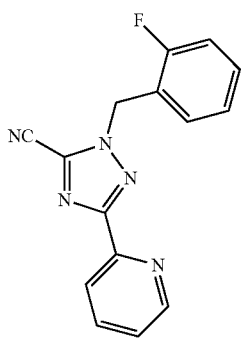

I-33

I-33: ¹H NMR (400 MHz, CDCl₃) δ 8.67-8.65 (m, 1H), 8.06-8.03 (m, 1H), 7.73 (dt, 1H), 7.37-7.27 (m, 3H), 7.12-7.02 (m, 2H), 5.60 (s, 2H).

Compound I-34

To a solution of 1-(2-fluorobenzyl)-3-(pyridin-2-yl)-1H-1,2,4-triazole-5-carbonitrile (I-33, 100 mg, 0.358 mmol) and potassium carbonate (198 mg, 1.43 mmol) in methanol (3.6 mL) was added hydroxylamine hydrochloride (75 mg, 1.1 mmol). The solution was heated at 70° C. for 1.25 h, at which point the solution was diluted with ethyl acetate (20 mL) and the solids were filtered off through a cotton plug. The solvent was removed in vacuo and the crude residue was diluted with water (50 mL) and a 5:1 mixture of dichloromethane and 2-propanol (50 mL). The layers were separated and the organic layer was washed with water (50 mL), dried over magnesium sulfate, and the solvent was removed in vacuo. To the resulting crude 1-(2-fluorobenzyl)-N'-hydroxy-3-(pyridin-2-yl)-1H-1,2,4-triazole-5-carboximidamide was added trimethyl orthoformate (4.5 mL, 41 mmol) and a catalytic amount of p-toluenesulfonic acid monohydrate (3.4 mg, 0.018 mmol). The solution was heated at 100° C. for 1.5 h, and the excess orthoformate was removed in vacuo to give the crude product as a dull yellow solid. Purification by silica gel chromatography (20-80% ethyl acetate in hexanes) gave 3-(1-(2-fluorobenzyl)-3-(pyridin-2-yl)-1H-1,2,4-triazol-5-yl)-1,2,4-oxadiazole, I-34 (52 mg, 0.16 mmol, 46% yield over 2 steps) as a white solid.

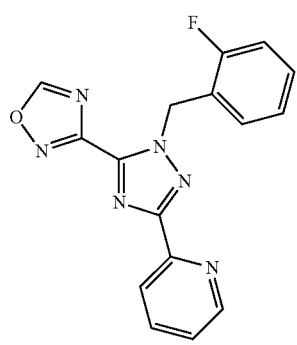

I-34

I-34: ¹H NMR (400 MHz, CDCl₃) δ 8.98 (s, 1H), 8.73-8.72 (m, 1H), 8.29-8.27 (m, 1H), 7.79 (dt, 1H), 7.34-7.31 (m, 1H), 7.26-7.20 (m, 1H), 7.12-7.08 (m, 1H), 7.03-6.99 (m, 2H), 6.05 (s, 2H).

Example 8

I-14, I-22, I-44, I-47, I-64, I-65, I-66, I-53, I-68

Compounds I-14, I-22, I-44, I-47, I-64, I-65, I-66, I-53, I-68 were prepared with General Procedure F.

Compound I-14

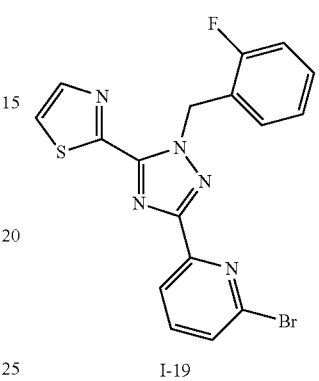

I-19

NH₄OH, Cu₂O
ethylene glycol-dioxane (4:1)
100°C.

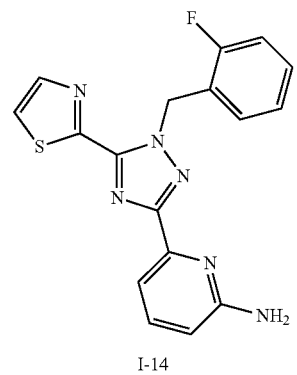

I-14

To a suspension of 2-(3-(6-bromopyridin-2-yl)-1-(2-fluorobenzyl)-1H-1,2,4-triazol-5-yl)thiazole (I-19) and copper(I) oxide (0.2 eq) in ethylene glycol-dioxane (4:1) in a sealed tube was added ammonium hydroxide solution (~29% in water, ~30 eq). The resultant mixture was warmed to 100° C. and stirred at that temperature for 24 h. The reaction solution was cooled to rt, poured into 1N NaOH solution and then extracted with EtOAc. The organic phases were dried over Na₂SO₄, filtered and conc. The crude product was purified using SiO₂ chromatography and an appropriate gradient (EtOAc/hexanes) to give 6-(1-(2-fluorobenzyl)-5-(thiazol-2-yl)-1H-1,2,4-triazol-3-yl)pyridin-2-amine as a white solid (I-14, 69% yield).

I-14: ¹H NMR (400 MHz, CDCl₃) δ 7.92 (d, 1H), 7.59 (d, 1H), 7.55 (app. t, 1H), 7.14 (d, 1H), 7.22 (m, 1H), 7.07-6.98 (m, 3H), 6.56 (d, 1H), 6.22 (s, 2H), 4.74 (br. s, 2H) ppm. MS: [M+H]=353.

Compound I-22

Compound I-22 was synthesized following General Procedure F as a white solid (81% yield) from 2-(5-(6-bromopyridin-2-yl)-1-(2-fluorobenzyl)-1H-1,2,4-triazol-3-yl)thiazole (I-18).

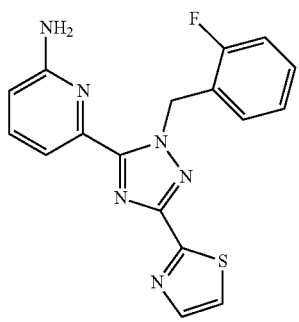

I-22

I-22: ¹H NMR (400 MHz, CDCl₃) δ 7.96 (d, 1H), 7.73 (d, 1H), 7.54 (app. t, 1H), 7.43 (d, 1H), 7.22 (m, 1H), 7.14 (m, 1H), 7.09-6.99 (m, 2H), 6.52 (d, 1H), 6.19 (s, 2H), 4.50 (br. s, 2H) ppm. MS: [M+H]=353.
Compound I-44

I-44

This compound was synthesized as a pale green solid (73% yield) from 2-(3-(4-bromopyridin-2-yl)-1-(2-fluorobenzyl)-1H-1,2,4-triazol-5-yl)thiazole (I-36).

¹H NMR (400 MHz, CDCl₃) δ 8.37 (m, 1H), 7.93 (d, 1H), 7.52 (d, 1H), 7.47 (m, 1H), 7.23 (m, 1H), 7.13-6.98 (m, 3H), 6.56 (m, 1H), 6.22 (s, 2H), 4.24 (br. s, 2H) ppm. MS: [M+H]=353.
Compound I-47

I-47

This was synthesized as a white solid (81% yield) from 2-(5-(4-bromopyridin-2-yl)-1-(2-fluorobenzyl)-1H-1,2,4-triazol-3-yl)thiazole (I-37).

I-47: ¹H NMR (400 MHz, CDCl₃) δ 8.24 (d, 1H), 7.95 (d, 1H), 7.65 (d, 1H), 7.41 (d, 1H), 7.21 (m, 1H), 7.11 (app. t, 1H), 7.06-6.98 (m, 2H), 6.56 (dd, 1H), 6.29 (s, 2H), 4.28 (br. s, 2H) ppm. MS: [M+H]=353.
Compound I-64

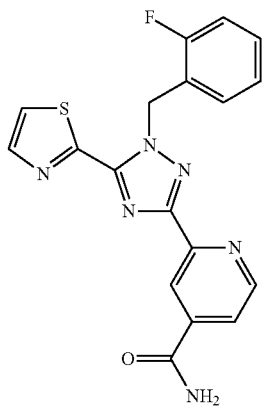

I-64

To a stirring suspension of 2-(3-(4-bromopyridin-2-yl)-1-(2-fluorobenzyl)-1H-1,2,4-triazol-5-yl)thiazole (I-36, 1 equiv) in ethylene glycol-dioxane (approx. 4:1) in a sealed tube was added copper(I) cyanide (3 equiv). The resultant reaction mixture was heated at 100° C. for 24 hr and then cooled to room temperature, treated with brine and extracted with ethyl acetate. The combined organic layers were dried over sodium sulfate, concentrated and purified using SiO₂ chromatography (ethyl acetate/hexanes) to afford 2-(1-(2-fluorobenzyl)-5-(thiazol-2-yl)-1H-1,2,4-triazol-3-yl)isonicotinamide as a solid in 11% yield.

I-64: ¹H NMR (400 MHz, CDCl₃) 8.91 (d, 1H), 8.44 (s, 1H), 7.96 (d, 1H), 7.56 (d, 1H), 7.53-7.55 (m, 1H), 7.03-7.13 (m, 3H), 6.23 (s, 2H).
Compound I-65

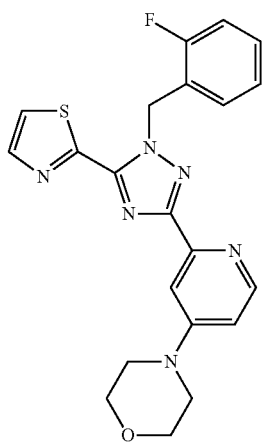

I-65

To a stirring suspension of 2-(3-(4-bromopyridin-2-yl)-1-(2-fluorobenzyl)-1H-1,2,4-triazol-5-yl)thiazole (I-36, 1 eq) and copper(I) oxide (1 eq) in ethylene glycol-dioxane (approx. 4:1) in a sealed tube is added morpholine (30 eq). The resultant reaction mixture was heated at 100° C. for 12 hr. The reaction was cooled to room temperature and treated with brine and then extracted with ethyl acetate. The combined organic layers were dried over sodium sulfate, concentrated and purified using SiO₂ chromatography (methylene chloride/acetonitrile/methanol) to afford 4-(2-(1-(2-fluorobenzyl)-5-(thiazol-2-yl)-1H-1,2,4-triazol-3-yl)pyridin-4-yl)morpholine as a solid in 79% yield.

I-65: ¹H NMR (400 MHz, CDCl₃) 8.42 (d, 1H), 7.90 (d, 1H), 7.59 (d, 1H), 7.49 (d, 1H), 7.17-7.23 (m, 1H), 6.95-7.05 (m, 3H), 6.66-6.69 (m, 1H), 6.19 (s, 2H), 3.82-3.85 (m, 4H), 3.36-3.39 (m, 4H).

Compound I-66

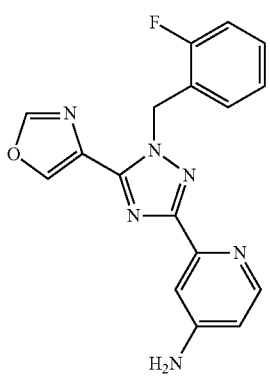

I-66

To a stirring suspension of 4-(3-(4-bromopyridin-2-yl)-1-(2-fluorobenzyl)-1H-1,2,4-triazol-5-yl)oxazole (I-54, 1 eq) and copper(I) oxide (0.2 eq) in ethylene glycol-dioxane (approx. 4:1) in a sealed tube was added ammonium hydroxide (30 eq). The resultant reaction mixture was heated at 100° C. for 12 hr. The reaction was cooled to room temperature and treated with brine and extracted with ethyl acetate. The combined organic layers were dried over sodium sulfate, concentrated and purified using SiO₂ chromatography (DCM/CAN/MeOH) to afford 2-(1-(2-fluorobenzyl)-5-(oxazol-4-yl)-1H-1,2,4-triazol-3-yl)pyridin-4-amine in 41.2% yield.

I-66: ¹H NMR (400 MHz, CDCl₃) 8.47 (d, 1H), 8.34 (d, 1H), 7.96 (d, 1H), 7.42 (d, 1H), 7.20-7.24 (m, 1H), 6.98-7.10 (m, 3H), 6.55 (dd, 1H), 6.06 (s, 2H).

Compound I-68

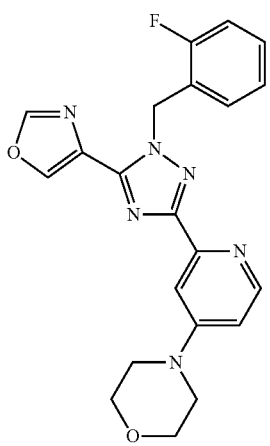

I-68

To a stirring suspension of 4-(3-(4-bromopyridin-2-yl)-1-(2-fluorobenzyl)-1H-1,2,4-triazol-5-yl)oxazole (I-54, 1 eq) and copper(I) oxide (1 eq) in ethylene glycol-dioxane (approx. 4:1) in a sealed tube was added morpholine (30 eq). The resultant reaction mixture was heated at 100° C. for 12 hr and then cooled to room temperature, treated with brine and extracted with ethyl acetate. The combined organic layers were dried over sodium sulfate, concentrated and purified using SiO₂ chromatography (methylene chloride/acetonitrile/methanol) to afford 4-(2-(1-(2-fluorobenzyl)-5-(oxazol-4-yl)-1H-1,2,4-triazol-3-yl)pyridin-4-yl)morpholine in 10.3% yield.

I-68: ¹H NMR (400 MHz, CDCl₃) 8.51 (d, 1H), 8.47 (d, 1H), 7.96 (d, 1H), 7.58 (d, 1H), 7.21-7.25 (m, 1H), 7.00-7.07 (m, 3H), 6.71-6.74 (m, 1H), 6.08 (s, 2H), 3.85-3.87 (m, 4H), 3.42-3.45 (m, 4H).

Compound I-53

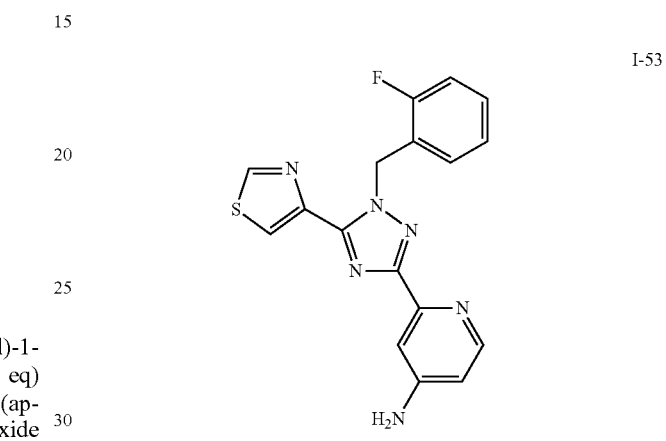

I-53

To a stirring suspension of 4-(3-(4-bromopyridin-2-yl)-1-(2-fluorobenzyl)-1H-1,2,4-triazol-5-yl)thiazole (I-51, 1 eq) and copper(I) oxide (1 eq) in ethylene glycol-dioxane (approx. 4:1) in a sealed tube was added ammonium hydroxide. The resultant reaction mixture was heated at 100° C. for 12 h and then cooled to room temperature, treated with brine and extracted with ethyl acetate. The combined organic layers were dried over sodium sulfate, concentrated and purified using SiO₂ chromatography (methylene chloride/acetonitrile/methanol) to afford 2-(1-(2-fluorobenzyl)-5-(thiazol-4-yl)-1H-1,2,4-triazol-3-yl)pyridin-4-amine as a solid in 59.6% yield.

I-53: ¹H NMR (400 MHz, CDCl₃) 8.87 (s, 1H), 8.38 (s, 1H), 8.34 (d, 1H), 7.46 (s, 1H), 7.23-7.25 (m, 1H), 7.01-7.06 (m, 3H), 6.63 (d, 1H), 6.18 (s, 2H), 4.69 (br. s, 2H).

Example 9

The following compounds were prepared as described in each case.

Compounds I-43 and I-48 and Intermediates 2, 3, 4, 5 and 6

Step 1:

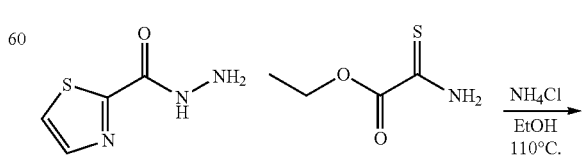

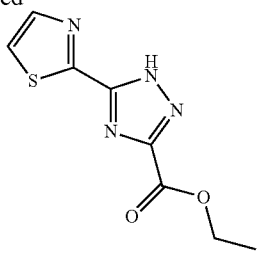

Intermediate-2

A suspension of thiazole-2-carbohydrazide (4.2 mmol), ethyl 2-amino-2-thioxoacetate (1 equiv) and ammonium chloride (6 equiv) in ethanol (150 mL) was placed in a sealed tube and this was warmed to 110° C. and stirred at that temperature for 11 days. The reaction solution was cooled to rt and conc. Brine was added and the mixture was adjusted to pH-6 and extracted with EtOAc. The organic phases were dried over $Na_2SO_4$, filtered and conc. The crude product was purified using $SiO_2$ chromatography and an appropriate solvent gradient ($CH_3CN/MeOH/CH_2Cl_2$) to give ethyl 3-(thiazol-2-yl)-1H-1,2,4-triazole-5-carboxylate as an off-white solid (Intermediate-2, 37% yield).

Step 2:

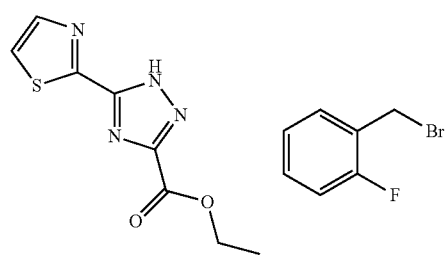

Intermediate-2

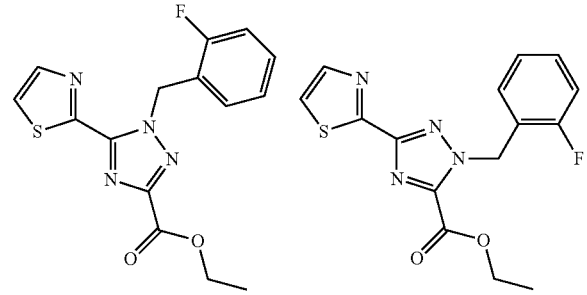

Intermediate-3  I-43

To a solution of ethyl 3-(thiazol-2-yl)-1H-1,2,4-triazole-5-carboxylate (Intermediate-2, 1.7 mmol) in DMF (8 mL) was added sodium hydride (1.2 equiv). After 10 min, 1-(bromomethyl)-2-fluorobenzene (1.2 equiv) was added. The reaction was stirred at ambient temperature for 35 min. The reaction mixture was poured into water and extracted with EtOAc. The organic phases were washed with water and brine, dried over $Na_2SO_4$, filtered and conc. The crude product was purified using $SiO_2$ chromatography and an appropriate solvent gradient (EtOAc/hexanes) to give ethyl 1-(2-fluorobenzyl)-5-(thiazol-2-yl)-1H-1,2,4-triazole-3-carboxylate (48%) and ethyl 1-(2-fluorobenzyl)-3-(thiazol-2-yl)-1H-1,2,4-triazole-5-carboxylate as white solids (44% yield).

Intermediate-3: Ethyl 1-(2-fluorobenzyl)-5-(thiazol-2-yl)-1H-1,2,4-triazole-3-carboxylate $^1$H NMR (400 MHz, $CDCl_3$) δ 7.96 (d, 1H), 7.57 (d, 1H), 7.25 (m, 1H), 7.10-7.00 (m, 3H), 6.22 (s, 2H), 4.51 (q, 2H), 1.45 (t, 3H) ppm. MS: [M+H]=333.

I-43: Ethyl 1-(2-fluorobenzyl)-3-(thiazol-2-yl)-1H-1,2,4-triazole-5-carboxylate $^1$H NMR (400 MHz, $CDCl_3$) δ 7.96 (d, 1H), 7.46 (d, 1H), 7.29 (m, 1H), 7.19 (app. t, 1H), 7.11-7.05 (m, 2H), 5.97 (s, 2H), 4.49 (q, 2H), 1.43 (t, 3H) ppm. MS: [M+H]=333.

Step 3:

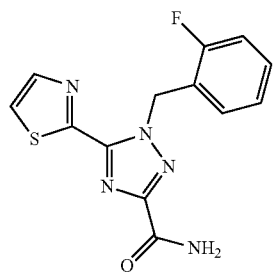

Intermediate-3

A solution of ethyl 1-(2-fluorobenzyl)-5-(thiazol-2-yl)-1H-1,2,4-triazole-3-carboxylate (Intermediate-3, 0.78 mmol) and sodium cyanide (0.1 equiv) in ammonia/MeOH (7N, 30 equiv, 3.4 mL) in a seal tube was heated at 90° C. for 24 h. The reaction mixture was cooled to room temperature, conc. and dried in vacuo to afford 1-(2-fluorobenzyl)-5-(thiazol-2-yl)-1H-1,2,4-triazole-3-carboxamide as a tan solid (>99% yield).

Step 4:

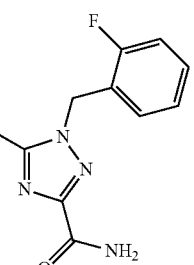

Intermediate-4

-continued

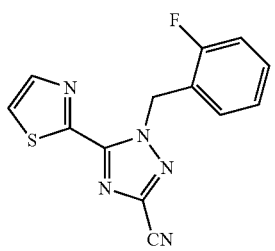

Intermediate-5

A solution of 1-(2-fluorobenzyl)-5-(thiazol-2-yl)-1H-1,2,4-triazole-3-carboxamide (Intermediate-4, 0.86 mmol) in pyridine (3.0 mL) at 0° C. was treated with trifluoroacetic anhydride (2 equiv) dropwise over the course of 5 min. The reaction was then warmed to ambient temperature and stirred for 2 h. The reaction mixture was poured into saturated NaHCO₃ solution and extracted with CH₂Cl₂. The organic phases were dried over MgSO₄, filtered and conc. The crude product was purified using SiO₂ chromatography and an appropriate solvent gradient (EtOAc/hexanes) to give 1-(2-fluorobenzyl)-5-(thiazol-2-yl)-1H-1,2,4-triazole-3-carbonitrile as white solid (88% yield).

Step 5:

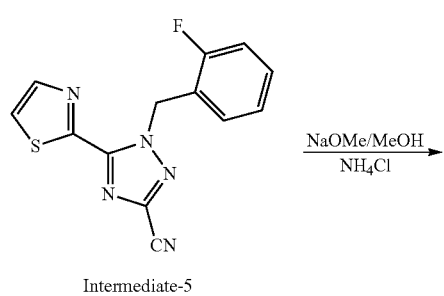

Intermediate-6

To 1-(2-fluorobenzyl)-5-(thiazol-2-yl)-1H-1,2,4-triazole-3-carbonitrile (Intermediate-5, 0.74 mmol) was added sodium methoxide/MeOH (0.5M, 4 equiv, 5.9 mL). After stirring at ambient temperature for 3 h, additional portion of sodium methoxide/MeOH (1 equiv) was added. After 2 h, ammonium chloride (10 equiv) was added and the resultant mixture was stirred at ambient for 17 h. The reaction mixture was conc. Half-saturated NaHCO₃/1N NaOH solution (10:1) was added and the aqueous mixture was extracted with EtOAc. The organic phases were dried over Na₂SO₄, filtered and conc. to afford 1-(2-fluorobenzyl)-5-(thiazol-2-yl)-1H-1,2,4-triazole-3-carboximidamide as a white solid (>99% yield).

Step 6:

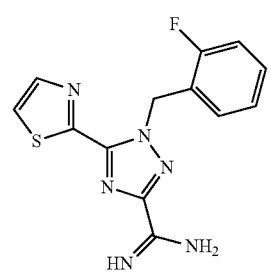

Intermediate-6

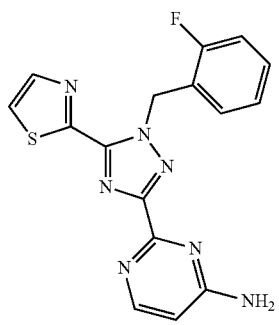

I-48

To 1-(2-fluorobenzyl)-5-(thiazol-2-yl)-1H-1,2,4-triazole-3-carboximidamide (Intermediate-6, 0.33 mmol) was added a stock solution of 3-ethoxyacrylonitrile (3 equiv) and DBU (1 equiv) in pyridine (3 mL). The reaction was warmed to 110° C. and stirred for 46 h. The reaction mixture was conc. and purified using SiO₂ chromatography and an appropriate gradient (CH₃CN/MeOH/CH₂Cl₂) to afford 2-(1-(2-fluorobenzyl)-5-(thiazol-2-yl)-1H-1,2,4-triazol-3-yl)pyrimidin-4-amine (I-48) as a light tan solid (78% yield).

I-48: ¹H NMR (400 MHz, DMSO-d₆) δ 8.15 (d, 1H), 8.13 (d, 1H), 8.08 (d, 1H), 7.38 (m, 1H), 7.27-7.14 (m, 3H), 7.13 (br. s, 2H), 6.44 (d, 1H), 6.16 (s, 2H) ppm. MS: [M+H]=354.

Compound I-57 and Intermediate-7

Step 1:

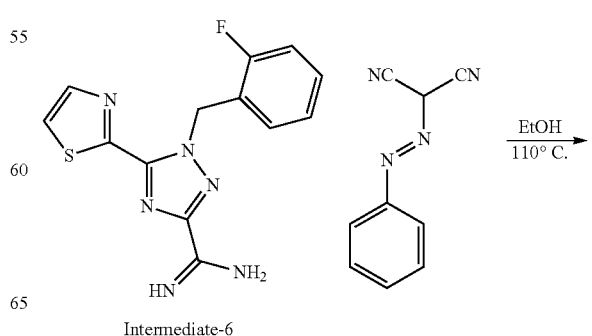

-continued

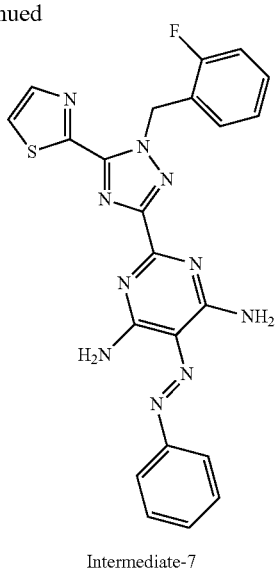

Intermediate-7

A suspension of 1-(2-fluorobenzyl)-5-(thiazol-2-yl)-1H-1,2,4-triazole-3-carboximidamide (Intermediate-6, 0.38 mmol) and 2-(phenyldiazenyl)malononitrile (1 equiv) in ethanol (6 mL) in a sealed tube was heated at 110° C. for 2 h. The reaction was conc. to afford 2-(1-(2-fluorobenzyl)-5-(thiazol-2-yl)-1H-1,2,4-triazol-3-yl)-5-(phenyldiazenyl)pyrimidine-4,6-diamine as an orange solid (>99% yield).
Step 2:

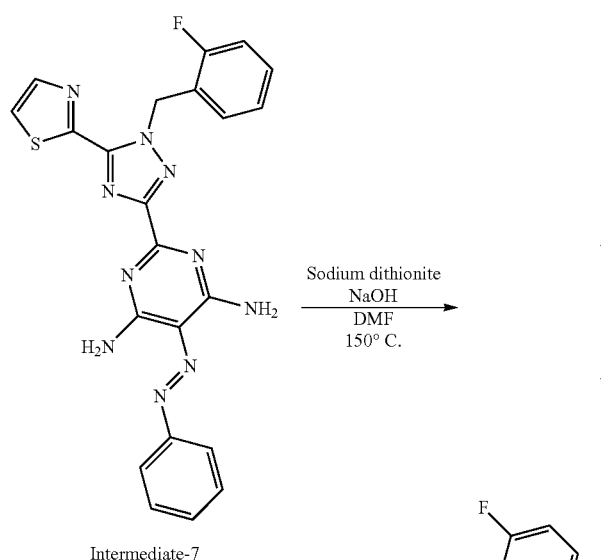

Intermediate-7

To a solution of 2-(1-(2-fluorobenzyl)-5-(thiazol-2-yl)-1H-1,2,4-triazol-3-yl)-5-(phenyldiazenyl)pyrimidine-4,6-diamine (Intermediate-7, 0.38 mmol) in DMF (2.5 mL) was added sodium hydroxide solution (2N, 3 equiv) and sodium dithionite (5.5 equiv). The reaction was heated to 150° C. and stirred for 2 h. The reaction mixture was diluted with $CH_2Cl_2$ and filtered. The filtrate was conc. and purified using $SiO_2$ chromatography and an appropriate gradient ($CH_3CN$/MeOH/$CH_2Cl_2$) to afford 2-(1-(2-fluorobenzyl)-5-(thiazol-2-yl)-1H-1,2,4-triazol-3-yl)pyrimidin-4,5,6-triamine as a tan solid (89% yield).

I-57: $^1$H NMR (400 MHz, DMSO-$d_6$) δ 8.10 (d, 1H), 8.04 (d, 1H), 7.36 (m, 1H), 7.23 (m, 1H), 7.16 (m, 2H), 6.11 (s, 2H), 5.83 (br. s, 4H), 4.10 (br. s, 2H) ppm. MS: [M+H]=384.

Compound I-60

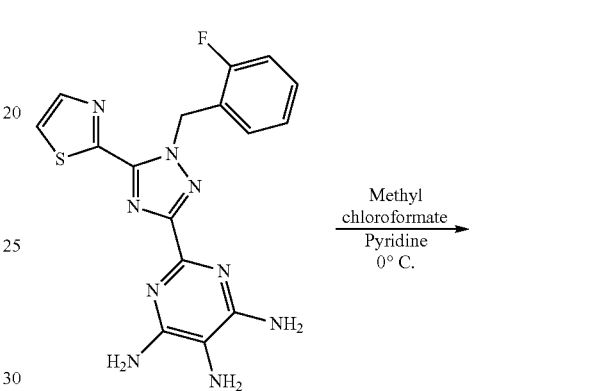

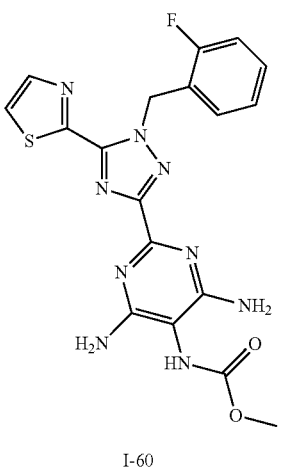

To a suspension of 2-(1-(2-fluorobenzyl)-5-(thiazol-2-yl)-1H-1,2,4-triazol-3-yl)pyrimidin-4,5,6-triamine (I-57, 0.31 mmol) in pyridine (2.0 mL) at 0° C. was treated with methyl chloroformate (1 equiv). After 30 min, additional portions of methyl chloroformate (3 equiv) were added and the reaction was stirred for 3 h. The reaction mixture was poured into water and the resultant tan solid was collected by filtration to afford methyl 4,6-diamino-2-(1-(2-fluorobenzyl)-5-(thiazol-2-yl)-1H-1,2,4-triazol-3-yl)pyrimidin-5-ylcarbamate (74% yield).

I-60: $^1$H NMR (400 MHz, DMSO-$d_6$) δ 8.11 (d, 1H), 8.06 (d, 1H), 7.98 (br. s, 1H), 7.37 (m, 1H), 7.23 (m, 1H), 7.16 (m, 2H), 6.22 (br. s, 4H), 6.14 (s, 2H), 3.60 (s, 3H) ppm. MS: [M+H]=442.

Compound I-61

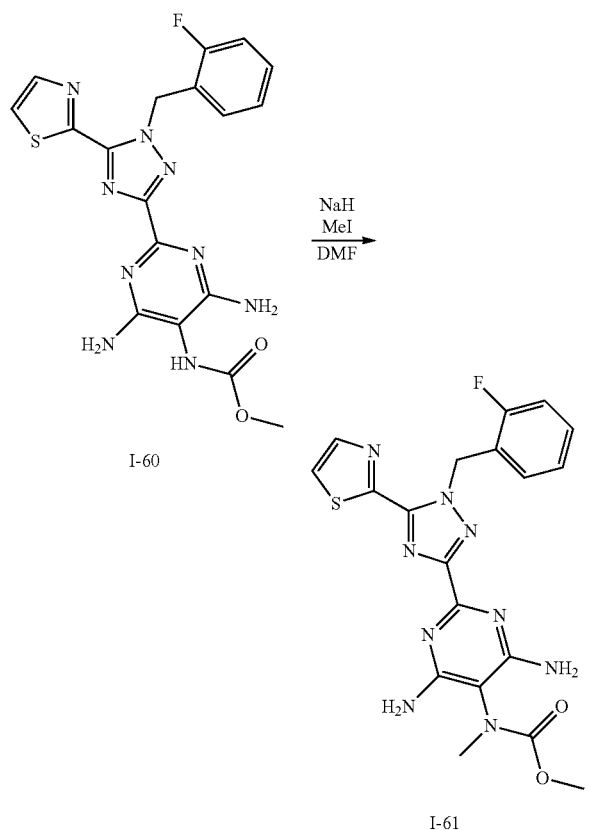

A suspension of methyl 4,6-diamino-2-(1-(2-fluorobenzyl)-5-(thiazol-2-yl)-1H-1,2,4-triazol-3-yl)pyrimidin-5-yl-carbamate (I-60, 0.16 mmol) in DMF (3.0 mL) at 0° C. was treated with sodium hydride (1.1 equiv). After 15 min, the reaction mixture was warmed to ambient temperature and stirred for 15 min. The reaction was cooled to 0° C. and iodomethane (1.1 equiv) was added. The resultant mixture was brought to ambient temperature and stirred for 20 min. Water was added and the aqueous mixture was extracted with EtOAc and iPrOH/CH$_2$Cl$_2$ (1:4). The organic phases were dried over Na$_2$SO$_4$, filtered, conc. and purified using SiO$_2$ chromatography and an appropriate gradient (CH$_3$CN/MeOH/CH$_2$Cl$_2$) to afford methyl 4,6-diamino-2-(1-(2-fluorobenzyl)-5-(thiazol-2-yl)-1H-1,2,4-triazol-3-yl)pyrimidin-5-yl(methyl)carbamate as an off-white solid (81% yield).

I-61: $^1$H NMR (400 MHz, DMSO-d$_6$) δ 8.11 (d, 1H), 8.05 (d, 1H), 7.37 (m, 1H), 7.23 (m, 1H), 7.15 (m, 2H), 6.43 (br. s, 4H), 6.14 (s, 2H), 3.64 (s, 0.3 of 3H, rotamer), 3.52 (s, 0.7 of 3H, rotamer), 2.97 (s, 3H) ppm. MS: [M+H]=456.

Compound I-35

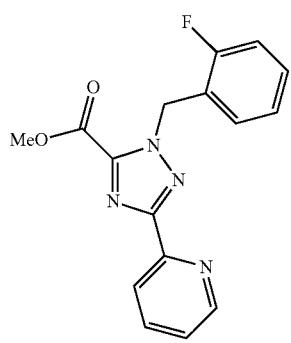

To a solution of 1-(2-fluorobenzyl)-3-(pyridin-2-yl)-1H-1,2,4-triazole-5-carbonitrile (I-33, 120 mg, 0.430 mmol) in methanol (2.0 mL) was added cesium carbonate (280 mg, 0.859 mmol). After stirring at room temperature for 3.75 h, aqueous 0.1 N hydrochloric acid (10 mL) was added, followed by aqueous 1 N hydrochloric acid (~1 mL) until pH ~3. After stirring for 45 min, the methanol was removed in vacuo, and the crude residue was brought up in ethyl acetate (75 mL) and saturated aqueous sodium bicarbonate (50 mL). The layers were separated, and the aqueous layer was extracted with ethyl acetate (2×50 mL). The organics were washed with brine (50 mL), dried over magnesium sulfate, filtered, and the solvent was removed in vacuo to give the crude product as white solid. Purification by silica gel chromatography (20-80% ethyl acetate in hexanes) gave methyl 1-(2-fluorobenzyl)-3-(pyridin-2-yl)-1H-1,2,4-triazole-5-carboxylate (99% yield) as a white solid.

$^1$H NMR (400 MHz, CDCl$_3$) δ 8.76-8.74 (m, 1H), 8.22 (d, 1H), 7.80 (dt, 1H), 7.36-7.33 (m, 1H), 7.31-7.25 (m, 1H), 7.16-7.05 (m, 3H), 6.00 (s, 2H), 4.02 (s, 3H).

Compound I-42

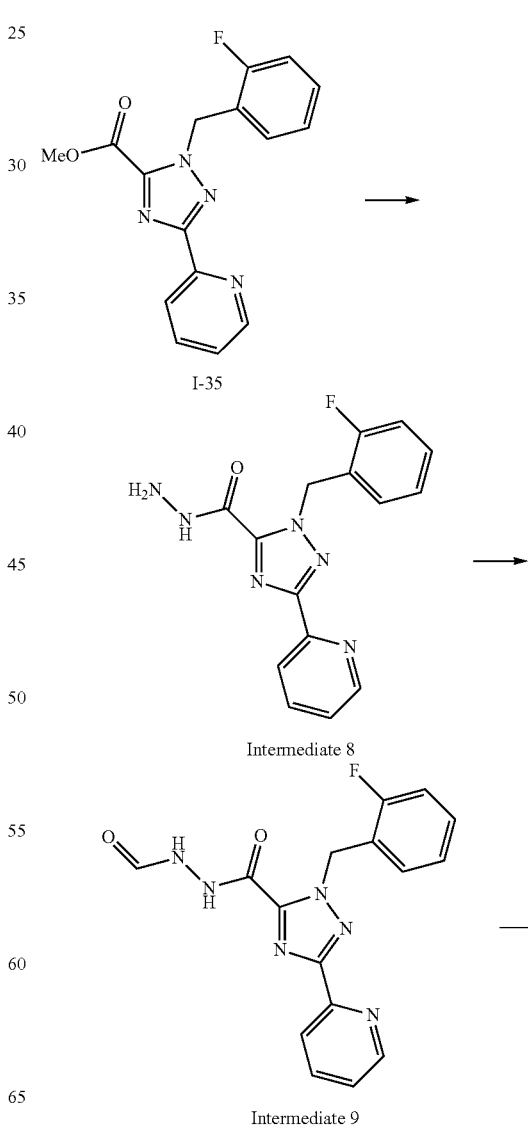

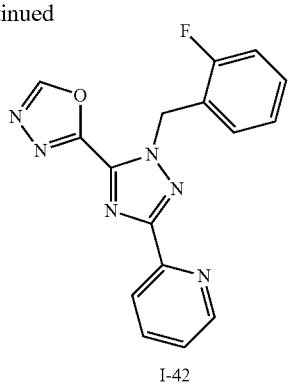

I-42

To a solution of methyl 1-(2-fluorobenzyl)-3-(pyridin-2-yl)-1H-1,2,4-triazole-5-carboxylate I-35 (115 mg, 0.368 mmol) in methanol (2 mL) was added hydrazine hydrate (72 µL, 1.5 mmol). The solution was heated to 70° C. for 3.5 h, at which point the solvent was removed in vacuo to give 1-(2-fluorobenzyl)-3-(pyridin-2-yl)-1H-1,2,4-triazole-5-carbohydrazide C as a white solid. To the crude solid (17 mg, 0.054 mmol) suspended in ethyl acetate (600 µL) was added acetic formic anhydride (0.03 mL, taken from a 2:1 (molar ratio) of formic acid to acetic anhydride, allowed to age 2 h prior to addition). After stirring for 1.25 h, the solution was diluted with ethyl acetate (50 mL) and water (50 mL). The layers were separated and the aqueous layer was extracted with ethyl acetate (2×50 mL). The organics were dried over MgSO4, filtered, and the solvent was removed in vacuo to give the crude intermediate D that was carried on without further purification. To the crude solid was added phosphoryl chloride (237 µl, 2.54 mmol) and the solution was heated to 60° C. for 6.5 h. The solution was diluted with ethyl acetate (75 mL) and saturated aqueous sodium bicarbonate (75 mL). The layers were separated, and the aqueous layer was extracted with ethyl acetate (2×50 mL). The organics were washed with brine (50 mL), dried over magnesium sulfate, filtered, and the solvent was removed in vacuo. Purification by silica gel chromatography (20-95% ethyl acetate in hexanes) gave 2-(1-(2-fluorobenzyl)-3-(pyridin-2-yl)-1H-1,2,4-triazol-5-yl)-1,3,4-oxadiazole I-42 (7.5 mg, 0.023 mmol, 42% yield for three steps) as a white solid.

I-42: $^1$H NMR (400 MHz, CDCl$_3$) δ 8.78-8.76 (m, 1H), 8.64 (s, 1H), 8.21 (d, 1H), 7.82 (dt, 1H), 7.38-7.35 (m, 1H), 7.32-7.21 (m, 2H), 7.09-7.04 (m, 2H), 6.17 (s, 2H).

Example 10

Biological Activity Measurement by the sGC-HEK-cGMP Assay

Human embryonic kidney cells (HEK293), endogenously expressing soluble guanylate cyclase (sGC), were used to evaluate the activity of the test compounds. Compounds stimulating the sGC receptor should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 µL volume at a density of 1×10$^5$ cells/well in a poly-D-lysine coated 96 well flat bottom plate and grown overnight at 37° C. Medium was aspirated and cells were washed with 1× Hank's Buffered Saline Salt Solution (200 µL). Cells were then incubated for 15 minutes at 37° C. with 0.5 mM 3-isobutyl-1-methylxanthine (200 µL).

Test article was then added to the assay mixture (2 µL) and incubated in the presence of 10 µM Sodium Nitroprusside (SNP) at 37° C. for 10 minutes. After the 10 minute incubation, the assay mixture was aspirated and 0.1M HCl (200 µL) was added to the cells. The plate was incubated at 4° C. for 30 minutes in the 0.1M HCl to stop the reaction and lysed the cells. The plates were then centrifuged at 1,200 g for 5 minutes at room temperature. Supernatants were collected and transferred to a new flat bottom 96 well plate for analysis. Vehicle controls were carried out using DMSO (1%). A known sGC stimulator, BAY 41-2272, was used as the positive control.

Samples were diluted with an equal volume of 1 M Ammonium Acetate (pH 7) to neutralize samples for better chromatography. A 2×cGMP standard curve was prepared in 0.1 M HCl and then diluted with an equal volume of 1 M Ammonium Acetate, with the following final concentrations in nM: 1024, 512, 256, 128, 64, 32, 16, 8, 4, 2, 1. cGMP concentrations were determined from each sample using the LC/MS conditions (Table 2 below) and calculated standard curve. EC50 values were calculated from concentration-response curves generated with GraphPad Prism Software.

TABLE 2

(LC/MS experimental conditions)

| MS: | Thermo Quantum or Waters LCMS |
| --- | --- |
| Ion Mode: | ESI$^+$ |
| Scan Type: | MRM |

| Compound: | Transition | Dwell Time (msec) | Collision Energy (V) | Tube Lens | Retention Time (min) |
| --- | --- | --- | --- | --- | --- |
| cGMP | 346 > 152 | 100 | 28 | 139 | 1.0 |

| HPLC: | Agilent Technologies 1200 Series with CTC Analytics HTS PAL |
| --- | --- |
| Column: | Thermo Hypersil Gold 2.1 × 50 mm 5 micron particle size |
| Flow Rate: | 400 uL/min |
| Column Temperature: | RT |
| Autosampler Temperature: | 6° C. |
| Injection Volume: | 20 uL |
| Mobile Phases: | A = 98:2 Water: Acetonitrile + 0.1% Formic Acid<br>B = 2:98 Water:Acetonitrile + 0.1% Formic Acid |

| Gradient: Time (min) | % A | % B |
| --- | --- | --- |
| 0 | 100 | 0 |
| 0.3 | 30 | 70 |
| 2.00 | 30 | 70 |
| 2.01 | 100 | 0 |
| 4 | 100 | 0 |

The biological activities of some of the compounds according to Formula IA or Formula IB determined with the sGC-HEK assay are summarized in Table 3 below.

TABLE 3

| Test Compound | HEK Assay (% E$_{max}$) at 10 µm)* | HEK Assay (% E$_{max}$) at 30 µm)* |
| --- | --- | --- |
| I-1 | B | D |
| I-2 | B | B |
| I-3 | A | D |
| I-4 | D | E |
| I-5 | B | C |
| I-6 | D | D |
| I-7 | A | B |

TABLE 3-continued

| Test Compound | HEK Assay (% $E_{max}$ at 10 μm)* | HEK Assay (% $E_{max}$ at 30 μm)* |
|---|---|---|
| I-8 | A | A |
| I-9 | A | B |
| I-11 | C | C |
| I-12 | D | E |
| I-13 | A | A |
| I-14 | B | C |
| I-16 | A | B |
| I-18 | A | A |
| I-19 | C | A |
| I-20 | A | A |
| I-21 | A | A |
| I-24 | B | C |
| I-25 | D | E |
| I-26 | C | C |
| I-27 | A | A |
| I-28 | A | A |
| I-29 | A | A |
| I-30 | C | D |
| I-31 | A | A |
| I-32 | A | C |
| I-35 | A | A |
| I-36 | A | A |
| I-37 | C | D |
| I-38 | E | D |
| I-39 | B | B |
| I-40 | D | C |
| I-41 | E | F |
| I-42 | A | B |
| I-43 | A | A |
| I-44 | E | F |
| I-45 | A | A |
| I-46 | D | D |
| I-47 | A | A |
| I-48 | E | F |
| I-49 | A | B |
| I-50 | D | D |
| I-51 | D | D |
| I-52 | A | A |
| I-53 | E | F |
| I-54 | D | E |
| I-55 | A | B |
| I-56 | C | E |
| I-57 | A | A |
| I-58 | E | F |
| I-59 | A | A |
| I-60 | C | D |
| I-61 | D | E |
| I-62 | C | B |
| I-63 | F | D |
| I-64 | C | B |
| I-65 | G | G |
| I-66 | E | E |
| I-67 | C | C |
| I-68 | D | E |

*The compounds were tested at a concentration of 10 or 30 μM. The code for the sGC activity expressed as % $E_{max}$ (i.e., percentage of the sGC activity obtained with the positive control, BAY 41-2272, of Bayer; wherein $E_{max}$ = 100% was the sGC activity in the HEK assay obtained with the positive control) obtained is:
A = 0 to <5%
B = 5 to <10%
C = 10 to <20%
D = 20 to <40%
E = 40 to <60%

Example 11

Biological Activity Measurements by the Purified Human sGC Enzyme Activity Assay Human soluble guanylate cyclase enzyme (hsGC) obtained from Enzo Inc. (P/N: ALX-201-177) was used to evaluate the activity of test compounds. The assay reactions contained 0.1 M Tris (pH 8.0), 0.5 mg/mL BSA (pH 8.0), 2 mM DTT, 2 mM $MgCl_2$, 300 μM GTP, 1 mM 3-isobutyl-1-methylxanthine (IBMX) and 5 ng human soluble guanylate cyclase enzyme. Test compounds in DMSO were then added (2 μL, 10 or 30 μM final concentration) and incubated (200 μL, 96-well plate format) at 37° C. for 30 minutes. The controls were carried out using 2 μL DMSO. After the 30 minute incubation, the reaction was stopped with the addition of 200 μL of cold methanol. The plate was then centrifuged at 3,200 rpm for 10 minutes at room temperature. Supernatants (200 μL) were collected and transferred to a new 96 well plate for analysis.

An 8 point cGMP (Sigma-Aldrich P/N: G6129) standard curve was prepared in assay buffer ranging from 0.156-20 μM. Samples for the cGMP standard curve were then diluted with an equal volume of methanol resulting in final cGMP concentrations of 0.078-10 μM.

cGMP concentrations in all samples were determined using LC/MS/MS analysis, using the conditions listed in Table 4 below. The cGMP standard curve was generated using GraphPad Prism Software.

Calculations: Specific Activity was determined by the amount of cGMP formed (nmoles) per mg of sGC per min. Enzyme activity "fold-change" was calculated by dividing the Specific Activity for a test compound by the Specific Activity of DMSO control.

TABLE 4

LC/MS/MS method for detection of cGMP

Inlet Method:

| | |
|---|---|
| HPLC: | Waters Acquity |
| Column: | Thermo Hypersile Gold PFP, 2.1 × 30 mm, 3 μm |
| Guard Column: | Thermo Hypersile Gold, 2.1 × 10 mm |
| Column Temp: | 25° C. |
| Flow Rate: | 0.4 mL/min |
| Auto sampler: | Acquity; 6° C. |
| Injection Volume: | 10 uL |
| Mobile Phases: | A = 0.1% Acetic Acid (v/v) in 100% water |
| | B = 0.1% Acetic Acid (v/v) in 100 methanol |

| Gradient: | Time (min) | % A | % B | Curve |
|---|---|---|---|---|
| | 0 | 95 | 5 | 6 |
| | 0.5 | 95 | 5 | 6 |
| | 0.6 | 10 | 90 | 6 |
| | 2.0 | 10 | 90 | 6 |
| | 2.1 | 95 | 5 | 6 |
| | 4 | (end) | | |

MS File: cGMP.exp

| | |
|---|---|
| Mass Spectrum: | Waters Quattro micro |
| Ionization: | ES+ |
| Source, Desolvation: | 150° C., 450° C. |
| MS Function: | MRM |

| Compound | Transition | Dwell (sec) | Cone (V) | Collision Energy (eV) |
|---|---|---|---|---|
| cGMP | 346 > 152 | 0.1 | 35 | 20 |

The enzymatic activity fold-change of the purified human sGC enzyme determined in the presence of each of the test compounds individually at 10 or 30 μm without the addition of sodium nitroprusside (SNP), a nitric oxide donor, is presented in Table 5.

Enzyme assays were also performed as described above, but in the presence of 1 μM sodium nitroprusside (SNP). The results of the enzyme activity assay performed in the presence of SNP are also presented in Table 5. Enzymatic activity fold-changes are reported for selected test compounds in the presence of both SNP and the test compound. These were calculated by dividing the specific activity (activity increase)

for the test compound dissolved in DMSO and SNP over the specific activity for the mixture of DMSO and SNP.

TABLE 5

(Enzyme Data With or without SNP)

| Compound | sGC Enzyme Activity Increase at 10 μM without SNP* | sGC Enzyme Activity Increase at 30 μM without SNP* | sGC Enzyme Activity Increase at 10 μM with SNP* | sGC Enzyme Activity Increase at 30 μM with SNP* |
|---|---|---|---|---|
| I-1 | B | C | B | C |
| I-2 | N | D | N | C |
| I-3 | N | B | N | D |
| I-4 | N | C | N | E |
| I-5 | N | B | N | C |
| I-6 | N | D | N | D |
| I-7 | N | B | N | B |
| I-8 | N | C | N | B |
| I-9 | N | C | N | B |
| I-11 | N | C | N | C |
| I-12 | N | C | N | E |
| I-13 | N | C | N | B |
| I-14 | N | B | N | C |
| I-16 | N | B | N | C |
| I-18 | N | B | N | C |
| I-19 | N | B | N | C |
| I-20 | N | B | N | B |
| I-21 | N | B | N | B |
| I-24 | N | C | N | C |
| I-25 | N | D | N | E |
| I-26 | N | C | N | D |
| I-27 | N | B | N | B |
| I-28 | N | B | N | B |
| I-29 | N | B | N | C |
| I-30 | N | B | N | C |
| I-31 | N | B | N | C |
| I-32 | N | C | N | C |
| I-35 | N | B | N | C |
| I-36 | N | B | N | B |
| I-37 | N | C | N | D |
| I-38 | N | C | N | E |
| I-39 | N | B | N | C |
| I-40 | N | B | N | D |
| I-41 | N | C | N | E |
| I-42 | N | B | N | C |
| I-43 | N | B | N | B |
| I-44 | N | D | N | F |
| I-45 | N | B | N | B |
| I-46 | N | B | N | C |
| I-47 | N | B | N | B |
| I-48 | N | C | N | D |
| I-49 | N | B | N | B |
| I-50 | N | B | N | C |
| I-51 | N | C | N | E |
| I-52 | N | B | N | B |
| I-53 | N | D | N | F |
| I-54 | N | C | N | D |
| I-55 | N | B | N | C |
| I-56 | N | B | N | D |
| I-57 | N | B | N | C |
| I-58 | N | C | N | D |
| I-59 | N | A | N | A |
| I-60 | N | B | N | D |
| I-61 | N | C | N | D |
| I-62 | N | A | N | C |
| I-63 | N | B | N | D |
| I-65 | N | D | N | E |
| I-68 | N | C | N | E |

*Code for the increase in the activity of the sGC enzyme in the presence of the test compound with or without SNP:
A = no increase to <1 fold increase
B = 1 to <2 fold increase
C = 2 to <5 fold increase
D = 5 to <10 fold increase
E = 10 to <20 fold increase
F = 20 to <50 fold increase
N = not determined Example 12

Biological Activity Measurement by the Thoracic Aortic Rings Assay

Thoracic aortic rings were dissected from anesthetized (isoflurane) male Sprague-Dawley rats weighing 275-299 g. Tissues were immediately transferred to ice-cold Krebs-Henseleit solution, which had been aerated with 95% $O_2$ and 5% $CO_2$ for 30 minutes. Following removal of connective tissue, aortic sections were cut into 4 rings (~2 mm each) and suspended on 2 L-shaped hooks, with one hook fixed at the bottom of the tissue bath (Schuler Organ Bath, Harvard Apparatus) and the other connected to a force transducer (F30 Force Transducer, Harvard Apparatus). Baths contained Krebs Henseleit solution (10 mL) heated to 37° C. and aerated with 95% $O_2$ and 5% $CO_2$. Rings were brought to an initial tension of 0.3-0.5 g and gradually raised to a resting tension of 1.0 g over 60 minutes. Rings were rinsed with Krebs Henseleit solution (heated to 37° C. and aerated with 95% 02 and 5% $CO_2$) at 15 minute intervals until a stable baseline was obtained. Rings were considered to be stable after a resting tension of 1.0 g was maintained (for approximately 10 minutes) without need for adjustment. Rings were then contracted with 100 ng/mL phenylephrine by adding 100 μL of a 10 μg/mL phenylephrine stock solution. Tissues achieving a stable contraction were then treated in a cumulative, dose dependent manner with test compounds prepared in dimethylsulfoxide (DMSO). In some cases, tissues were rinsed three times over a 5 minute period with Krebs-Heinseleit's solution (heated to 37° C. and aerated with 95% 02 and 5% $CO_2$), allowed to stabilize at baseline, and then used for characterization of other test articles or DMSO effects. All data were collected using the HSE-ACAD software provided by Harvard Apparatus. Percent relaxation effects were calculated in Microsoft Excel using the recorded tension value of 100 ng/mL phenylephrine treatment as 0% inhibition and, after washing the tissue with buffer, the original resting tension of tissue is used as 100% inhibition. $EC_{50}$ values were calculated from concentration-response curves generated with GraphPad Prism Software.

The biological data for some of the compounds of Formula IA and Formula IB, in comparison with the prior art compound, BAY 41-2272, as the reference compound, determined by the thoracic aorta ring assay are presented in Table 6 below.

TABLE 6

Thoracic Ring Assay Results*

| Compound Tested | Percent Relaxation at 1 μM* | Percent Relaxation at 3 μM* | Percent Relaxation at 10 μM* | Aortic Ring $EC_{50}$ (μM)** |
|---|---|---|---|---|
| BAY-41-2272 | N | N | N | A |
| I-1 | C | E | G | B |
| I-3 | D | F | G | B |
| I-4 | E | G | N | A |
| I-6 | C | E | G | B |
| I-12 | D | F | G | A |
| I-25 | D | F | G | A |
| I-30 | C | E | G | C |
| I-38 | D | F | G | B |
| I-40 | C | E | G | B |
| I-41 | F | G | G | A |
| I-44 | F | G | G | A |
| I-46 | C | E | F | C |
| I-48 | D | F | G | B |

TABLE 6-continued

Thoracic Ring Assay Results*

| Compound Tested | Percent Relaxation at 1 µM* | Percent Relaxation at 3 µM* | Percent Relaxation at 10 µM* | Aortic Ring $EC_{50}$ (µM)** |
|---|---|---|---|---|
| I-50 | B | C | E | N |
| I-53 | C | F | G | B |
| I-61 | E | F | N | A |

*Each of the compound was tested at a concentration of 1, 3 or 10 µM to obtain data using the method described in Example 11. The code for the percent relaxation of the aotic ring is:
A = 0 to <10%
B = 10 to <20%
C = 20 to <40%
D = 40 to <60%
E = 60 to <80%
F = 80 to <100%
G = 100 to <120%
N = not determined
**The code for the $EC_{50}$ value obtained is:
A = 0 to <1 µM
B = 1 to <2 µM
C = 2 to <3 µM
N = not determined A number of embodiments have been described. Nevertheless, it will be understood that various modifications may be made without departing from the spirit and scope of the invention.

The invention claimed is:

1. A compound according to Formula IA or IB, or a pharmaceutically acceptable salt thereof, Formula IA Formula IB wherein:
the symbol with the encircled letter B represents ring B, and ring B is a phenyl or a 6-membered heteroaryl ring, having 1 or 2 nitrogen ring atoms;
n is an integer selected from 0 to 3;
each $J^B$ is independently selected from halogen, —CN, —$NO_2$, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^3$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
wherein ring D is the 5-membered ring heteroaryl of Formula IB or the 6-membered heteroaryl ring of Formula IA that is substituted by m instances of $J^D$;
X is selected from N or C;
each Y is independently selected from C, N, O or S; wherein a minimum of 0 and maximum of 3 instances of Y can be N, O or S simultaneously and the remaining instance or instances of Y are C;
m is an integer selected from 0 to 3;
each $J^D$ that is a substituent on a carbon ring atom of Formula IA or Formula IB is independently selected from halogen, —$NO_2$, —$OR^D$, —$SR^D$, —$C(O)R^D$, —$C(O)OR^D$, —$C(O)N(R^D)_2$, —CN, —$N(R^D)_2$, $N(R^d)C(O)R^D$, $N(R^d)C(O)OR^D$, —$SO_2R^D$, —$SO_2N(R^D)_2$, —$N(R^d)SO_2R^D$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;
each $J^D$ that is a substituent on a nitrogen ring atom of Formula IB is independently selected from —$C(O)R^D$, —$C(O)OR^D$, —$C(O)N(R^D)_2$, —$SO_2R^D$, —$SO_2N(R^D)_2$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring has between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;
each $R^D$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring has between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^5$;
each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring has between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;
each $R^f$ is independently selected from a $C_{3-8}$ cycloaliphatic ring, a 4 to 8-membered heterocyclic ring, phenyl or a 5 to 6-membered heteroaryl ring;

wherein each said heterocylic ring and each said heteroaryl ring has between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;

alternatively, two instances of $R^D$ linked to the same nitrogen atom of $J^D$, together with said nitrogen atom of $J^D$, form a 4 to 8-membered heterocyclic ring or a 5-membered heteroaryl ring; wherein each said 4 to 8-membered heterocyclic ring and each said 5-membered heteroaryl ring optionally has up to 2 additional heteroatoms independently selected from N, O or S, and wherein each said 4 to 8-membered heterocyclic ring and each said 5-membered heteroaryl ring is optionally and independently substituted by up to 3 instances of $R^5$; or alternatively, one instance of $R^D$ linked to a carbon, oxygen or sulfur atom of $J^D$ and one instance of $R^d$ linked to a nitrogen atom of the same $J^D$, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally has up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —OR$^6$, —SR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each $R^6$ is independently selected from hydrogen, a $C_{1-4}$ alkyl, phenyl, a $C_{7-12}$ aralkyl or a $C_{3-8}$ cycloalkyl ring; wherein each of said $C_{1-4}$ alkyl, each said phenyl, each said $C_{7-12}$ aralkyl and each said cycloalkyl group is optionally and independently substituted with up to 3 instances of halogen;

alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally has up to 2 additional heteroatoms independently selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally has up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle has from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ alkyl)$_2$, —CN, C$_{1-4}$ alkyl, C$_{1-4}$ haloalkyl, —O(C$_{1-4}$ alkyl), —O(C$_{1-4}$ haloalkyl) or oxo;

$R^C$ is selected from halo, —CN, $C_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle has between 1 and 4 heteroatoms selected from N, O or S; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each $J^C$ is independently selected from halogen, —CN, —NO$_2$, a $C_{1-6}$ aliphatic, —OR$^H$, —SR$^H$, —N(R$^H$)$_2$, a $C_{3-8}$ cycloaliphatic ring or a 4 to 8-membered heterocyclic ring; wherein said 4 to 8-membered heterocyclic ring has 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle has from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring has between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally has up to 2 additional heteroatoms independently selected from N, O or S, and wherein each said 4 to 8-membered heterocyclic ring and each said 5-membered heteroaryl ring is optionally and independently substituted by up to 3 instances of $R^7$; or each $R^7$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^8$ is independently selected from hydrogen, a $C_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of $R^8$ linked to the same nitrogen atom of $R^7$, together with said nitrogen atom of $R^7$, form a 5 to 8-membered heterocyclic ring or a 5-membered heteroaryl ring; wherein each said 5 to 8-membered heterocyclic ring and each said 5-membered heteroaryl ring optionally has up to 2 additional heteroatoms independently selected from N, O or S; and provided that the compound is not one of the compounds represented below:

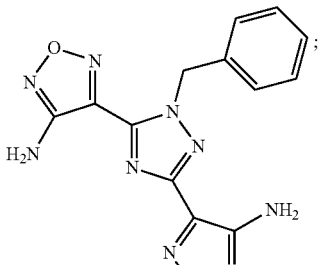

(CAS #799825-21-1)

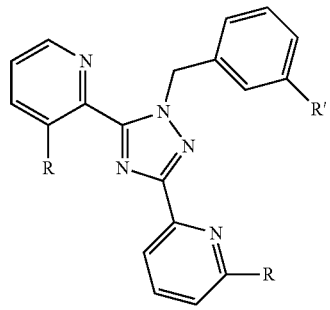

R' = H and
{
R = H (CAS #150223-76-0)
R = —CN (CAS #150223-78-2)
R = —COOMe (CAS #189263-49-8)
R = —CH₂OH (CAS #189263-50-1)
R = —CH₂NH₂ (CAS #150202-42-9)
R = —CH₂Br (CAS #189263-51-2)
}

R' = —NO₂ and
{
R = H (CAS #150223-82-8)
R = —CN (CAS #150223-84-0)
R = —CH₂NH₂ (CAS #150202-43-0)
}

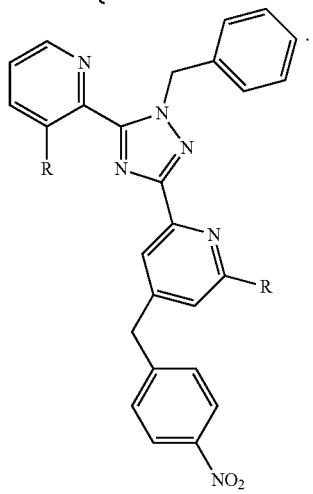

R = H (CAS #150223-91-9)
R = —CN (CAS #150223-95-3)
R = —CH2NH2 (CAS #150223-97-5)

2. The compound of claim 1, or a pharmaceutically acceptable salt thereof, wherein ring B is phenyl.

3. The compound of claim 1 or claim 2, or a pharmaceutically acceptable salt thereof, wherein n is an integer selected from 1 to 3 and wherein each $J^B$ is independently selected from halogen, a $C_{1-6}$ aliphatic or —$OR^B$.

4. The compound of claim 3, or a pharmaceutically acceptable salt thereof, wherein each $J^B$ is independently selected from halogen atoms.

5. The compound of claim 4, or a pharmaceutically acceptable salt thereof, wherein each $J^B$ is independently selected from fluoro or chloro.

6. The compound of claim 5, or a pharmaceutically acceptable salt thereof, wherein each $J^B$ is fluoro.

7. The compound of claim 3, or a pharmaceutically acceptable salt thereof, wherein n is 1.

8. The compound of claim 7, or a pharmaceutically acceptable salt thereof, wherein $J^B$ is selected from halogen atoms.

9. The compound of claim 8, or a pharmaceutically acceptable salt thereof, wherein $J^B$ is fluoro.

10. The compound of claim 3, or a pharmaceutically acceptable salt thereof, wherein at least one $J^B$ is ortho to the attachment of the methylene linker between ring B and the triazolyl ring.

11. The compound of claim 10, or a pharmaceutically acceptable salt thereof, wherein each $J^B$ is fluoro.

12. The compound of claim 1, or a pharmaceutically acceptable salt thereof, wherein X in ring D of Formula IA is N.

13. The compound of claim 1, or a pharmaceutically acceptable salt, wherein one of the 4 instances of Y in ring D of Formula IB is selected from N, O or S and the other 3 instances of Y in ring D are carbon atoms, wherein said carbon atoms are optionally substituted.

14. The compound of claim 12 or claim 13, or a pharmaceutically acceptable salt thereof, wherein m is an integer selected from 1, 2 or 3 and each $J^D$ is independently selected from halogen, a $C_{1-6}$ aliphatic, —$N(R^D)_2$, —$N(R^d)C(O)R^D$, —$N(R^d)C(O)OR^D$, —$SO_2R^D$, —$SO_2N(R^D)_2$, —$N(R)SO_2R^D$, —$SR^D$, —$OR^D$ or an optionally substituted $C_{3-8}$ cycloaliphatic ring.

15. The compound of claim 14, or a pharmaceutically acceptable salt thereof, wherein each $J^D$ is independently selected from —$N(R^D)_2$, —$N(R^d)C(O)R^D$, —$N(R^d)C(O)OR^D$, —$SO_2R^D$, —$SO_2N(R^D)_2$, —$N(R^d)SO_2R^D$ or —$OR^D$.

16. The compound of claim 15, or a pharmaceutically acceptable salt thereof, wherein each $R^d$ is independently selected from a $C_{1-4}$ alkyl or hydrogen and each $R^D$ is independently selected from hydrogen or $C_{1-4}$ alkyl.

17. The compound of claim 16, or a pharmaceutically acceptable salt thereof, wherein each $R^d$ and each $R^D$ is independently selected from hydrogen or methyl.

18. The compound of claim 14, wherein m is 1, 2 or 3 and each $J^D$ is independently selected from methyl, fluoro, —$N(R^D)_2$, —$N(R)C(O)R^D$, —$N(R^d)C(O)OR^D$, —$SO_2R^D$, —$SO_2N(R^D)_2$ or —$N(R^d)SO_2R^D$; wherein each $R^d$ and each $R^D$ is independently selected from hydrogen or methyl.

19. The compound of claim 1, or a pharmaceutically acceptable salt thereof, wherein $R^C$ is a ring C.

20. The compound of claim 19, or a pharmaceutically acceptable salt thereof, wherein ring C is a phenyl ring, a monocyclic 5 or 6-membered heteroaryl ring, a monocyclic 3 to 10-membered cycloaliphatic ring or a monocyclic 4 to 10-membered heterocycle; wherein each of the phenyl ring, monocyclic 5 or 6-membered heteroaryl ring, or monocyclic 4 to 10-membered heterocycle is optionally and independently substituted with up to 3 instances of $J^C$.

21. The compound of claim 20, or a pharmaceutically acceptable salt thereof, wherein ring C is a phenyl, a monocyclic 5 or 6-membered heteroaryl ring, a monocyclic 3 to 6-membered cycloaliphatic ring or a monocyclic 4 to 6-membered heterocycle; wherein each of said phenyl, monocyclic 5 or 6-membered heteroaryl ring, or monocyclic 4 to 6-membered heterocycle is optionally and independently substituted with up to 3 instances of $J^C$.

22. The compound of claim 21, or a pharmaceutically acceptable salt thereof, wherein ring C is a monocyclic 3 to 6-membered cycloaliphatic ring.

23. The compound of claim 21, or a pharmaceutically acceptable salt thereof, wherein ring C is phenyl, optionally and independently substituted by up to 3 instances of $J^C$.

24. The compound of claim 21, or a pharmaceutically acceptable salt thereof, wherein ring C is a 5 to 6-membered heteroaryl ring, optionally substituted by up to 3 instances of $J^C$.

25. The compound of claim 24, or a pharmaceutically acceptable salt thereof, wherein ring C is an unsubstituted 5 to 6-membered heteroaryl ring.

26. The compound of either of claim 24 or 25, or a pharmaceutically acceptable salt thereof, wherein said 5 to 6-membered heteroaryl ring as ring C is selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl.

27. The compound of claim 26, or a pharmaceutically acceptable salt thereof, wherein said 5 to 6-membered heteroaryl ring as ring C is selected from furanyl, thienyl, thiazolyl, oxazolyl, 1,3,4-oxadiazolyl, pyridinyl, pyrimidinyl or pyrazin-3-yl.

28. The compound of claim 27, or a pharmaceutically acceptable salt thereof, wherein said 5 to 6-membered heteroaryl ring as ring C is selected from thienyl, thiazolyl, oxazolyl, 1,3,4-oxadiazolyl or pyridinyl.

29. The compound of claim 28, or a pharmaceutically acceptable salt thereof, wherein the 5 to 6-membered heteroaryl ring as ring C is selected from furan-2-yl, furan-3-yl, thien-3-yl, thien-2-yl, thiazol-2-yl, thiazol-4-yl, oxazol-2-yl, oxazol-4-yl, pyridin-2-yl, pyridin-3-yl, pyridin-4-yl, pyrimidin-2-yl or pyrimidin-4-yl; and is optionally and independently substituted with up to 2 instances of $J^C$.

30. The compound of claim 29, or a pharmaceutically acceptable salt thereof, wherein each $J^C$ is independently selected from halogen, $C_{1-6}$ aliphatic, —CN, —NH$_2$ or —O($C_{1-6}$ aliphatic).

31. The compound of claim 1 having Formula IA, or a pharmaceutically acceptable salt thereof.

32. The compound of claim 31, or a pharmaceutically acceptable salt thereof, having Formula IIA,

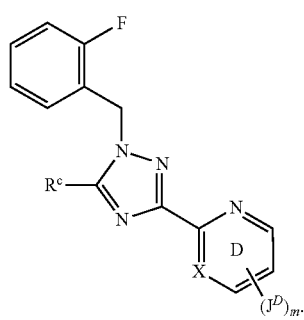

Formula IIA

33. The compound of claim 32, or a pharmaceutically acceptable salt thereof, having Formula III or Formula IV:

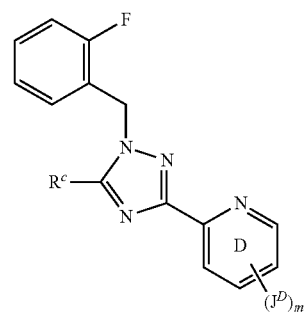

Formula III

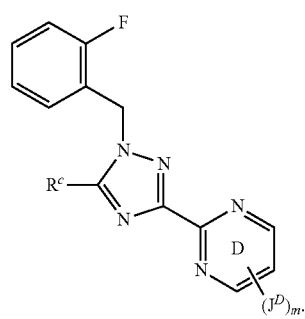

Formula IV

34. The compound of claim 33, or a pharmaceutically acceptable salt thereof, having one of Formulae VA, VC, VD and VF:

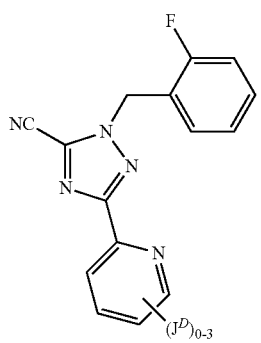

VA

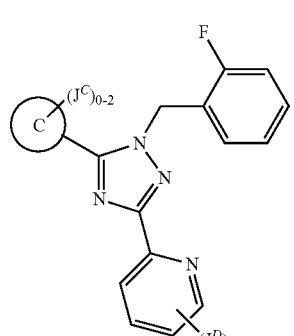

VC

-continued

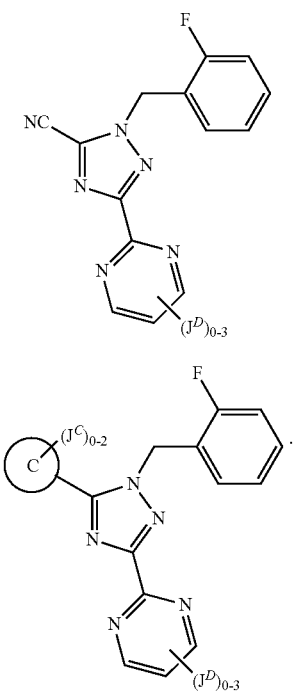

35. The compound of claim 1 having Formula IB, or a pharmaceutically acceptable salt thereof.

36. The compound of claim 35 having Formula IIB, or a pharmaceutically acceptable salt thereof:

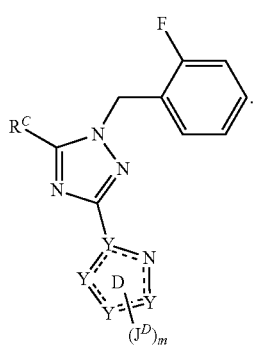

Formula IIB

37. The compound of claim 36 having Formula VII, or a pharmaceutically acceptable salt thereof,

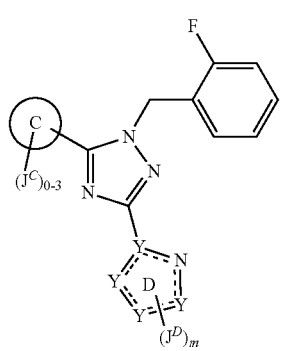

Formula VII wherein the symbol of the encircled letter C represents ring C.

38. The compound of claim 37, or a pharmaceutically acceptable salt thereof, wherein ring C is selected from a phenyl ring, a monocyclic 5 or 6-membered heteroaryl ring, a monocyclic 3 to 10-membered cycloaliphatic ring, or a monocyclic 4, 5 or 6-membered heterocycle; wherein each of said phenyl ring, monocyclic 5 or 6-membered heteroaryl ring or monocyclic 4, 5 or 6-membered heterocycle is optionally and independently substituted with up to 3 instances off.

39. The compound of claim 38, or a pharmaceutically acceptable salt thereof, wherein ring C is selected from a phenyl ring, cyclopropyl ring, cyclobutyl ring, azetidinyl ring, thiazolyl ring or oxazolyl ring.

40. The compound of claim 39, or a pharmaceutically acceptable salt thereof, wherein ring C is a thiazolyl ring or oxazolyl ring.

41. The compound of claim 40, or a pharmaceutically acceptable salt thereof, wherein ring C is selected from a thiazol-2-yl ring, thiazol-4-yl ring, oxazol-2-yl ring or oxazol-4-yl ring.

42. The compound of claim 41, or a pharmaceutically acceptable salt thereof, wherein ring C is a thiazol-2-yl ring or thiazol-4-yl ring.

43. The compound of any one of claim 1, 31-36 or 37-42, or a pharmaceutically acceptable salt thereof, selected from:

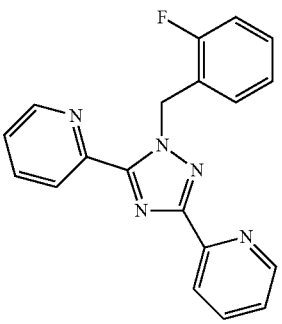

I-1

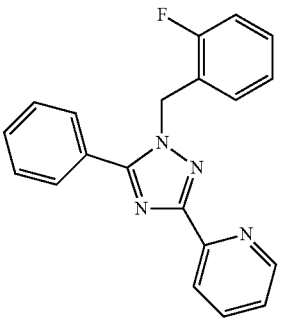

I-2

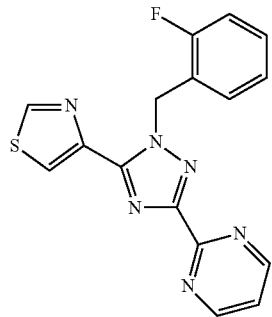

I-3

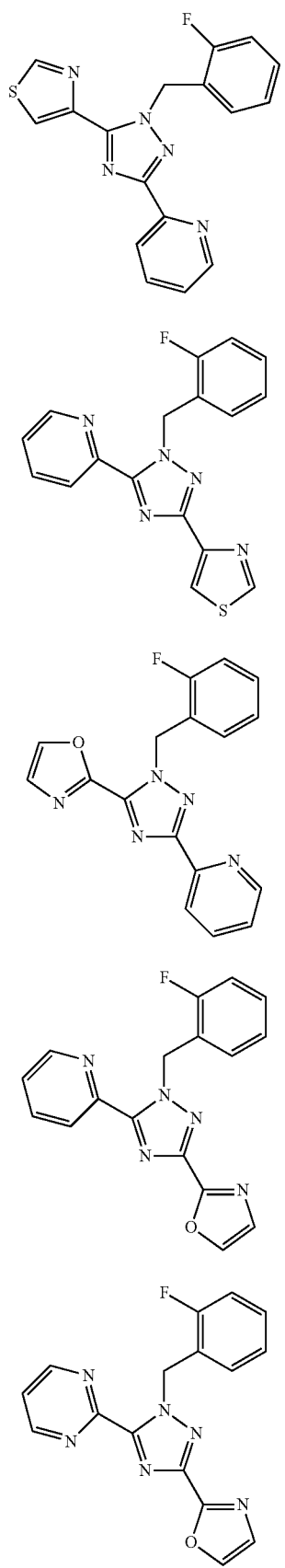
I-4
I-5
I-6
I-7
I-8
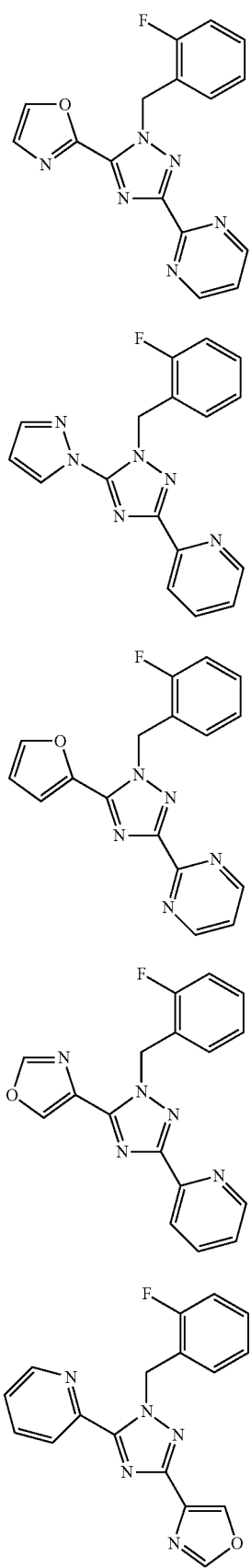
I-9
I-10
I-11
I-12
I-13

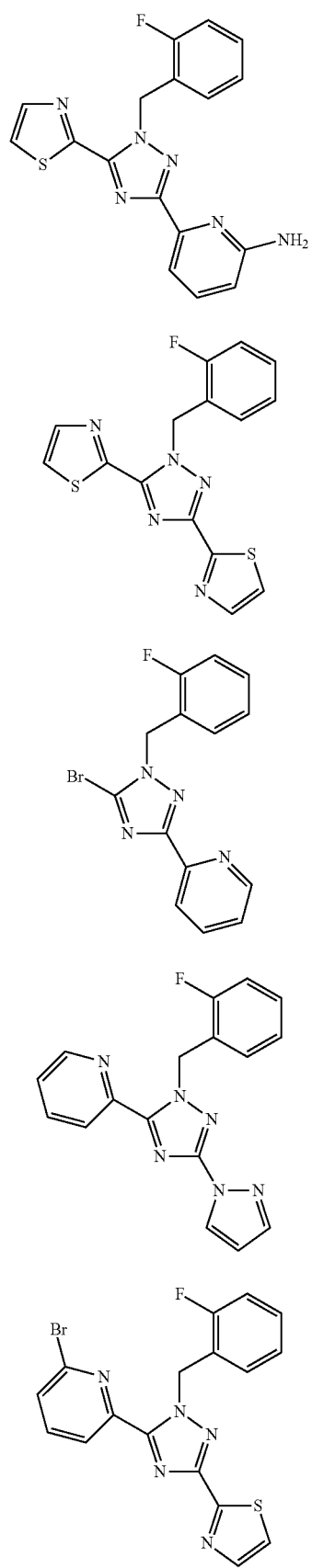
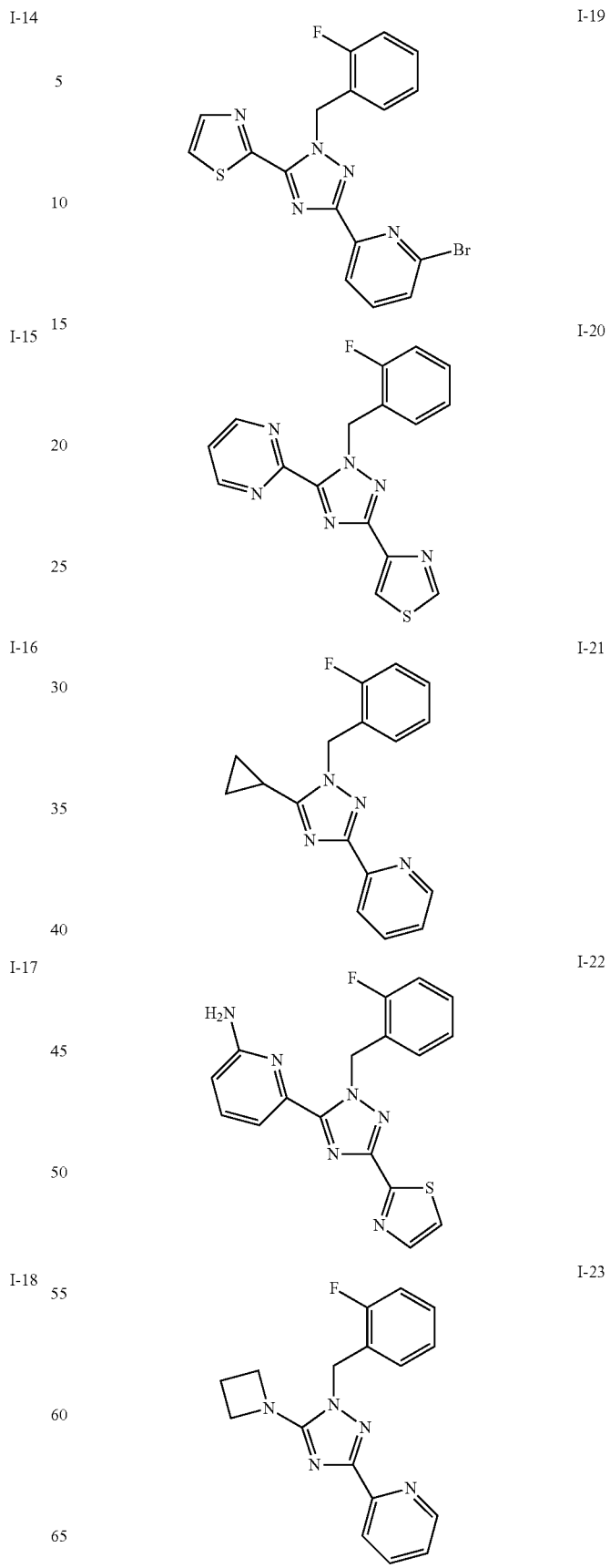

I-24
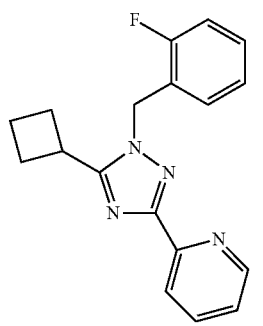
I-25
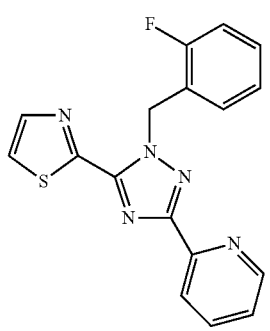
I-26
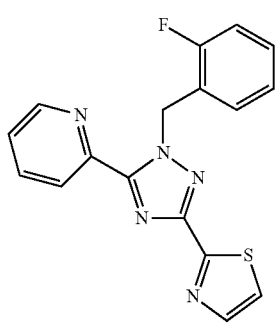
I-27
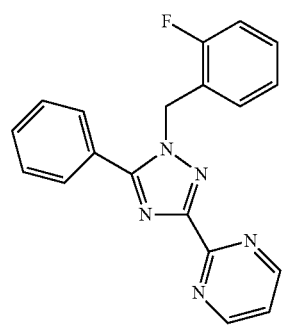
I-28
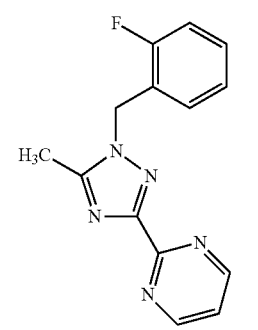
I-29
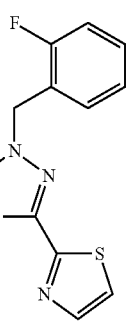
I-30
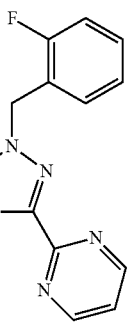
I-31
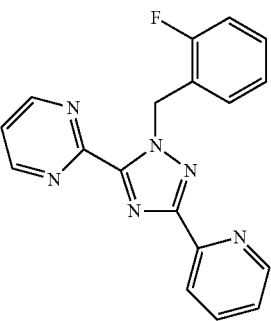
I-32
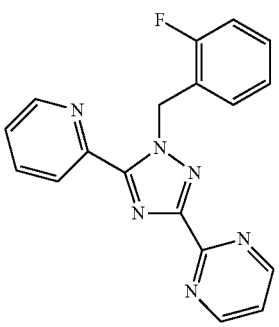
I-33
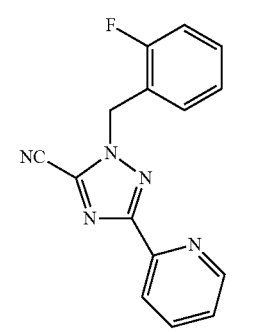

I-34 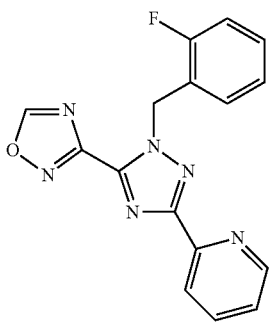
I-36 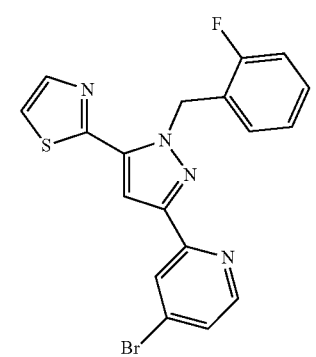
I-37 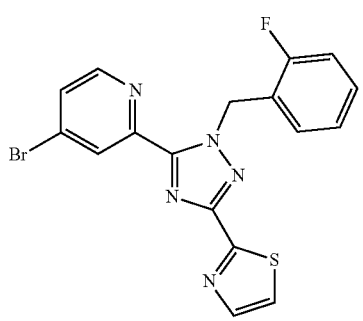
I-38 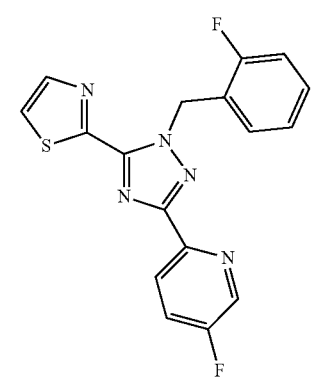
I-39 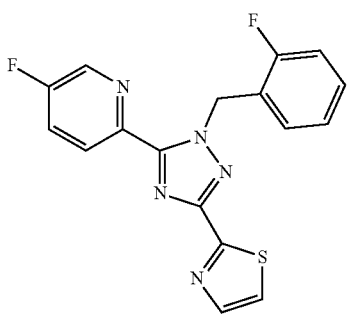
I-40 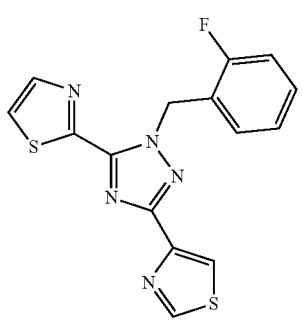
I-41 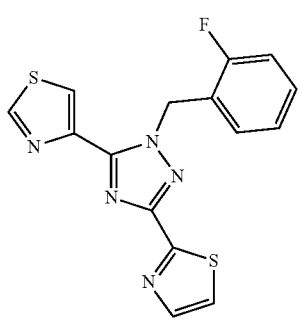
I-42 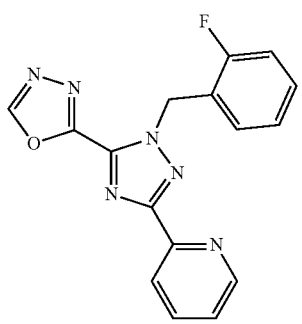
I-44 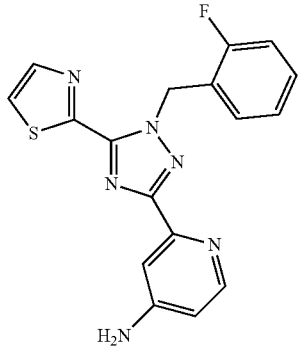

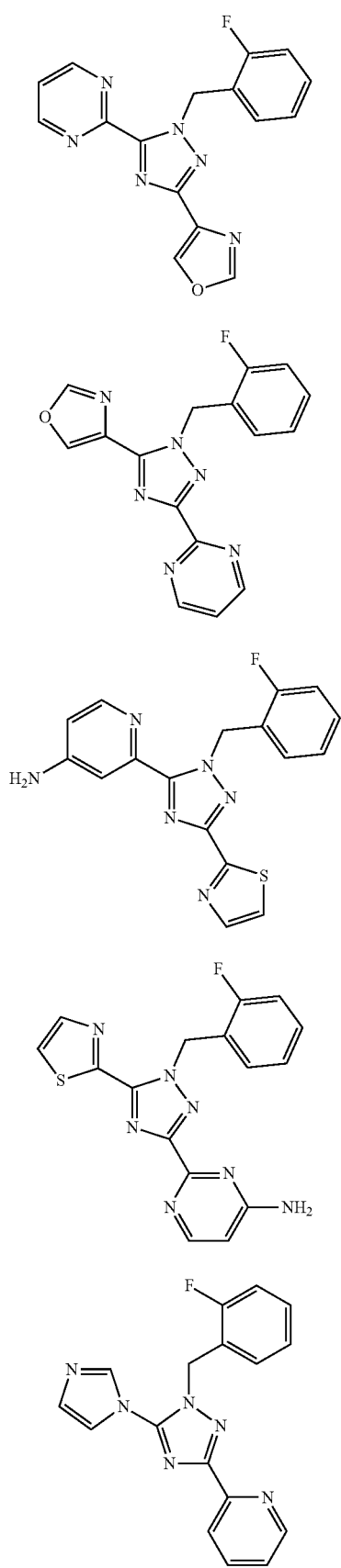
I-45
I-46
I-47
I-48
I-49
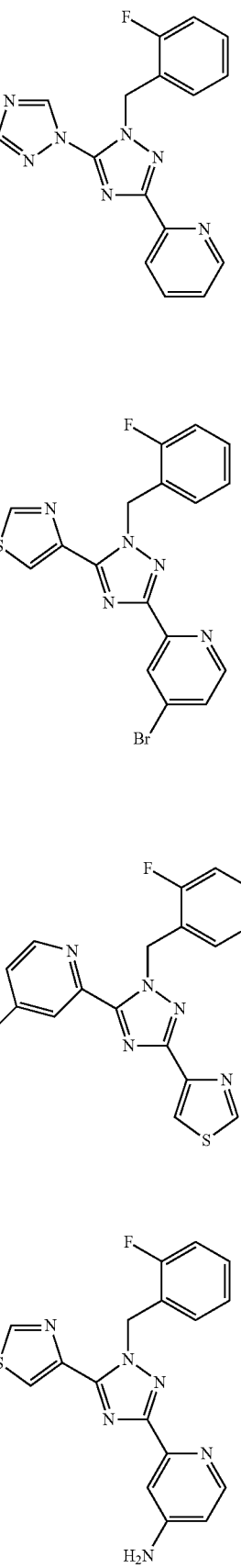
I-50
I-51
I-52
I-53

I-54
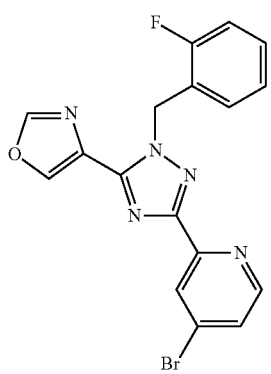
I-55
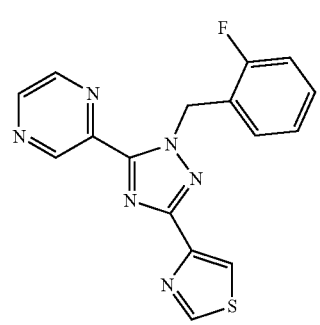
I-57
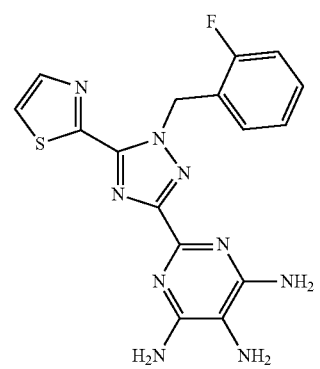
I-58
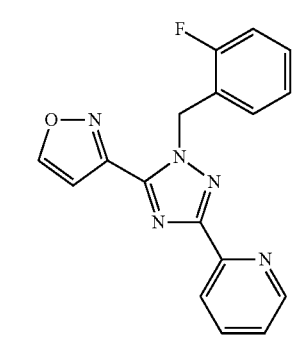
I-59
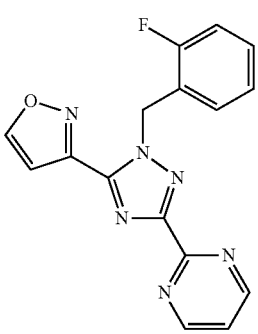
I-60
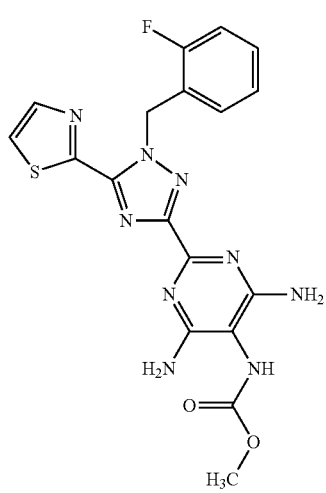
I-61
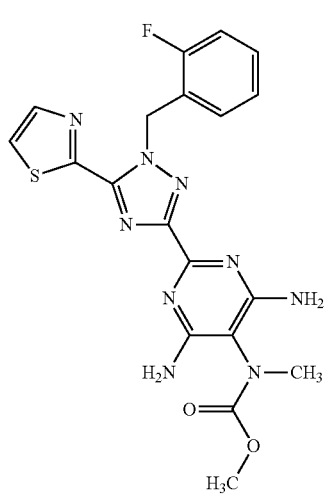
I-62
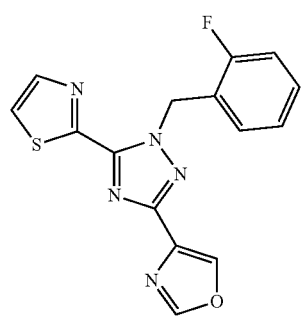

-continued
I-63
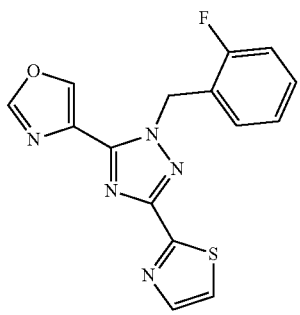
I-64
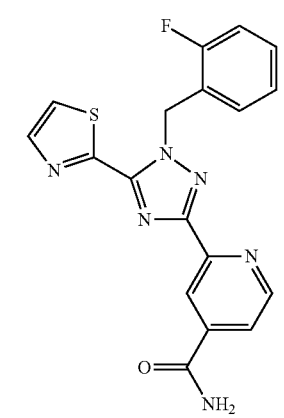
I-65
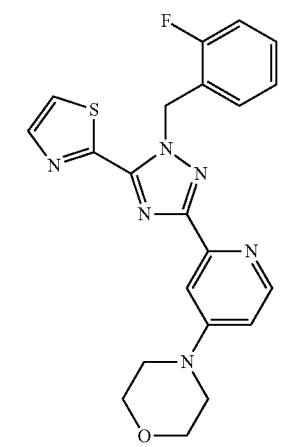
I-66
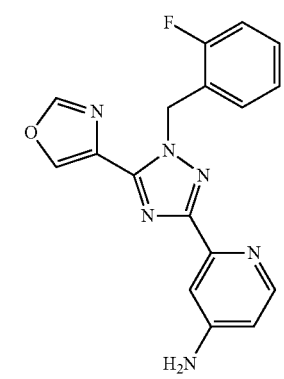
-continued
I-67A
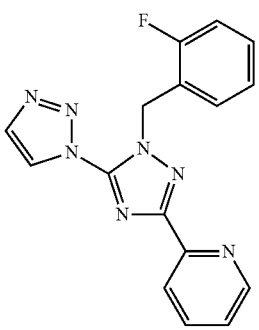
I-67B
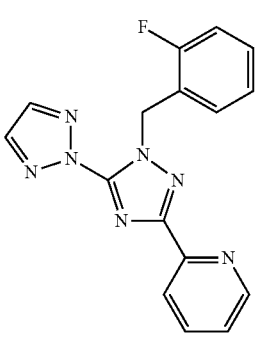
I-68
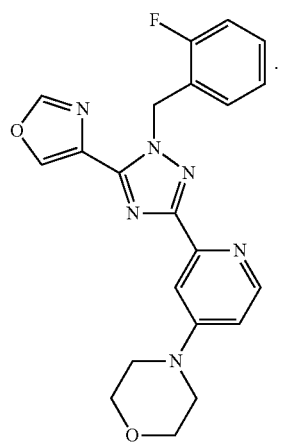
44. A pharmaceutical composition comprising the compound of claim 1, or a pharmaceutically acceptable salt thereof, and at least one pharmaceutically acceptable excipient.
* * * * *

UNITED STATES PATENT AND TRADEMARK OFFICE
CERTIFICATE OF CORRECTION

| | | |
|---|---|---|
| PATENT NO. | : 9,061,030 B2 | Page 1 of 1 |
| APPLICATION NO. | : 13/883910 | |
| DATED | : June 23, 2015 | |
| INVENTOR(S) | : Kim et al. | |

It is certified that error appears in the above-identified patent and that said Letters Patent is hereby corrected as shown below:

IN THE CLAIMS

Column 124, Line 35: Claim 14, Delete "-N(R)" and insert -- -N($R^d$) --

Signed and Sealed this
Twenty-fourth Day of November, 2015

Michelle K. Lee
*Director of the United States Patent and Trademark Office*